United States Patent
Djurovich et al.

(10) Patent No.: US 11,963,438 B2
(45) Date of Patent: Apr. 16, 2024

(54) ORGANIC ELECTROLUMINESCENT MATERIALS AND DEVICES

(71) Applicant: The University of Southern California, Los Angeles, CA (US)

(72) Inventors: Peter I. Djurovich, Long Beach, CA (US); Mark E. Thompson, Anaheim, CA (US)

(73) Assignee: The University of Southern California

( * ) Notice: Subject to any disclaimer, the term of this patent is extended or adjusted under 35 U.S.C. 154(b) by 676 days.

(21) Appl. No.: 16/830,802

(22) Filed: Mar. 26, 2020

(65) Prior Publication Data
US 2020/0308196 A1 Oct. 1, 2020

Related U.S. Application Data

(60) Provisional application No. 62/823,849, filed on Mar. 26, 2019.

(51) Int. Cl.
*H10K 85/30* (2023.01)
*C07D 471/08* (2006.01)
(Continued)

(52) U.S. Cl.
CPC ......... *H10K 85/371* (2023.02); *C07D 471/08* (2013.01); *C07D 487/08* (2013.01);
(Continued)

(58) Field of Classification Search
None
See application file for complete search history.

(56) References Cited

U.S. PATENT DOCUMENTS 4,769,292 A    9/1988  Tang
5,061,569 A   10/1991  VanSlyke
(Continued)

FOREIGN PATENT DOCUMENTS

EP   0650955   5/1995
EP   1238981   9/2002
(Continued)

OTHER PUBLICATIONS

Fernández-Fernandez et al. (Different Nuclearity Silver(I) Complexes with Novel Tetracyano Pendant-Armed Hexaazamacrocyclic Ligands, Inorganic Chemistry, vol. 45, No. 5, 2006, pp. 2266-2275. (Year: 2006).*
(Continued)

*Primary Examiner* — Katie L. Hammer
(74) *Attorney, Agent, or Firm* — Riverside Law LLP

(57) ABSTRACT

The present disclosure provides a compound of Formula I

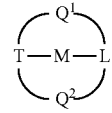

Formula I wherein
M is a metal selected from the group consisting of Cu, Ag, and Au;
T is a five-membered or six-membered heterocyclic ring, which is optionally substituted, wherein T includes a carbene carbon coordinated to M, or T is aromatic and includes a $sp^2$ nitrogen coordinated to M;
L is a group comprising a coordinating member selected from the group consisting of C, N, O, S, and P, wherein the coordinating member coordinates L to M; and
(Continued)

$Q^1$ and $Q^2$ are each independently a linker, wherein the linker connects T to the coordinating member of L to form a macrocyclic ligand coordinated to M.

19 Claims, 2 Drawing Sheets

(51) Int. Cl.
    *C07D 487/08*    (2006.01)
    *C07F 1/08*    (2006.01)
    *C07F 1/10*    (2006.01)
    *C07F 1/12*    (2006.01)
    *H10K 50/11*    (2023.01)
    *H10K 50/12*    (2023.01)

(52) U.S. Cl.
    CPC ............... *C07F 1/08* (2013.01); *C07F 1/10* (2013.01); *C07F 1/12* (2013.01); *H10K 50/11* (2023.02); *H10K 50/12* (2023.02)

(56) References Cited

U.S. PATENT DOCUMENTS

| | | |
|---|---|---|
| 5,247,190 A | 9/1993 | Friend |
| 5,703,436 A | 12/1997 | Forrest |
| 5,707,745 A | 1/1998 | Forrest |
| 5,834,893 A | 11/1998 | Bulovic |
| 5,844,363 A | 12/1998 | Gu |
| 6,013,982 A | 1/2000 | Thompson |
| 6,087,196 A | 7/2000 | Sturm |
| 6,091,195 A | 7/2000 | Forrest |
| 6,097,147 A | 8/2000 | Baldo |
| 6,294,398 B1 | 9/2001 | Kim |
| 6,303,238 B1 | 10/2001 | Thompson |
| 6,337,102 B1 | 1/2002 | Forrest |
| 6,468,819 B1 | 10/2002 | Kim |
| 6,528,187 B1 | 3/2003 | Okada |
| 6,687,266 B1 | 2/2004 | Ma |
| 6,835,469 B2 | 12/2004 | Kwong |
| 6,921,915 B2 | 7/2005 | Takiguchi |
| 7,087,321 B2 | 8/2006 | Kwong |
| 7,090,928 B2 | 8/2006 | Thompson |
| 7,154,114 B2 | 12/2006 | Brooks |
| 7,250,226 B2 | 7/2007 | Tokito |
| 7,279,704 B2 | 10/2007 | Walters |
| 7,332,232 B2 | 2/2008 | Ma |
| 7,338,722 B2 | 3/2008 | Thompson |
| 7,393,599 B2 | 7/2008 | Thompson |
| 7,396,598 B2 | 7/2008 | Takeuchi |
| 7,431,968 B1 | 10/2008 | Shtein |
| 7,445,855 B2 | 11/2008 | Mackenzie |
| 7,534,505 B2 | 5/2009 | Lin |
| 7,968,146 B2 | 6/2011 | Wagner |
| 8,409,729 B2 | 4/2013 | Zeng |
| 2002/0034656 A1 | 3/2002 | Thompson |
| 2002/0134984 A1 | 9/2002 | Igarashi |
| 2002/0158242 A1 | 10/2002 | Son |
| 2003/0138657 A1 | 7/2003 | Li |
| 2003/0152802 A1 | 8/2003 | Tsuboyama |
| 2003/0162053 A1 | 8/2003 | Marks |
| 2003/0175553 A1 | 9/2003 | Thompson |
| 2003/0230980 A1 | 12/2003 | Forrest |
| 2004/0036077 A1 | 2/2004 | Ise |
| 2004/0137267 A1 | 7/2004 | Igarashi |
| 2004/0137268 A1 | 7/2004 | Igarashi |
| 2004/0174116 A1 | 9/2004 | Lu |
| 2005/0025993 A1 | 2/2005 | Thompson |
| 2005/0112407 A1 | 5/2005 | Ogasawara |
| 2005/0238919 A1 | 10/2005 | Ogasawara |
| 2005/0244673 A1 | 11/2005 | Satoh |
| 2005/0260441 A1 | 11/2005 | Thompson |
| 2005/0260449 A1 | 11/2005 | Walters |
| 2006/0008670 A1 | 1/2006 | Lin |
| 2006/0202194 A1 | 9/2006 | Jeong |
| 2006/0240279 A1 | 10/2006 | Adamovich |
| 2006/0251923 A1 | 11/2006 | Lin |
| 2006/0263635 A1 | 11/2006 | Ise |
| 2006/0280965 A1 | 12/2006 | Kwong |
| 2007/0190359 A1 | 8/2007 | Knowles |
| 2007/0278938 A1 | 12/2007 | Yabunouchi |
| 2008/0015355 A1 | 1/2008 | Schafer |
| 2008/0018221 A1 | 1/2008 | Egen |
| 2008/0106190 A1 | 5/2008 | Yabunouchi |
| 2008/0124572 A1 | 5/2008 | Mizuki |
| 2008/0220265 A1 | 9/2008 | Xia |
| 2008/0297033 A1 | 12/2008 | Knowles |
| 2009/0008605 A1 | 1/2009 | Kawamura |
| 2009/0009065 A1 | 1/2009 | Nishimura |
| 2009/0017330 A1 | 1/2009 | Iwakuma |
| 2009/0030202 A1 | 1/2009 | Toshihiro |
| 2009/0039776 A1 | 2/2009 | Yamada |
| 2009/0045730 A1 | 2/2009 | Nishimura |
| 2009/0045731 A1 | 2/2009 | Nishimura |
| 2009/0101870 A1 | 4/2009 | Prakash |
| 2009/0108737 A1 | 4/2009 | Kwong |
| 2009/0115316 A1 | 5/2009 | Zheng |
| 2009/0165846 A1 | 7/2009 | Johannes |
| 2009/0167162 A1 | 7/2009 | Lin |
| 2009/0179554 A1 | 7/2009 | Kuma |
| 2010/0252820 A1* | 10/2010 | De Cola .............. H10K 85/371 546/10 |
| 2011/0155954 A1* | 6/2011 | Yersin ........................ C07F 5/02 252/301.16 |
| 2013/0026452 A1 | 1/2013 | Kottas |
| 2013/0119354 A1 | 5/2013 | Ma |
| 2014/0054564 A1 | 2/2014 | Kim |
| 2015/0108451 A1* | 4/2015 | Thompson .......... H01L 51/0091 548/103 |
| 2015/0228914 A1* | 8/2015 | Li ...................... H01L 51/0087 540/541 |
| 2015/0318487 A1 | 11/2015 | Ito |
| 2018/0155381 A1* | 6/2018 | Zeng .................. H01L 51/0085 |

FOREIGN PATENT DOCUMENTS

| | | |
|---|---|---|
| EP | 1725079 | 11/2006 |
| EP | 2034538 | 3/2009 |
| EP | 2551932 | 1/2013 |
| EP | 2977378 | 1/2016 |
| JP | 200511610 | 1/2005 |
| JP | 2007123392 | 5/2007 |
| JP | 2007254297 | 10/2007 |
| JP | 2008074939 | 4/2008 |
| JP | 2010135467 | 6/2010 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2004111066 A1 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008044723 | 4/2008 |
| WO | 2008056746 | 5/2008 |

(56) References Cited

FOREIGN PATENT DOCUMENTS

| WO | 2008057394 | A1 | 5/2008 |
|---|---|---|---|
| WO | 2008101842 | | 8/2008 |
| WO | 2008132085 | | 11/2008 |
| WO | 2009000673 | | 12/2008 |
| WO | 2009003898 | | 1/2009 |
| WO | 2009008311 | | 1/2009 |
| WO | 2009018009 | | 2/2009 |
| WO | 2009021126 | | 2/2009 |
| WO | 2009050290 | | 4/2009 |
| WO | 2009062578 | | 5/2009 |
| WO | 2009063833 | | 5/2009 |
| WO | 2009066778 | | 5/2009 |
| WO | 2009066779 | | 5/2009 |
| WO | 2009086028 | | 7/2009 |
| WO | 2009100991 | | 8/2009 |
| WO | 2010011390 | A2 | 1/2010 |
| WO | 2010111175 | | 9/2010 |
| WO | 2010126234 | | 11/2010 |

OTHER PUBLICATIONS

Adachi et al., "Nearly 100% Internal Phosphorescent Efficiency in an Organic Light Emitting Device," J. Appl. Phys., vol. 90, No. 10, pp. 5048-5051 (2001).
Adachi, Chihaya et al., "High-Efficiency Red Electrophosphorescence Devices," Appl. Phys. Lett., 78(11):1622-1624 (2001).
Adachi, Chihaya et al., "Organic Electroluminescent Device Having a Hole Conductor as an Emitting Layer," Appl. Phys. Lett., 55(15):1489-1491 (1989).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., "Highly Efficient Phosphorescent Emission from Organic Electroluminescent Devices," Nature, vol. 395, pp. 151-154 (1998).
Baldo et al., "Very High-Efficiency Green Organic Light-Emitting Devices Based on Electrophosphorescence," Appl. Phys. Lett., vol. 75, No. 1, pp. 4-6 (1999).
Gao, Zhiqiang et al., "Bright-Blue Electroluminescence From a Silyl-Substituted ter-(phenylenevinylene) derivative," Appl. Phys. Lett., 74(6):865-867 (1999).
Guo, Tzung-Fang et al., "Highly Efficient Electrophosphorescent Polymer Light-Emitting Devices," Organic Electronics, 1:15-20 (2000).
Hamada, Yuji et al., "High Luminance in Organic Electroluminescent Devices with Bis(10-hydroxybenzo[h] quinolinato)beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2, N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185: Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al.,"1,2,4-Triazole Derivative as an Electron Transport Layer in Organic Electroluminescent Devices," Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong et al., "High Operational Stability of Electrophosphorescent Devices," Appl. Phys. Lett., vol. 81, No. 1, pp. 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21):5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode: an Isoindole Derivative," Chem. Mater., 15(16):3148-3151 (2003).
Nishida, Jun-ichi et al., "Preparation, Characterization, and Electroluminescence Characteristics of a-Diimine-type Platinum(II) Complexes with Perfluorinated Phenyl Groups as Ligands," Chem. Lett., 34(4):592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,6-Bis(dinnesitylboryl)-2,2'-bithiophene and 5,5"-Bis (dimesitylbory1)-2,2':5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S, et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91:209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Ostergard et al., "Langmuir-Blodgett Light-Emitting Diodes of Poly(3-Hexylthiophene): Electro-Optical Characteristics Related to Structure," Synthetic Metals, 87:171-177 (1997).

(56) References Cited

OTHER PUBLICATIONS

Takizawa, Shin-ya et al., "Phosphorescent Iridium Complexes Based on 2-Phenylimidazo[1,2-a]pyridine Ligands: Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8):1059-1064 (2005).

Van Slyke, S. A. et al., "Organic Electroluminescent Devices with Improved Stability," Appl. Phys. Lett, 69(15 ):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., "A Novel Class of Phosphorescent Gold(III) Alkynyl-Based Organic Light-Emitting Devices with Tunable Colour," Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Application No. 62/823,849 filed Mar. 26, 2019, the entire contents of which are incorporated herein by reference.

FIELD

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

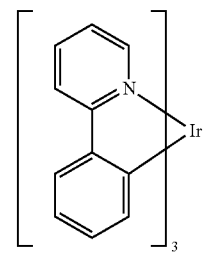

In this, and later figures herein, we depict the dative bond from nitrogen to metal (here, Ir) as a straight line.

SUMMARY

A compound of formula I is disclosed herein:

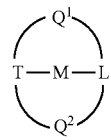

Formula I wherein
M is a metal selected from the group consisting of Cu, Ag, and Au;
T is a five-membered or six-membered heterocyclic ring, which is optionally substituted, wherein T includes a carbene carbon coordinated to M, or T is aromatic and includes a sp$^2$ nitrogen coordinated to M;
L is a group comprising a coordinating member selected from the group consisting of C, N, O, S, and P, wherein the coordinating member coordinates L to M; and
Q$^1$ and Q$^2$ are each independently a linker, wherein the linker connects T to the coordinating member of L to form a macrocyclic ligand coordinated to M.

An OLED comprising the compound of the present disclosure in an organic layer therein is also disclosed.

A consumer product comprising the OLED is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
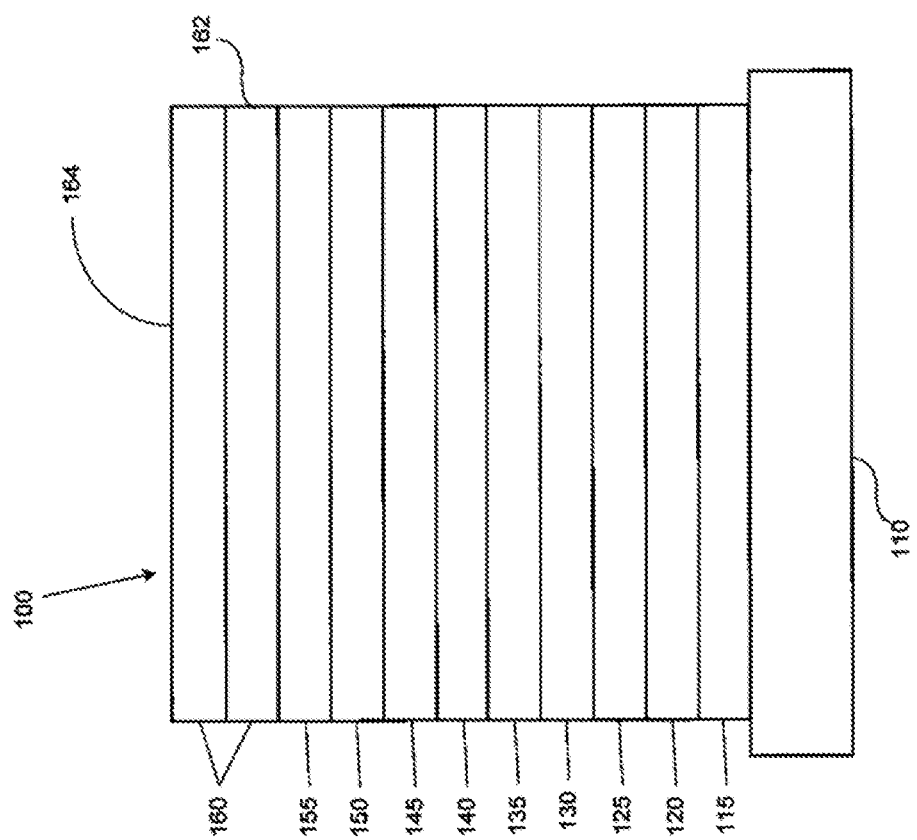
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
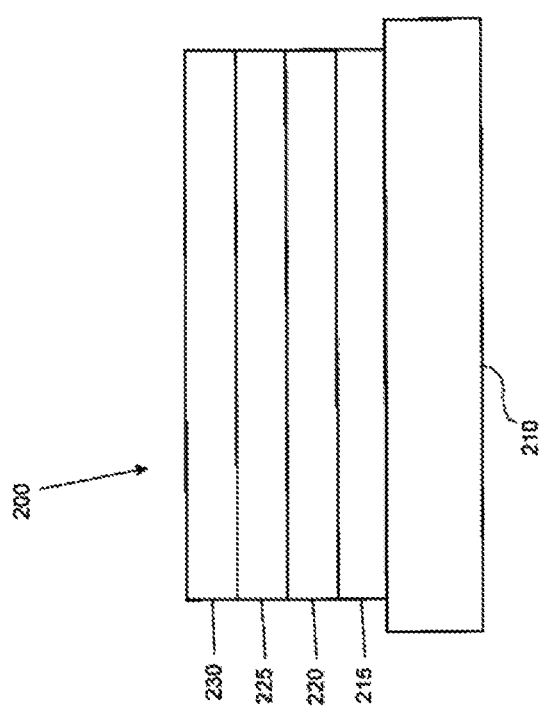
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —$OR_s$ radical.

The terms "sulfanyl" or "thio-ether" are used interchangeably and refer to a —$SR_s$ radical.

The term "sulfinyl" refers to a —S(O)—$R_s$ radical.

The term "sulfonyl" refers to a —$SO_2$—$R_s$ radical.

The term "phosphino" refers to a —$P(R_s)_3$ radical, wherein each $R_s$ can be same or different.

The term "silyl" refers to a —$Si(R_s)_3$ radical, wherein each $R_s$ can be same or different.

The term "boryl" refers to a —$B(R_s)_2$ radical or its Lewis adduct —B(Rs)3 radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group is optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., Tetrahedron 2015, 71, 1425-30 and Atzrodt et al., Angew. Chem. Int. Ed. (Reviews) 2007, 46, 7744-65, which are incorporated by reference in their entireties, describe the deuteration of the methylene hydrogens in benzyl amines and efficient pathways to replace aromatic ring hydrogens with deuterium, respectively.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

Currently, the only reported luminescent 2-coordinate Cu(I) compounds are: neutral, 2-coordinate carbene-Cu-amide compounds described in U.S. Pat. No. 9,853,229; a cationic bis-lutidine compound which is luminescent only at 77K described in, Simon et al., Inorg. Chem., 1996, 35:6413-21; cationic bis-carbene compounds described in, Shi et al., Dalton Trans., 2017, 46:745-752, and Gernert et al., Chem. Eur. J., 2017, 23:2206-16; and neutral carbene-Cu halides, aryls, acetylides, alkoxides, thiolates, and amides described in Romanov et al., Chem Commun., 2016, 52: 6379-6382, Hamze et al., Chem Commun., 2017, 53:9008-11, and Bochmann et al. Chem. Eur. J., 2017, 23:4625-37. Additionally, a series of Cu(I) compounds featuring a sterically demanding thiolate ligand and a monodentate phosphine, lutidine, ether, thioketone, and NHC were reported in 2008, and did not include any photophysical characterization.

As used herein, "electron-withdrawing substituent" refers to an individual atom, e.g., fluorine, or a functional group that withdraws electron density from a conjugated ring system e.g., an aromatic ring system. Some examples of electron-withdrawing groups include —F, —CF$_3$, —NO$_2$, and ester.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

In one aspect, the disclosure provides a class of luminescent two-coordinate metal(I) compounds with planar or twisted geometry (i.e., opposite coordinating ring systems out of plane) about the metal. In one embodiment, the metal(I) is selected from Cu(I), Ag(I), and Au(I).

In one embodiment, the compounds can be further described as a combination of a bidentate macrocyclic ligand with a carbene or π-acid coordination at one end and a neutral, electron donating coordination group at the opposite end.

In one embodiment, the compounds can be further described as a bidentate macrocyclic ligand with a carbene or π-acid coordination at one end and an anionic, electron donating coordination group at the opposite end. In one embodiment, the described compounds are macrocyclic, two-coordinate metal(I) compounds that can have an overall cationic or neutral charge, respectively.

Described herein are luminescent two-coordinate, macrocyclic metal(I) compounds that include a carbene coordinating group or a π-acid group, each of which together with an electron donating group form a special class of donor-acceptor metal(I) compounds.

In one embodiment, the compounds have an overall neutral charge and include an electron donating group. In one embodiment, the electron donating group includes an organoamide, an alkylide, an arylide, an organooxide, an organosulfide, or an organophosphide. In one embodiment, the organoamide, alkylide, arylide, organooxide, or organosulfide are part of a molecular ring structure that is optionally substituted. In one embodiment, the molecular ring structure comprises an aromatic ring system that includes two or more fused ring structure, that is substantially planar. In one embodiment, the molecular ring structure comprises an aromatic ring system that includes a two to five fused ring structure, that is substantially planar.

In one embodiment, the amide, arylide, oxide, or sulfide comprises substituents that crowd or protect the metal center. In one embodiment, the amide, arylide, oxide, or sulfide enhances the stability of the compound in its ground and/or its electronically excited states.

In one embodiment, the macrocyclic ligand that includes donor and acceptor functionality enhances the structural stability of the compound in both its ground state as well as in its electronic excited state.

In one embodiment, the macrocyclic compounds are substantially planar ring systems (i.e., slightly twisted and less than 30° out of plane). In one embodiment, the macrocyclic compounds are twisted out of the plane relative to the ring system of the opposite coordinating ligand member. In one embodiment the macrocyclic compounds are twisted out of the plane relative to the ring T of formula (I). In one embodiment, the angle of twist out of the plane is 30° to 90°. In one embodiment, the angle of twist out of the plane is 50° to 90°. °. In one embodiment, the angle of twist out of the plane is 65° to 90°.

In one aspect, the disclosure provides a compound of formula I:

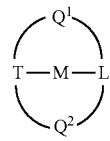

Formula I wherein
M is a metal selected from the group consisting of Cu, Ag, and Au;
T is a five-membered or six-membered heterocyclic ring, which is optionally substituted, wherein T includes a carbene carbon coordinated to M, or T is aromatic and includes a sp$^2$ nitrogen coordinated to M;
L is a group comprising a coordinating member selected from the group consisting of C, N, O, S, and P, wherein the coordinating member coordinates L to M; and
Q$^1$ and Q$^2$ are each independently a linker, wherein the linker connects T to the coordinating member of L to form a macrocyclic ligand coordinated to M.

In one embodiment, T is selected from the group consisting of:

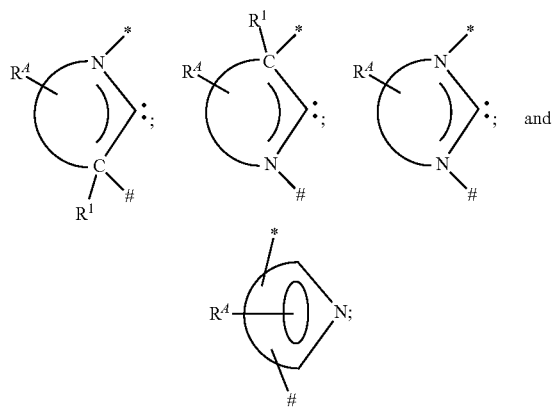

wherein
R$^4$ represents mono to the maximum allowable substitution, or no substitution and each R$^4$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, nitrile, isonitrile, sulfanyl, boryl, acyl, carboxylic acid, ether, ester, sulfinyl, sulfonyl, phosphino and combinations thereof;

each $R^1$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, nitrile, isonitrile, sulfanyl, boryl, acyl, carboxylic acid, ether, ester, sulfinyl, sulfonyl, phosphino and combinations thereof;

wherein any two adjacent $R^A$ are optionally joined or fused together to form a ring which is optionally substituted; adjacent $R^A$ and $R^1$ are optionally joined for fused together to form a ring which is optionally substituted; and

* represents a connection to $Q^1$ and # represents a connection to $Q^2$.

In one embodiment, L is a group comprising an aryl or heteroaryl. For example, in one embodiment, L comprises a phenyl, pyridyl, pyridazinyl, pyrimidinyl, pyrazinyl, or triazinyl group, wherein L is optionally substituted.

In one embodiment, L comprises a phenyl. In one embodiment, the phenyl ring is optionally substituted, particularly in one or both of the ortho positions (in relation to the C-M bond).

In one embodiment, L is selected from the group consisting of benzene, naphthalene, and anthracene, or a heteroaryl ring coordinated to M through a ring carbon. In one embodiment, the heteroaryl ring selected from pyridine, pyrimidine, pyrazine, or benzo-analogs of each thereof. For example, the aryl ring can also be part of a fused polycyclic ring system, e.g., quinoline. Given that an aryl (L is C) is a formal −1 ligand, the metal(I) carbene or π-acid compound would be neutral.

In one embodiment, the coordinating member of L comprises O or S. For example, in one embodiment, the L comprises an organoxide or an organosulfide. In one embodiment, coordinating member is O or S and the O or S is directly or indirectly bonded to a substituted aryl or heteroaryl ring. In one embodiment, given that an oxide or sulfide is a formal −1 ligand, the metal(I) carbene or π-acid compound would be neutral.

In one embodiment, L comprises a five-membered or six-membered heterocyclic ring, wherein the coordinating member is O or S and is a member of the heterocyclic ring. In one embodiment, the five-membered or six-membered heterocyclic ring is optionally substituted. In one embodiment, when L comprises a five-membered or six-membered heterocyclic ring, wherein the coordinating member is O or S the metal(I) carbene or π-acid compound has an overall charge of +1.

In one embodiment, L is a group of formula L1 and the coordinating member of L is C

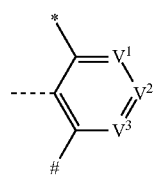

formula L1 wherein

* represents a connection to $Q^1$ and # represents a connection to $Q^2$, and the dotted line represents coordination to M;

$V^1$, $V^2$, and $V^3$ are independently selected from the group consisting of $CR^B$ and N, wherein at least one of $V^1$, $V^2$, or $V^3$ is $CR^B$; and each $R^B$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, nitrile, isonitrile, sulfanyl, and combinations thereof; wherein, any two adjacent $R^B$ are optionally joined or fused to form a ring, which is optionally substituted.

In one embodiment, L is a group of Formula L2 or Formula L3 and the coordinating member of L is N

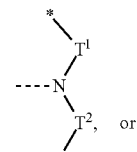

formula L2

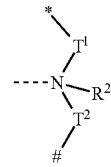

formula L3 wherein

* represents a connection to $Q^1$ and # represents a connection to $Q^2$, and the dotted line represents coordination to M;

$T^1$ and $T^2$ are each independently a group comprising a sp$^2$ C or a sp$^3$ C, wherein $T^1$ and $T^2$ are optionally joined or fused to form a ring, which is optionally substituted;

$R^2$ is selected from the group consisting of hydrogen, deuterium, halogen, alkyl, cycloalkyl, cycloalkenyl, aryl, heteroaryl, and combinations thereof;

$R^B$ represents mono to the maximum allowable substitution, or no substitution, and each $R^B$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, nitrile, isonitrile, sulfanyl, and combinations thereof, wherein any two adjacent $R^B$ are optionally joined or fused to form a ring, which is optionally substituted.

In one embodiment, formula L2 is

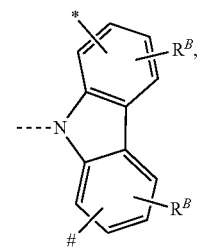

or an aza-analog thereof, wherein L2 is optionally further substituted with a group $R^B$.

In one embodiment, formula L2 is selected from the group consisting of

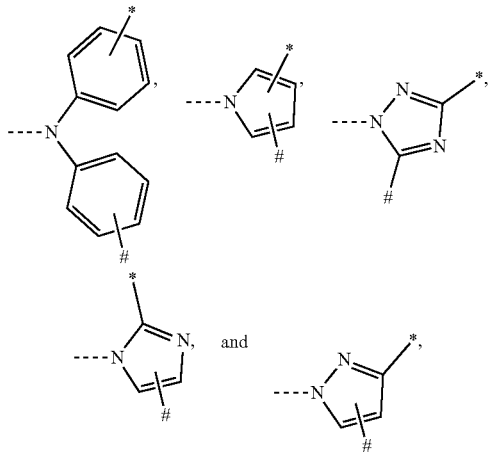

or an aza-analog thereof, wherein L2 is optionally further substituted with a group $R^B$.

In one embodiment, L is a ligand group structure, which is optionally a ring structure that substituted or non-substituted, and comprises a coordinating member, wherein the coordinating member coordinates L to M. In one embodiment the ligand group structure comprises carbazolides, diphenylamides, substituted phenyl, a substituted phenyl oxide, or a substituted phenyl sulfide, or aza-analogs thereof. Representative monodentate neutral ligands include, but not limited to, tertiary amines, N-heteroaryl ligands (e.g., pyridyl, pyrimidine, triazole), phosphines, e.g., triaryl or triaryloxy phosphines. In one embodiment, any group ligands are optionally substituted to sterically enhance the stabilization of the excited state in each metal(I) carbene or metal(I) π-acid compound, and therefore, improve upon corresponding device lifetimes. The compounds can exhibit high quantum efficiency up to 100% in fluid and polymeric matrices with radiative rates on the order of $10^5$ $s^{-1}$, which are unknown for Cu(I), Ag(I) or Au(I) metal centers. These radiative rates are comparable to state of the art known organoiridium and organoplatinum phosphorescent complexes In one embodiment, when T, L, or both comprise a substituent having a sterically bulky substituent group, the compound of Formula (I) is more sterically encumbered. In one embodiment, the steric encumbrance provides steric protection of M of Formula (I). In one embodiment, the steric protection leads to an increase in stability of the compound in its electronic excited state and an increase in the corresponding operational lifetime of fabricated electronic light emitting devices. Such coordination geometries can hinder rotation around the C-M/M-N bonds, thereby allowing for the elucidation of the role of molecular rotation and of the coordination environment on the photophysical properties of the compounds of Formula (I).

In one embodiment, $R^A$ and $R^B$ are each independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In one embodiment, $R^A$ and $R^B$ are each independently hydrogen or a substituent selected from the group consisting of deuterium, fluorine, alkyl, cycloalkyl, aryl, heteroaryl, and combinations thereof.

In one embodiment, M is Cu(I), Ag(I), or Au(I). In one embodiment, M is Cu(I), Ag(I).

In one embodiment, $Q^1$ and $Q^2$ each independently comprise a backbone of five to ten member atoms, and $Q^1$ and $Q^2$ each independently optionally comprises a five-membered or six-membered carbocyclic or heterocyclic ring.

In one embodiment, $Q^1$ and $Q^2$ are each independently an organic linker. For example, in one embodiment, $Q^1$ and $Q^2$ are each independently an alkylene saturated or unsaturated chain with a backbone of five to ten member atoms, which optionally comprises one to three heteroatoms such as O or S.

In one embodiment, the organic linker comprises a ring structure. For example, in one embodiment, the organic linker comprises a phenylene or cyclohexyl ring, which is optionally substituted.

In one embodiment, the alkylene linker comprises a point of unsaturation. For example, in one embodiment, the alkylene linker comprises a vinyl group. In one embodiment, the point of unsaturation provides conformational control to the alkylene linker.

In one embodiment, the compound is a compound of Formula IA, Formula IB or Formula IC:

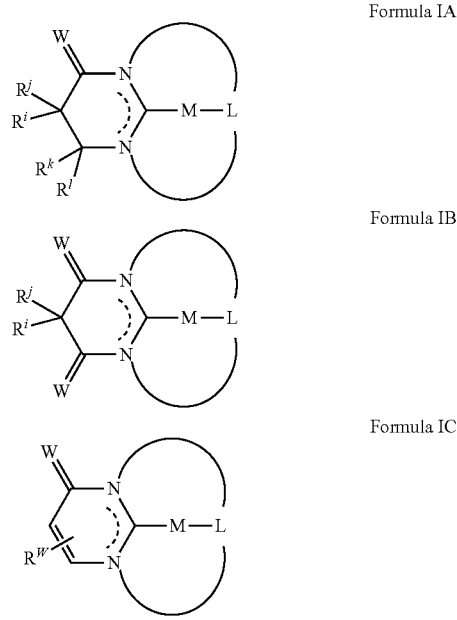

wherein
each M is a metal independently selected from the group consisting of Cu, Ag, and Au;
each L is group comprising a coordinating member independently selected from the group consisting of C, N, O, S, and P;
each W is independently selected from the group consisting of O, S, $CR^mR^n$, $SiR^mR^n$, and $GeR^mR^n$;
$R^W$ represents mono to the maximum allowable substitution, or no substitution;
each $R^i$, $R^j$, $R^k$, $R^l$, $R^m$, $R^n$, and $R^w$ is independently hydrogen or a substituent selected from the group consisting of, deuterium, halogen, alkyl, cycloalkyl, heteroalkyl, arylalkyl, amino, silyl, aryl, heteroaryl, and combinations thereof;

any two $R^i$, $R^j$, $R^k$, and $R^l$ are optionally joined for fused together to form a ring which is optionally substituted;

any two adjacent $R^m$ and $R^n$ are optionally joined for fused together to form a ring which is optionally substituted; and any two adjacent $R^W$ are optionally joined for fused together to form a ring which is optionally substituted.

In one embodiment, $R^i$, $R^j$, $R^k$, $R^l$, $R^m$, and $R^n$ are independently hydrogen or a substituent selected from the group consisting of deuterium, alkyl, cycloalkyl, heteroalkyl, aryl, heteroaryl, and combinations thereof.

In one embodiment $R^i$ optionally joins with $R^j$ to form a ring, which is optionally substituted.

In one embodiment, two $R^W$ optionally join to form a ring, which is optionally substituted.

In one embodiment, the compound is selected from the group consisting of:

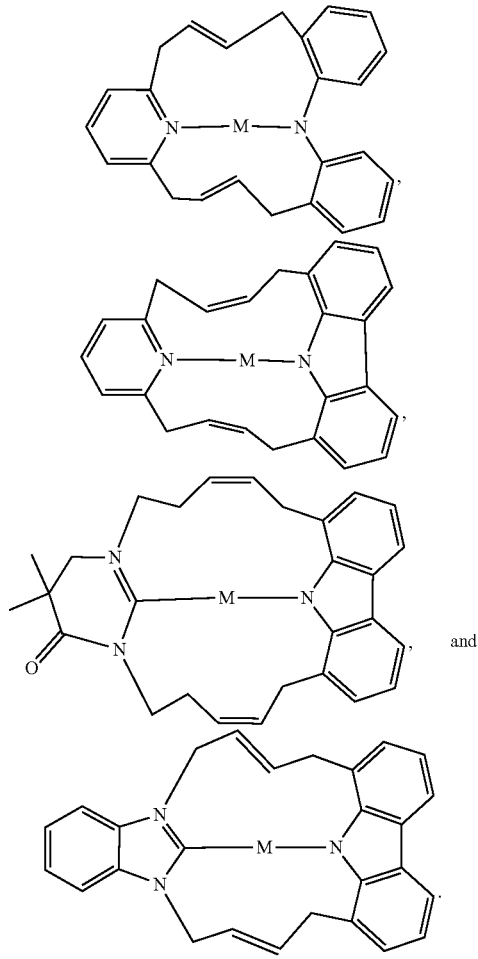

In one embodiment, the compound has an emission lifetime of 0.01 μs to 5 μs. In one embodiment, the compound has an emission lifetime of 0.05 μs to 2 μs. In one embodiment, emission lifetime is measured in a polystyrene film at 23° C.

In one embodiment, the compound has an energy separation (ΔE) of the lowest excited singlet state and triplet states from 10 meV to 150 meV.

In one embodiment, the compound has an emission wavelength of 450 nm to 530 nm.

In one embodiment, the compound has an emission wavelength of 530 nm to 650 nm.

In one embodiment, the compound is an E-type delayed fluorescent emitter.

In one embodiment, when T comprises a coordinating carbene, T contributes mostly to the LUMO and the coordinating member L, and its corresponding ligand group contributes to the HOMO. Thus, in one embodiment, the electronic transition of interest is a ligand-to-ligand charge transfer. In one embodiment, the macrocyclic ligand both enhances the compounds thermal stability and increases the radiative rates by locking the two ligands into a substantially coplanar conformation.

In one embodiment, the character of the radiative transition is charge transfer from the electron rich L, e.g., an organoamide or arylide, to the electron-deficient ring T with the carbene or π-acid ligand group, with little metal centered contribution. In one embodiment, the associated charge transfer (CT) state is characterized by a high extinction coefficient in absorption ($\varepsilon \sim 10^3$ M$^{-1}$·cm$^{-1}$). In one embodiment, the CT state in question exhibits a small energy splitting between its singlet and triplet manifolds, with $\Delta E_{1CT\text{-}3CT} \leq 150$ meV resulting in compounds that resemble highly efficient thermally activated delayed fluorescence (TADF) compounds. In one embodiment, the CT state in question exhibits a small energy splitting between its singlet and triplet manifolds, with $\Delta E_{1CT\text{-}3CT} \leq 100$ meV. In one embodiment, the singlet and triplet manifolds ($\Delta E_{1CT\text{-}3CT}$) are defined in a range from 10 meV to 150 meV, 20 meV to 100 meV, 20 meV to 80 meV, or 30 meV to 60 meV.

In one embodiment, the compound of Formula (I) comprising an amide coordinating ligand group has a closely lying localized triplet state, $^3$LE, which is amide-centered, e.g., carbazolide-centered. In one embodiment, the compound of Formula (I) comprising an amide with a carbazolide linking group has a closely lying localized triplet state, $^3$LE, which is amide centered. In one embodiment, the $^3$LE can admix with $^3$CT to varying degrees, depending on the solvating matrix as well as on the nature of the carbene. Thus, in one embodiment, emission color (and the related $^{1/3}$CT/$^3$LE ordering) can be tuned as desired by modulating the electron-accepting ability of the carbene and the electron donating ability of the amide. Thus, in one embodiment, color tuning of the compounds of formula (1) are over 240 nm, i.e., from deep blue/violet, to red, and therefore, cover most, if not all, of the visible spectrum.

In one embodiment, the compounds of Formula (I) have an advantage of highly luminescent compounds with fast radiative rates in fluid and polymeric media. In one embodiment, the compounds of Formula (I) exhibit efficient TADF with small $\Delta E_{1CT\text{-}3CT}$ ($\leq 150$ meV) and large radiative rate constants ($k_r \geq 10^5$ s$^{-1}$), which is not common in prior metal (I) TADF emitters. In one embodiment, the use of redox active ligands bridged by the d-orbitals of the metal(I) center provides these unique photophysical features, and thereby, circumventing the TADF conundrum typical of organic systems while minimizing reorganization energies typical of metal(I) systems.

In one embodiment, when M is Cu(I), the compound of Formula (I) is highly luminescent compounds with fast a radiative rate in fluid and polymeric media. In one embodiment, these compounds exhibit efficient TADF with small $\Delta E_{1CT\text{-}3CT}$ ($\leq 150$ meV) and large radiative rate constants ($k_r \geq 10^5$ s$^{-1}$), which is not common in prior Cu(I) TADF emitters. In one embodiment, the use of redox active ligands bridged by the d-orbitals of the Cu(I) provides these unique photophysical features, and thereby, circumventing the TADF conundrum typical of organic systems while minimizing reorganization energies typical of Cu(I) systems.

In one embodiment, the compounds of Formula (I) quite unexpectedly exhibit highly efficient TADF. For example, in one embodiment, the compounds of Formula (I) exhibit high quantum efficiency up to 100% in polystyrene films with short decay lifetimes of less than 20 μs, e.g. from 0.1 μs to 20 μs, from 1 μs to 12 μs, or from 0.5 μs to 6 μs. The radiative rate constants of the compounds are in the order of $10^5$ s$^{-1}$ which are extraordinary for Cu(I) compounds and comparable to those efficient phosphorescent emitters with noble metals like Ir and Pt.

In one embodiment, the M is Ag(I) or Au(I) and comprise amide coordination members. In one embodiment, when M is Ag(I), the compound of Formula (I) has sub-microsecond radiative lifetimes that take advantage of triplet excited states. This constitutes an order-of-magnitude enhancement over the radiative lifetimes of state-of-the-art phosphorescent dopants based on six-coordinate Ir(III) compounds, which are presently used as visible light emitters in OLEDs and high-end consumer display products. The sub-microsecond radiative lifetimes for these compounds is important for mediating second-order quenching processes complicit in device degradation. Moreover, the luminescence of these coinage metal complexes can be tuned efficiently over the visible spectrum; deep blue, sky blue, green, and yellow emitters were isolated with high photoluminescent quantum yields (PLQY, $\Phi_{PL}$) and high radiative rates.

In another aspect, the disclosure includes an organic electroluminescent device (OLED) comprising: an anode, a cathode, and an organic layer disposed between the anode and the cathode comprising a compound of Formula I.

In some embodiments, the OLED further comprises a layer comprising a delayed fluorescent emitter. In some embodiments, the OLED comprises an RGB pixel arrangement or white plus color filter pixel arrangement. In some embodiments, the OLED is a mobile device, a hand held device, or a wearable device. In some embodiments, the OLED is a display panel having less than 10-inch diagonal or 50 square inch area. In some embodiments, the OLED is a display panel having at least 10-inch diagonal or 50 square inch area. In some embodiments, the OLED is a lighting panel.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In one embodiment, the organic layer is an emissive layer and a compound of Formula (I) is an emissive dopant. In one embodiment, the organic layer is an emissive layer and a compound of Formula (I) is a host.

In one embodiment, the organic layer is an emissive layer and further comprises a first phosphorescent emitting material. In one embodiment, the luminescent radiation comprises a second radiation component. In one embodiment, the second radiation component arises from the first phosphorescent emitting material. In one embodiment, the emissive layer further comprises a second phosphorescent emitting material.

In one embodiment, the luminescent radiation is a white light.

In one embodiment, the first radiation component is a blue light with a peak wavelength of about 400 nm to about 500 nm. In one embodiment, the first radiation component is a yellow light with a peak wavelength of about 530 nm to about 580 nm.

In one embodiment, in the compound of Formula (I), the metal(I) coordination environment is fine-tuned resulting in a blue emitting dopant, a green emitting dopant, an orange (amber) emitting dopant, or a red emitting dopant.

The term "red emitting dopant" refers to a compound of the invention with a peak emissive wavelength of from 580 nm to 680 nm, or from 600 nm to 660 nm, or from 615 nm to 635 nm. The term "green emitting dopant" refers to a compound of the invention with a peak emissive wavelength of 500 nm to 580 nm, or from 510 nm to 550 nm. The term "blue emitting dopant" refers to a compound of the invention with a peak emissive wavelength of from 410 nm to 490 nm, or from 430 nm to 480 nm, or from 440 nm to 475 nm. Lastly, the term "amber emitting dopant" refers to a compound of the invention with a peak emissive wavelength of from 570 nm to 600 nm.

In one embodiment, the compound of Formula (I) produces emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes.

In one embodiment, the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the thermal population between the triplet states and the singlet excited states. Compounds that are capable of generating E-type delayed fluorescence are required to have very small singlet-triplet gaps. Thermal energy can activate the transition from the triplet state back to the singlet state. This type of delayed fluorescence is also known as thermally activated delayed fluorescence (TADF). A distinctive feature of TADF is that the delayed component increases as temperature rises due to the increased thermal energy. If the reverse intersystem crossing rate is fast enough to minimize the non-radiative decay from the triplet state, the fraction of back populated singlet excited states can potentially reach 75%. The total singlet fraction can be 100%, far exceeding the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic ring.

In one embodiment, the compound of Formula I is a TADF emitter. Accordingly, in one embodiment, the device emits a luminescent radiation at room temperature when a voltage is applied across the organic light emitting device, and the luminescent radiation comprises a first radiation component. In one embodiment, the first radiation component is from a delayed fluorescent process or triplet exciton harvesting process. In one embodiment, the lifetime of the first radiation component is at least 1 microsecond.

In one embodiment, the compound of Formula I exhibits remarkably strong permanent dipoles $\mu_D$ in a range from 4D to 24D. For example, in one embodiment, the compound of Formula I exhibits permanent dipoles $\mu_D$ from 8 D to 20 D. For example, in one embodiment, the compound of Formula I exhibits permanent dipoles $\mu_D$ greater than 11 D (calculated). In one embodiment, the permanent dipoles $\mu_D$ gives rise to remarkable solvatochromic properties.

In one embodiment, the compounds of Formula I exhibit relatively unusual and high thermal stability. In one embodiment, the thermal stability of the compounds of Formula (I) allows for obtaining the compounds with high purity via sublimation, which provides for the fabrication of vapor-deposited organic layers, e.g., an organic emitting layer, in OLEDs In one embodiment, the OLED further comprises a second OLED, and the second OLED device is stacked on the first device In one embodiment, the compounds of Formula I have an advantage of minimizing or avoiding certain modes of excited-state distortion, and thereby allowing for the suppression of non-radiative decay rates ($k_{nr}$). In one embodiment, the compounds of Formula I provide an opportunity to structurally modify either side of the donor or acceptor portion of the macrocyclic ligand, which leads to electronic, e.g., the donor-acceptor properties of the complex, and steric modification, e.g., device stability. The result is that one can tune the photophysical properties, i.e. emission energies can be tuned throughout visible spectrum and frontier orbital energies can be tuned for devices. Moreover, selective ligand modification can provide for charge transport and charge trapping to occur on the ligands themselves with little contribution from the metal. This minimizes large reorganization energies associated with MLCT transitions in the metal(I) complexes In one embodiment, the device emits a luminescent radiation at room temperature when a voltage is applied across the organic light emitting device, and the luminescent radiation comprises a first radiation component that arises from a delayed fluorescent process or triplet exciton harvesting process.

In embodiment, the organic layer comprises a compound of Formula (I) wherein the compound of Formula (I) is an emissive dopant or a non-emissive dopant. In embodiment, the organic layer comprises a compound of Formula (I) wherein the compound of Formula (I) is an emissive dopant and further comprises a host.

In one embodiment, the organic layer further comprises a host, wherein the host comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

In one embodiment, the host is selected from the group consisting of:

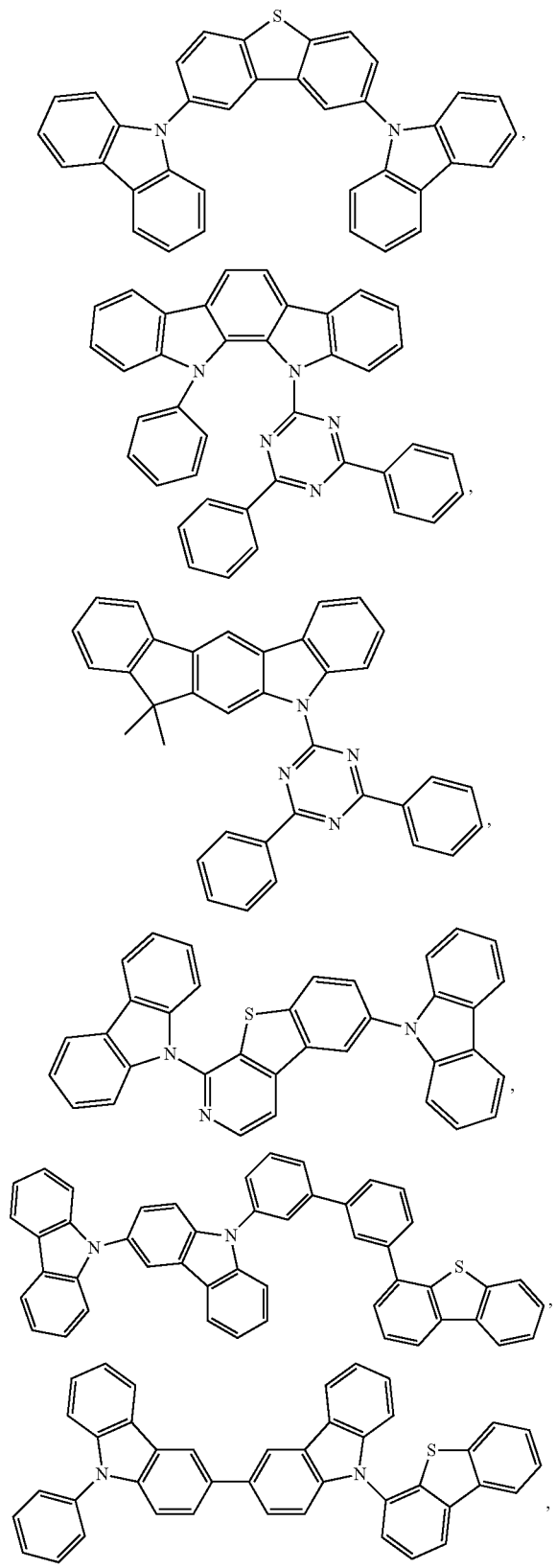

23
-continued
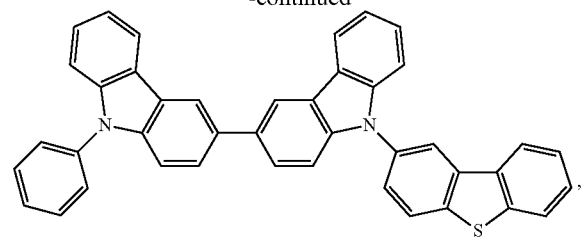
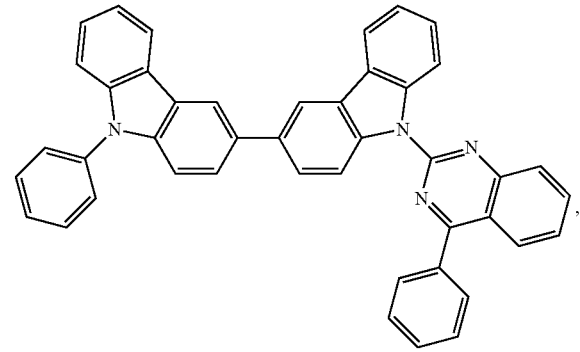
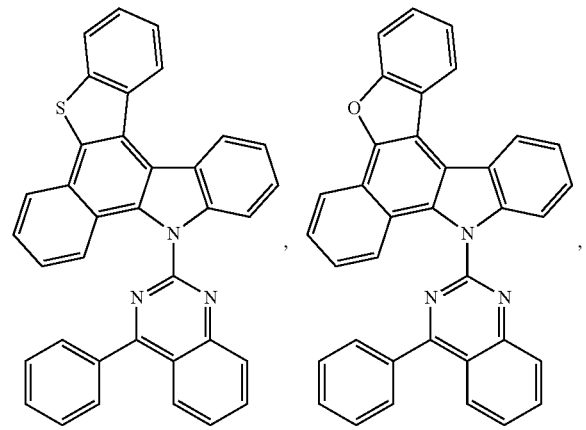
24
-continued
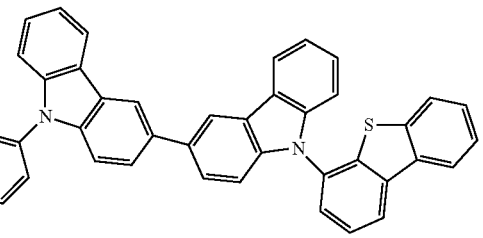
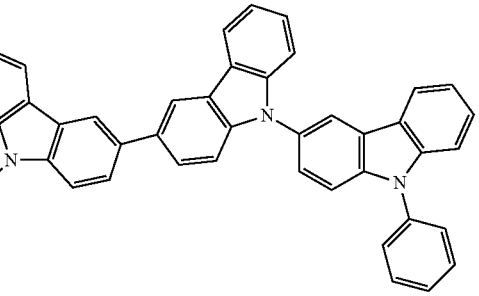
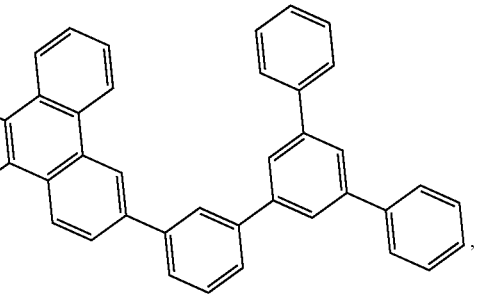
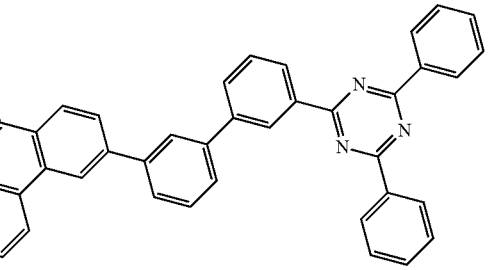
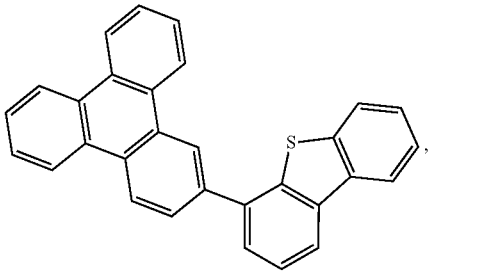
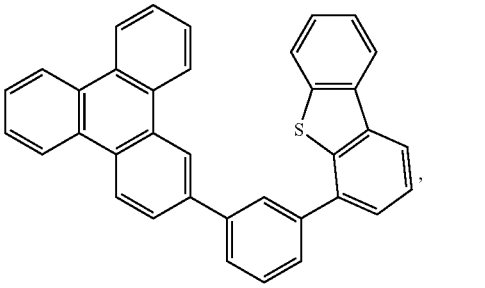

-continued

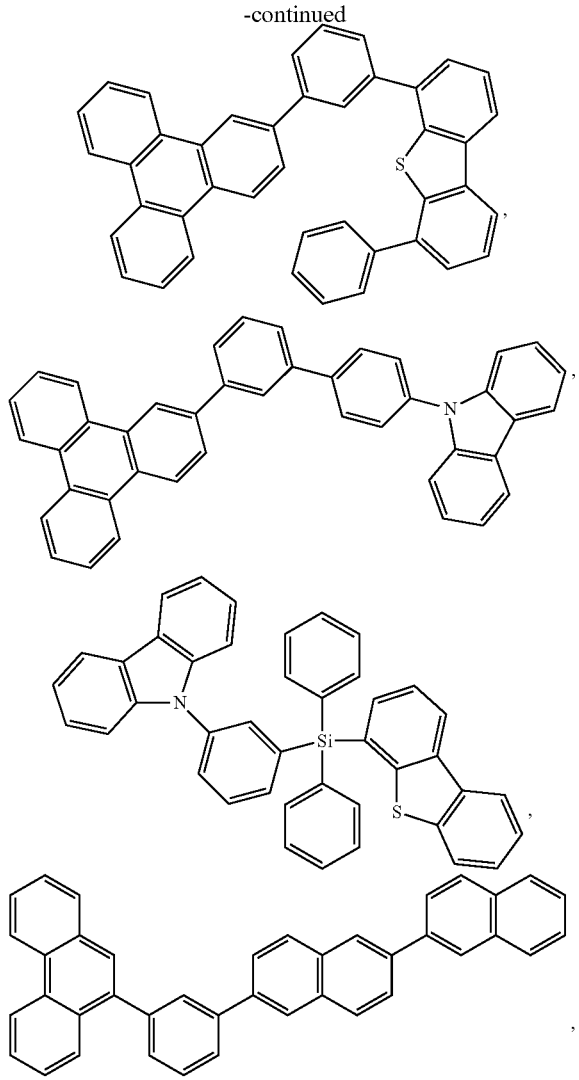

and combinations thereof.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound is neutrally charged. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiments, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer. As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers. In some embodiments, the acceptor is a TADF emitter. In some embodiments, the acceptor is a fluorescent emitter. In some embodiments, the emission can arise from any or all of the sensitizer, acceptor, and final emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used may be a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

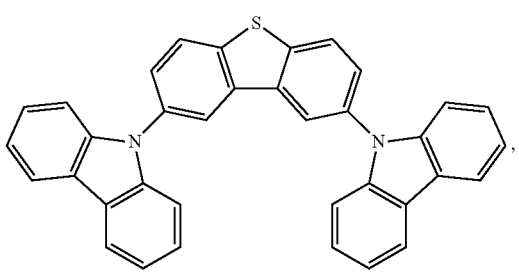

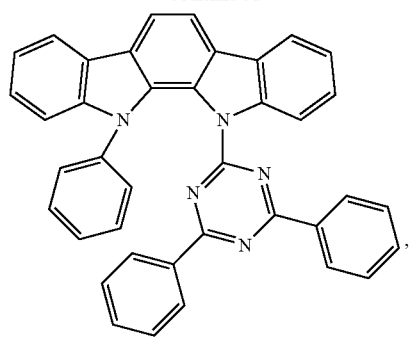
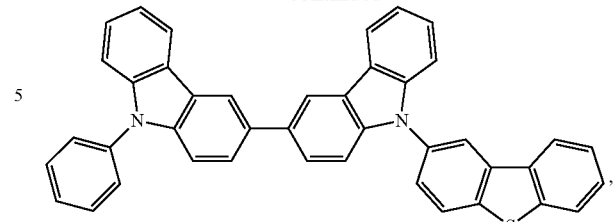
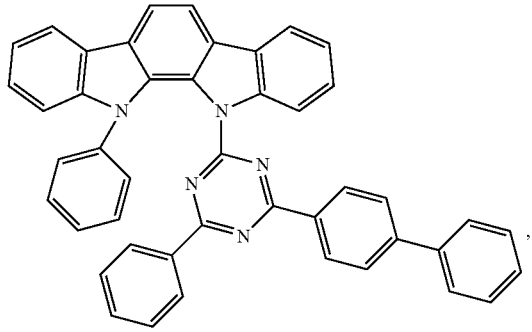
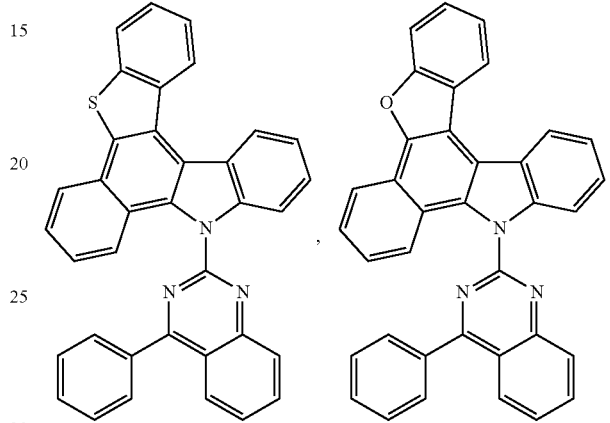
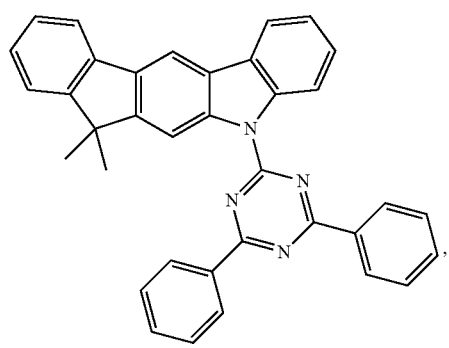
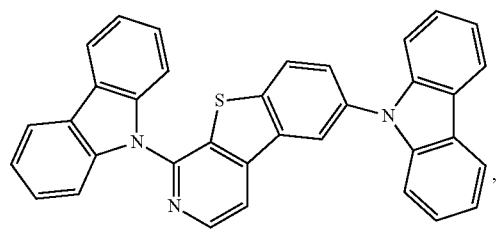
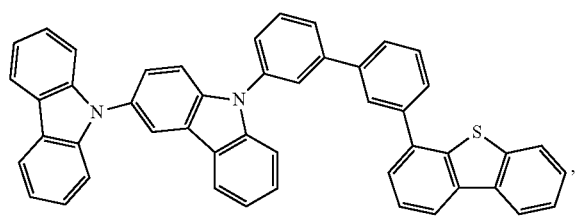
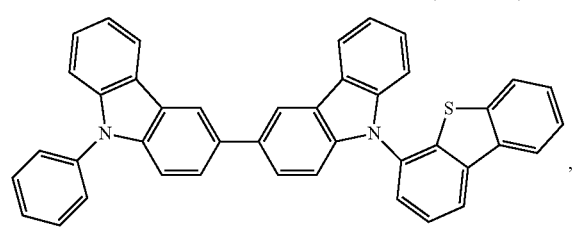

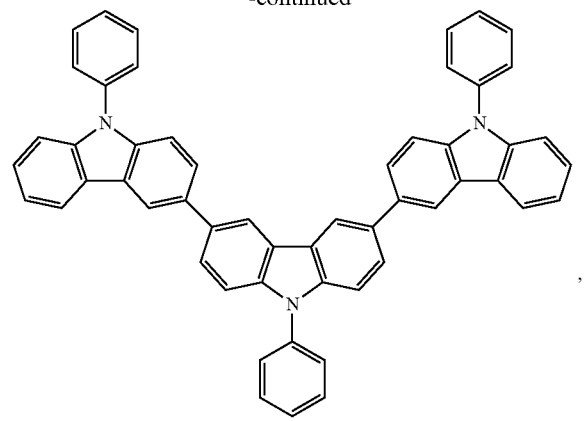
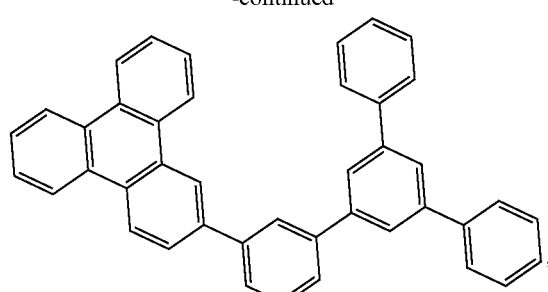
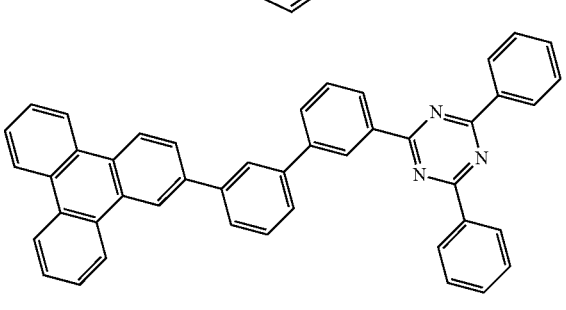
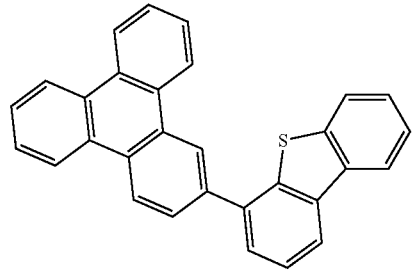
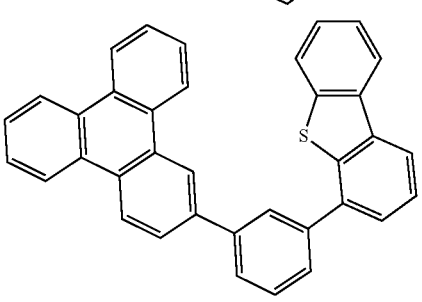
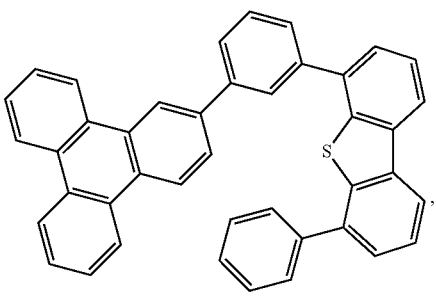
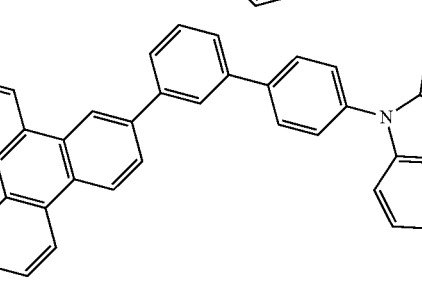

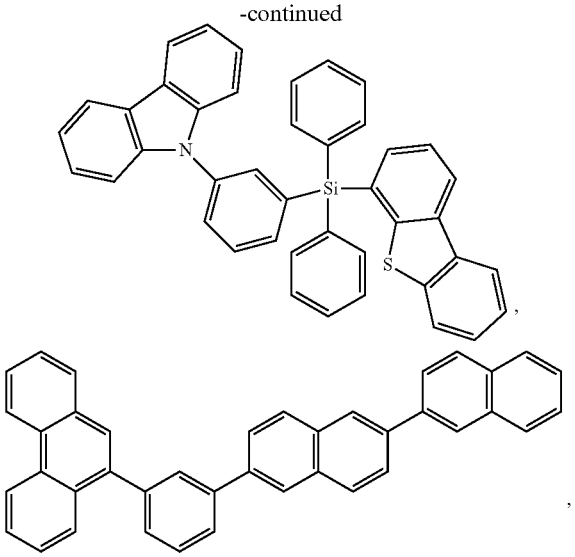

and combinations thereof.
Additional information on possible hosts is provided below.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO006081780, WO2009003455, WO2009008277, WO2009011327, WO2014009310, US2007252140, US2015060804, US20150123047, and US2012146012.

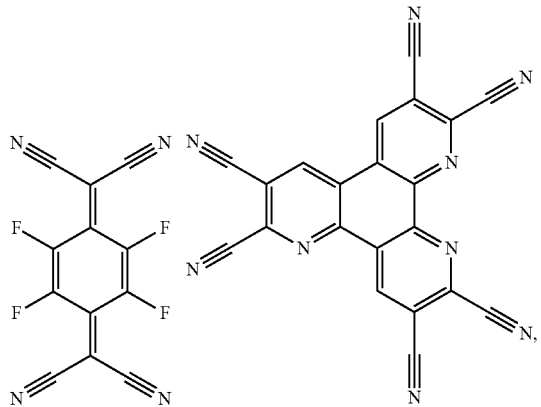

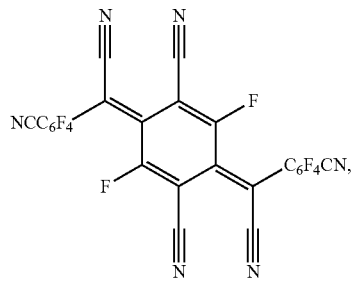

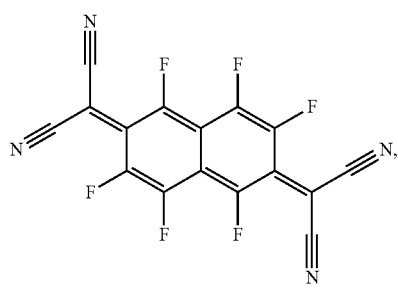

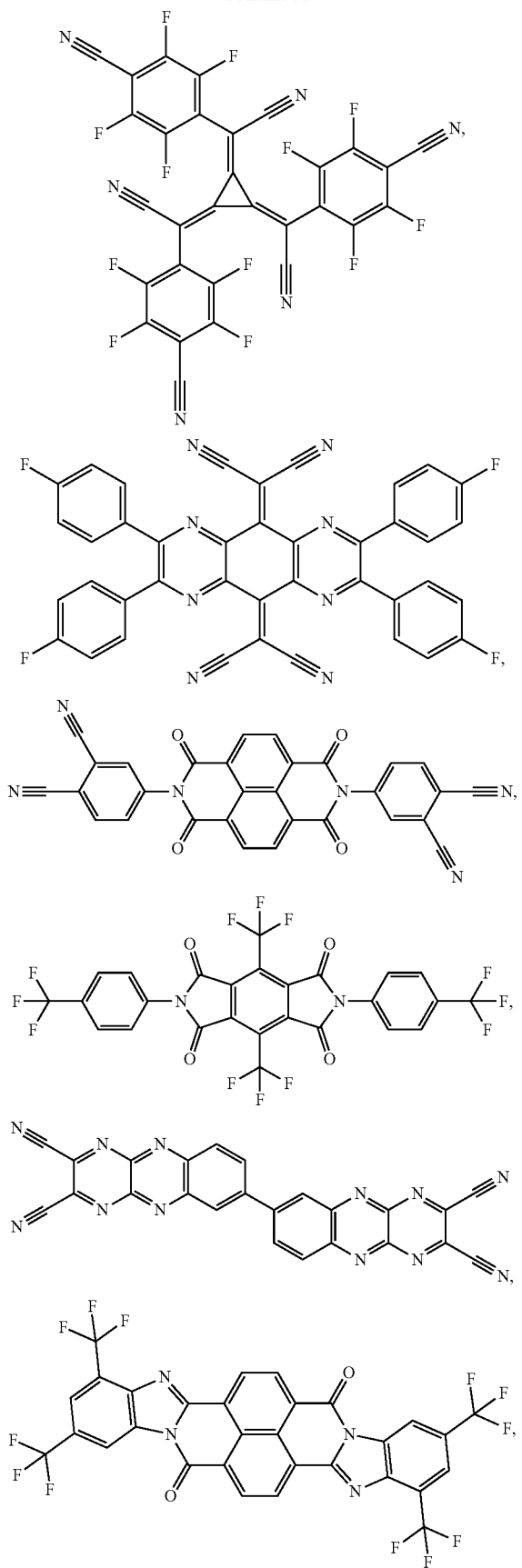

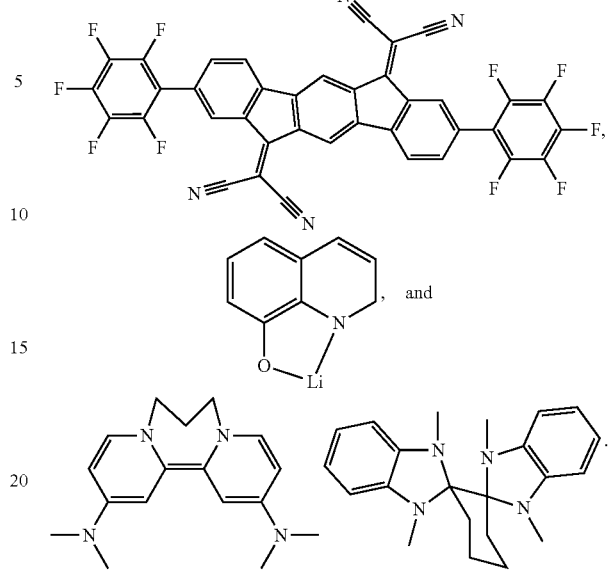

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

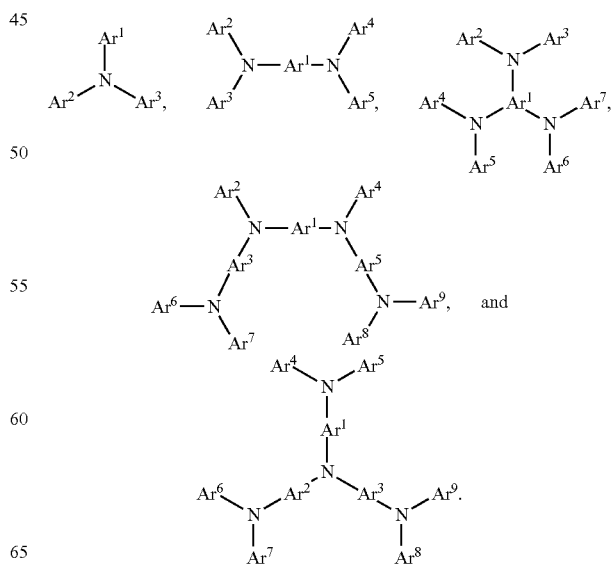

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

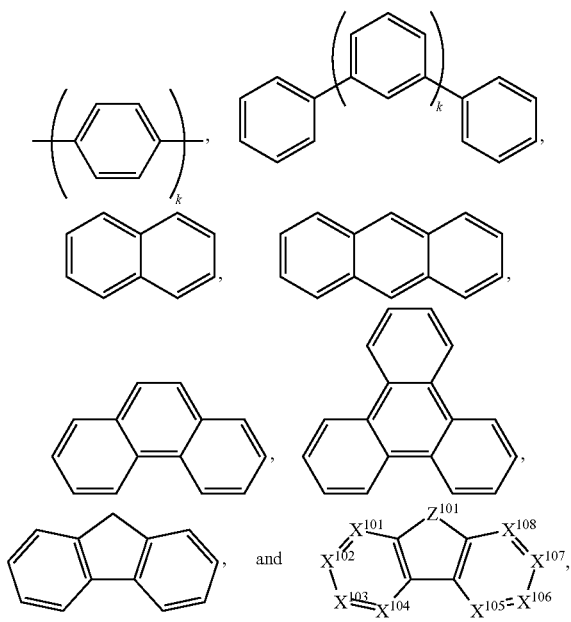

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

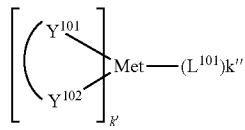

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k'' is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

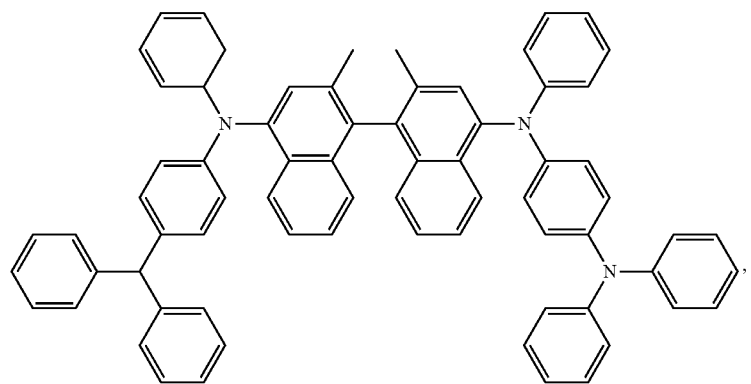
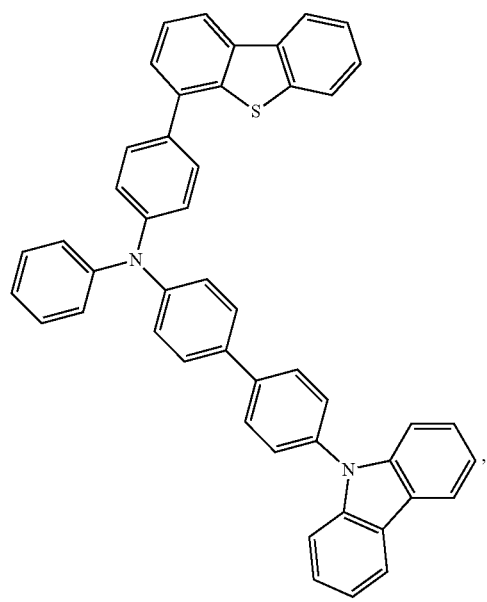
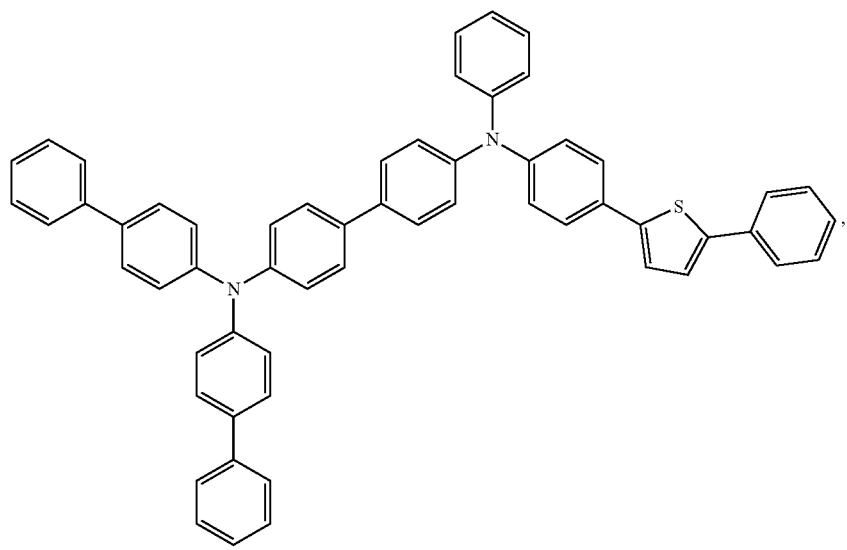

-continued
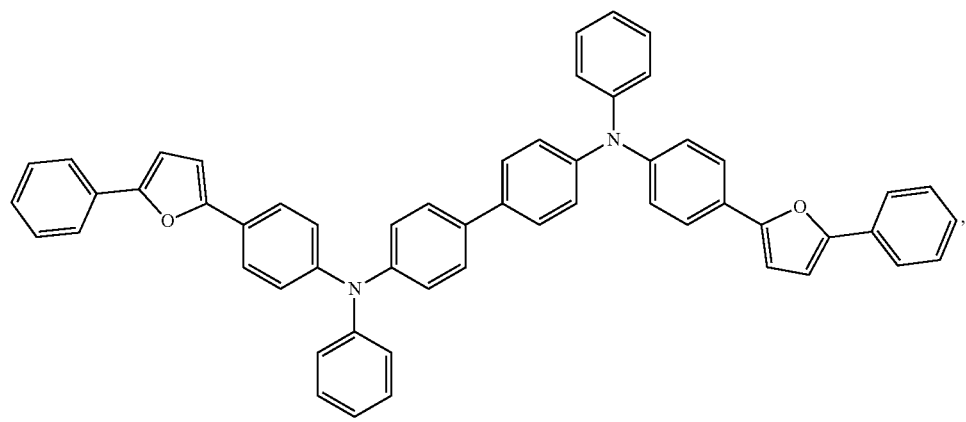
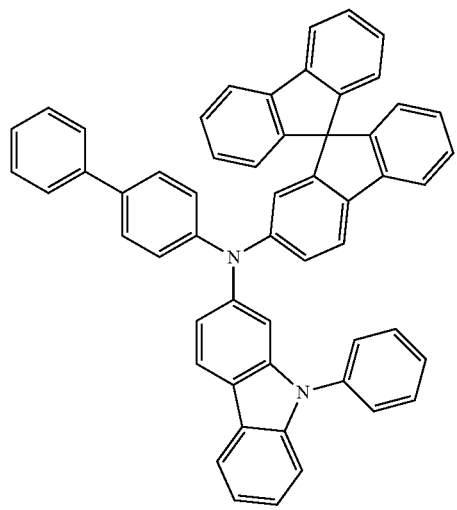
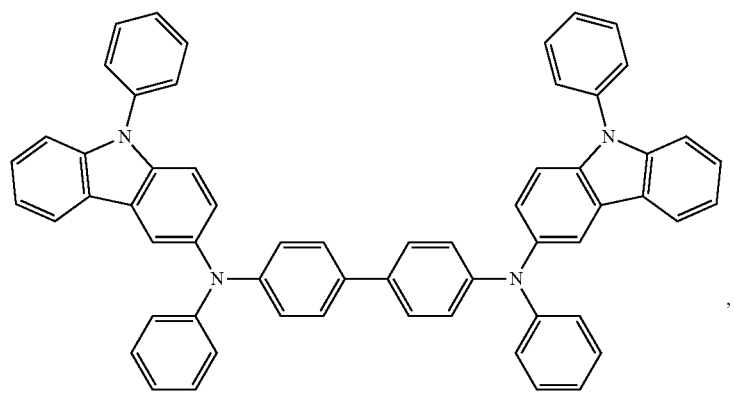

-continued
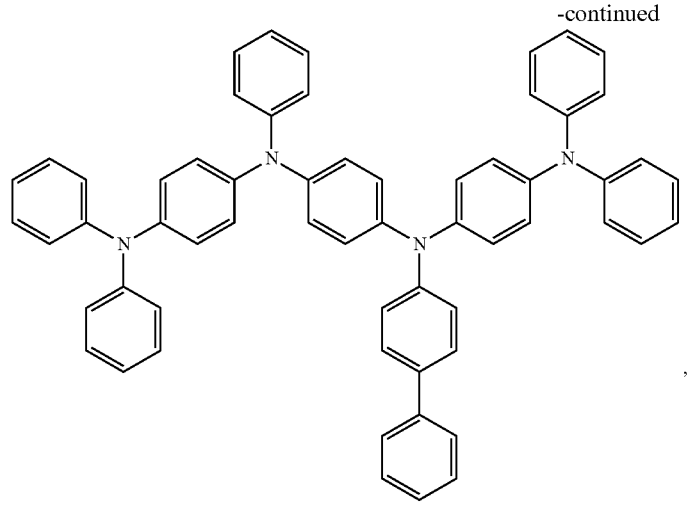
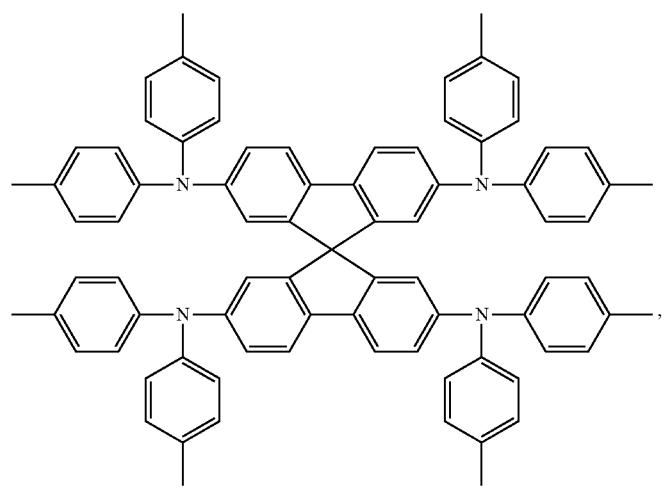
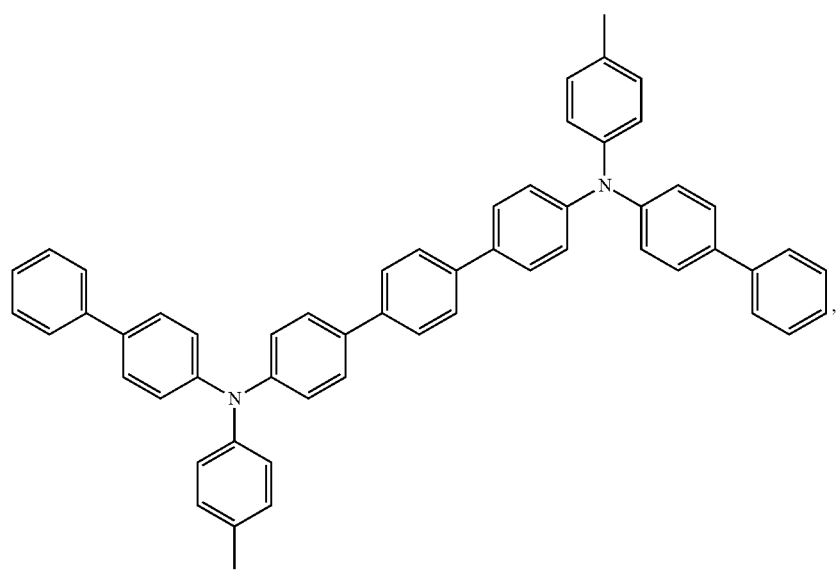

-continued
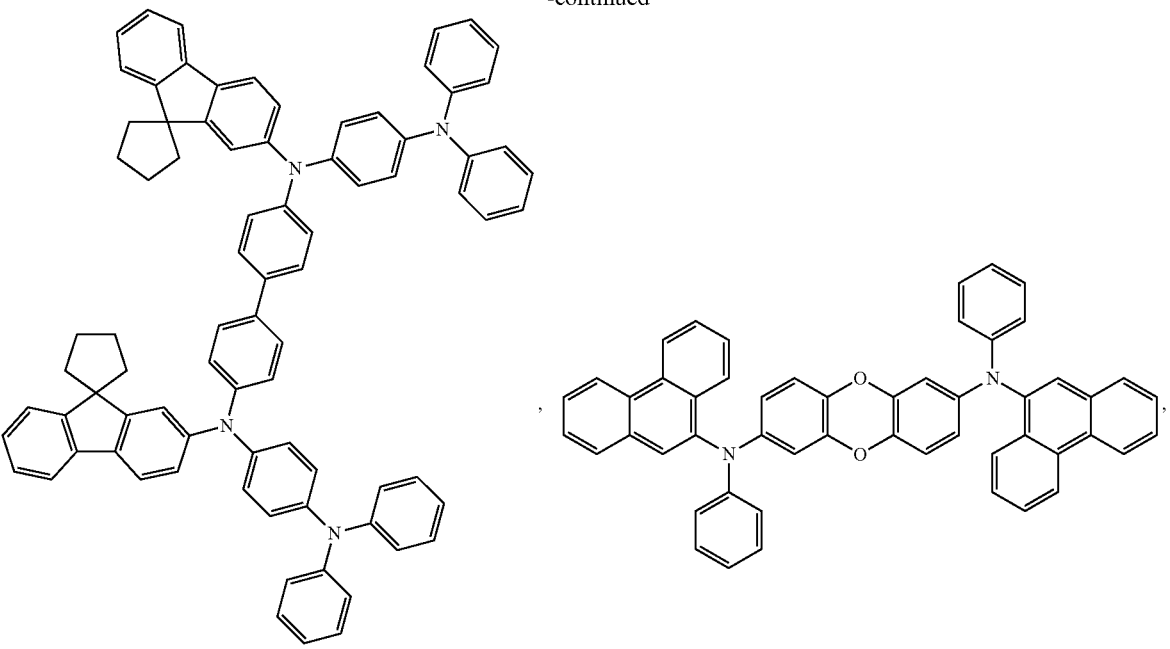
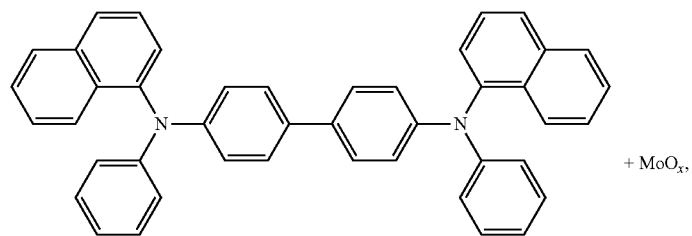
+ MoO$_x$,
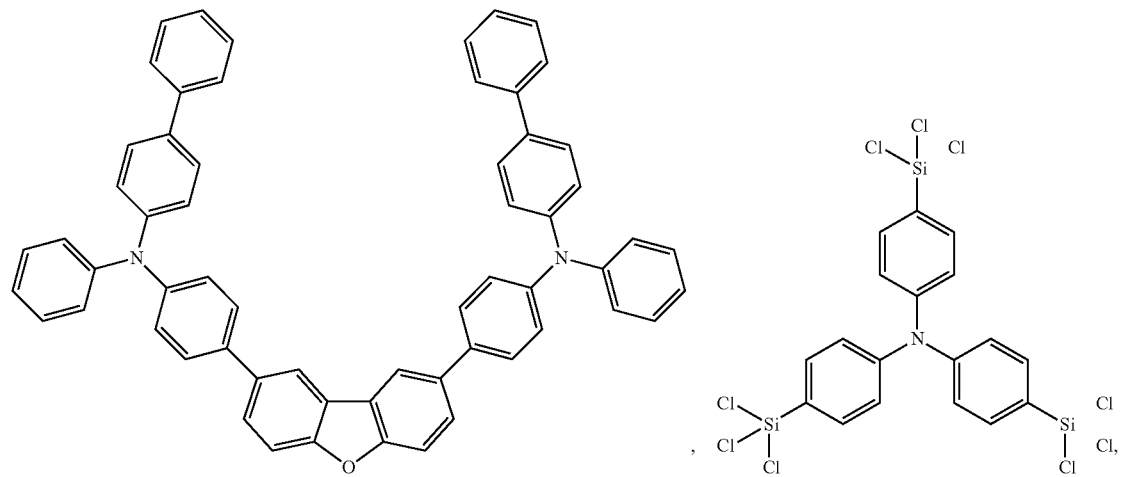

-continued
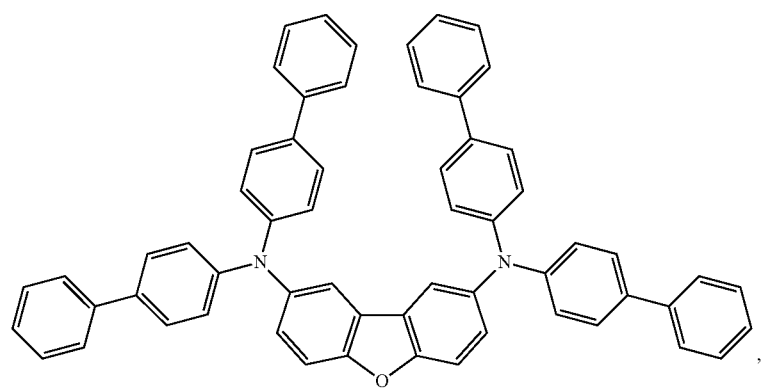 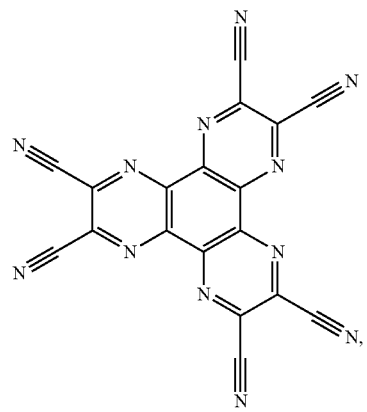
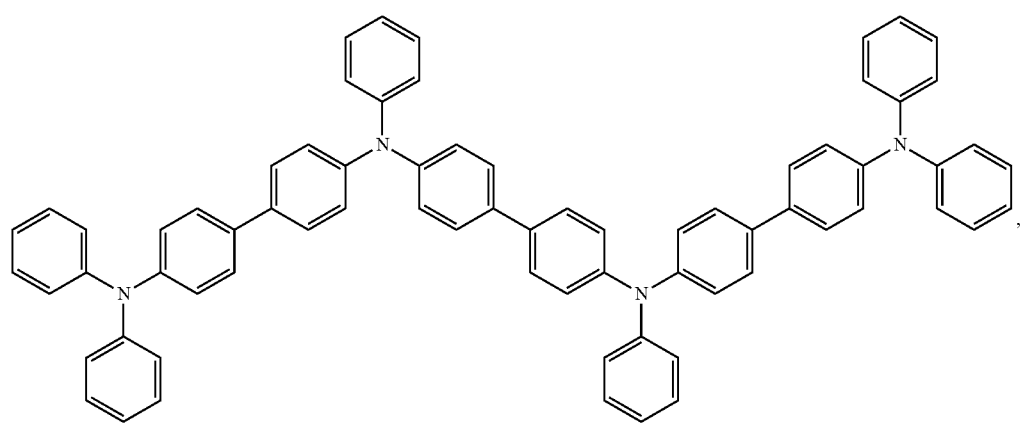
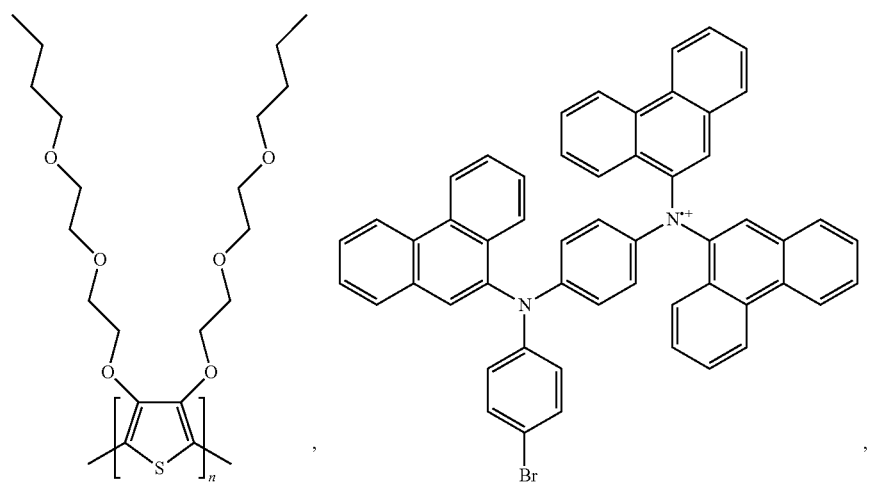

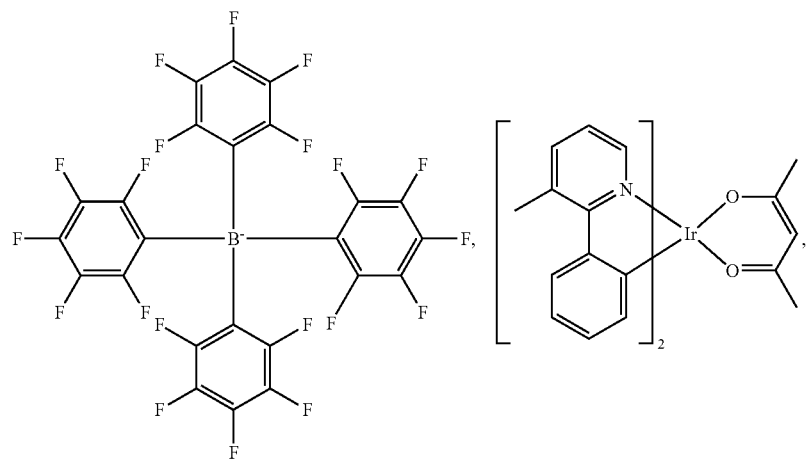
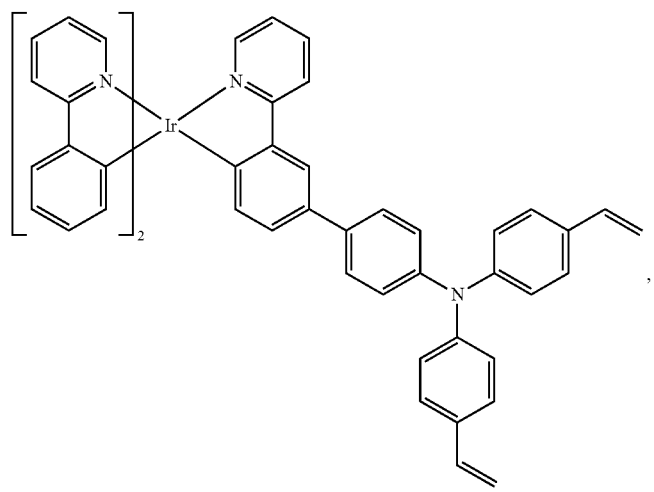
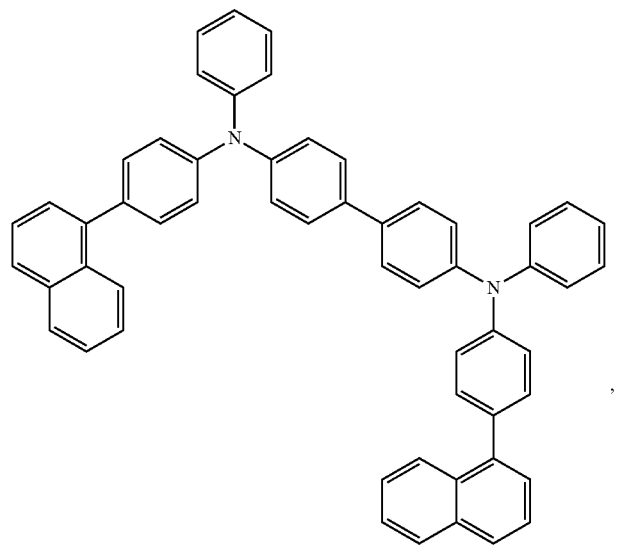

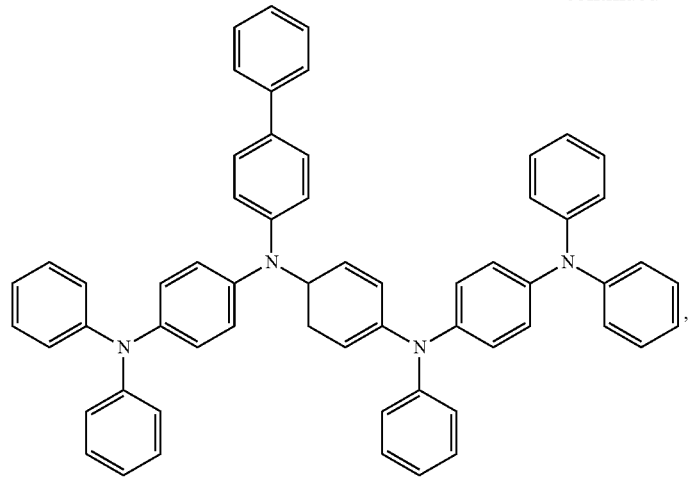
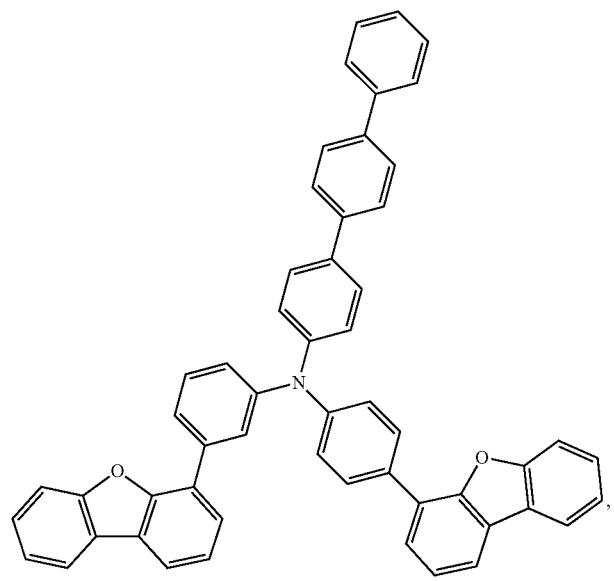
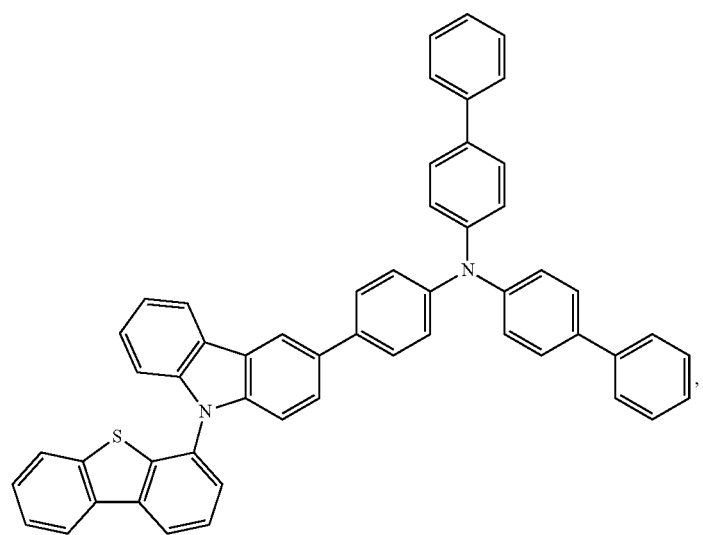

-continued
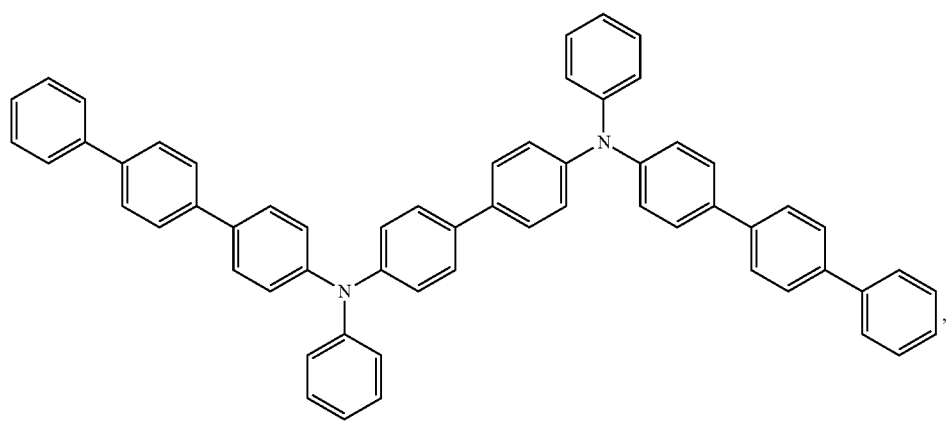
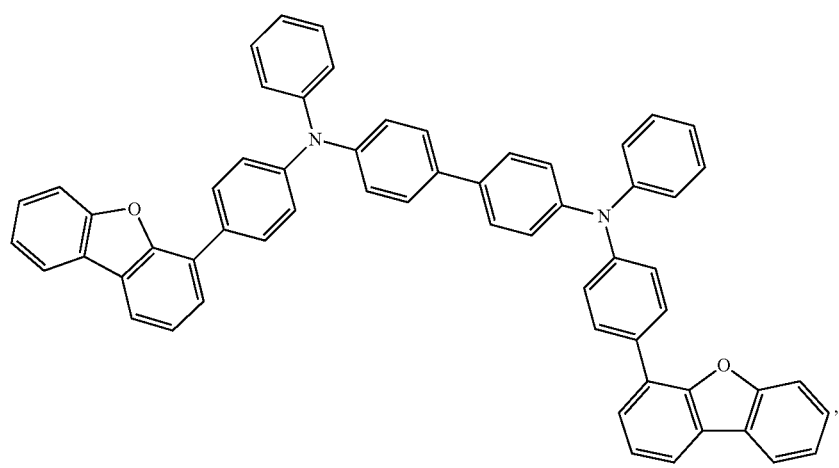
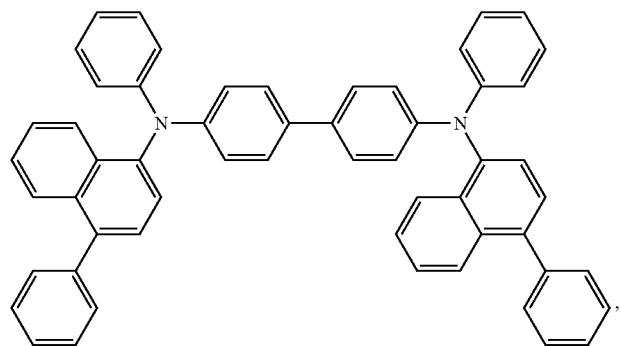

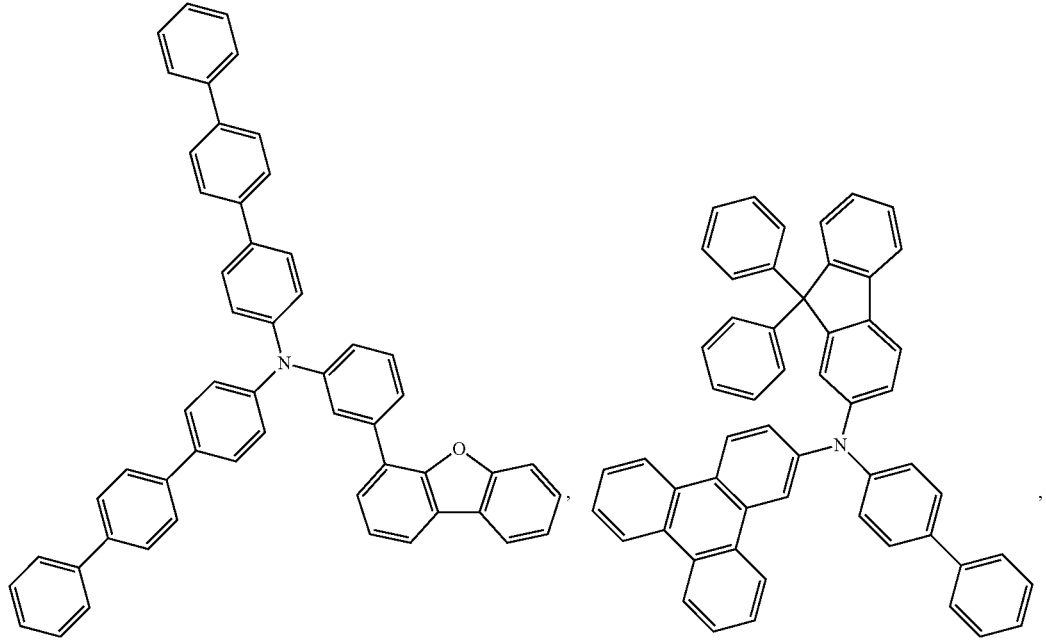
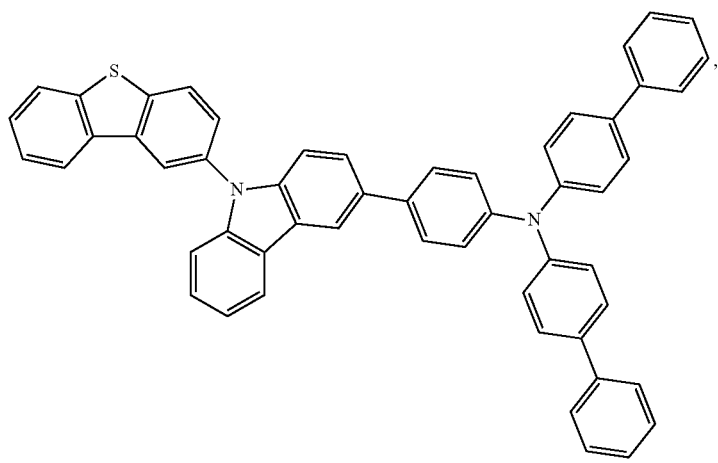
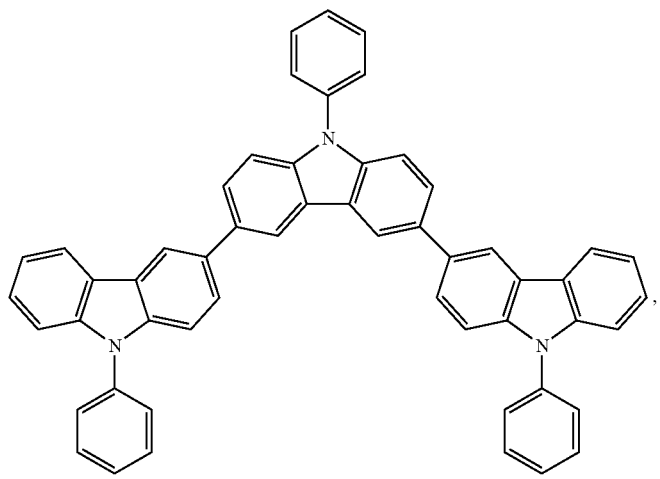

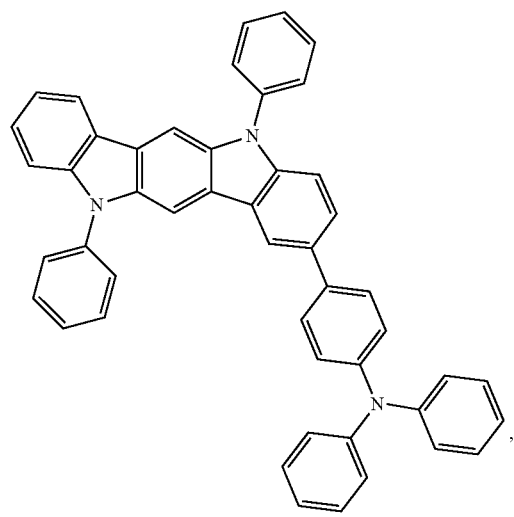
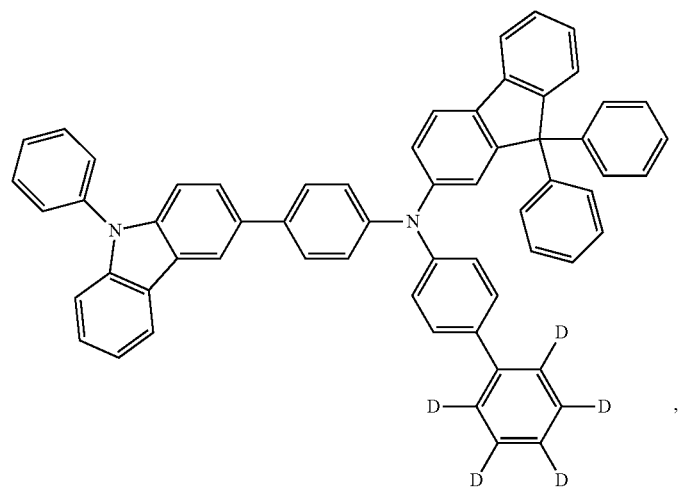
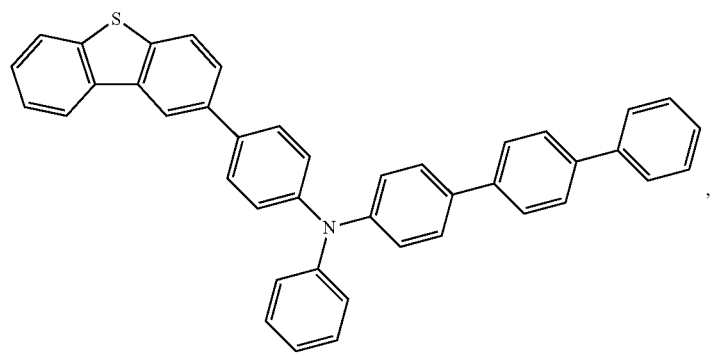
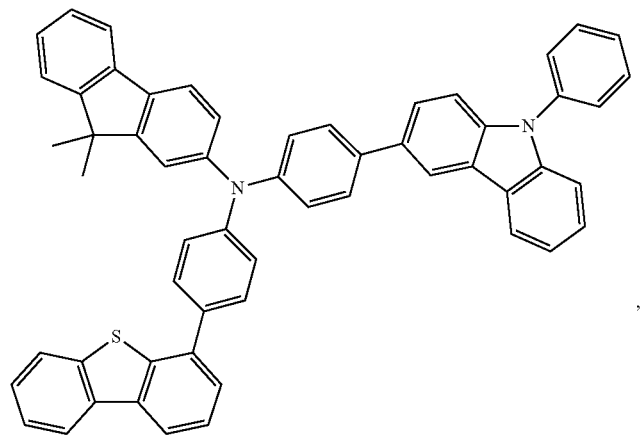

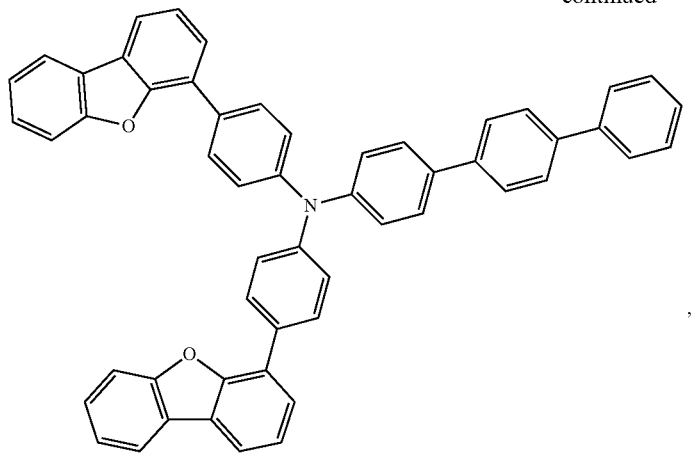
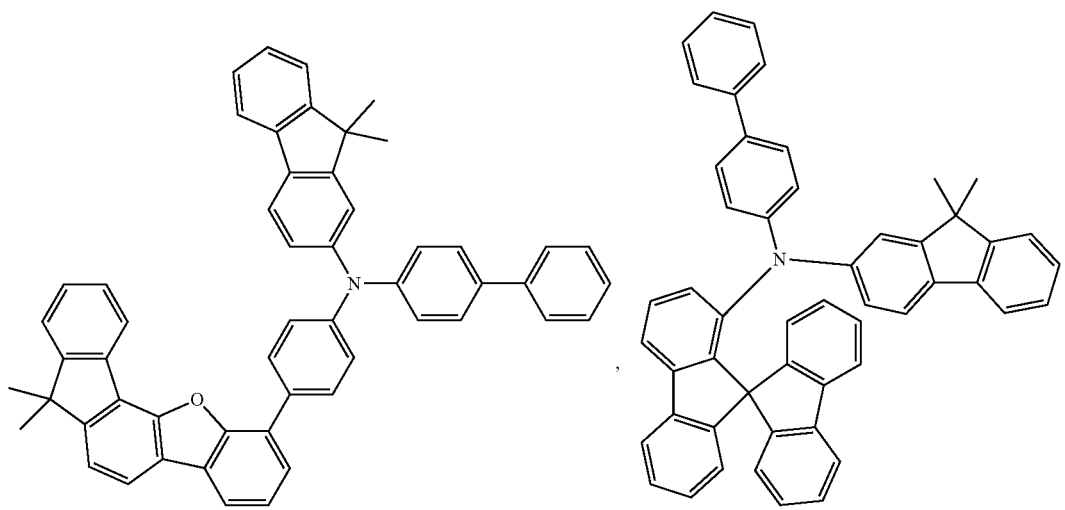
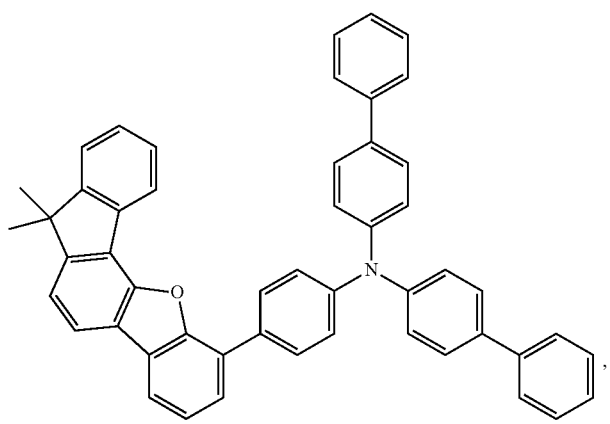

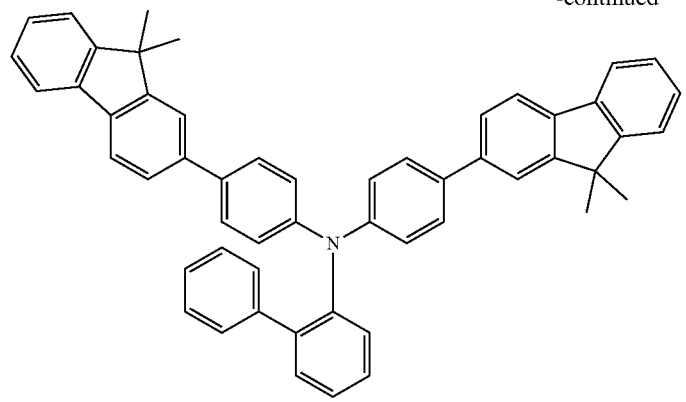
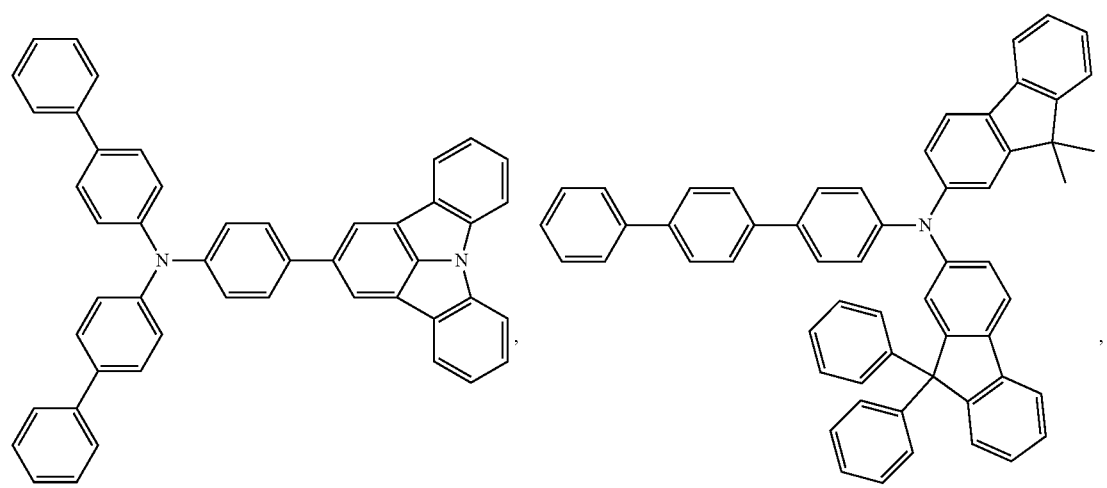
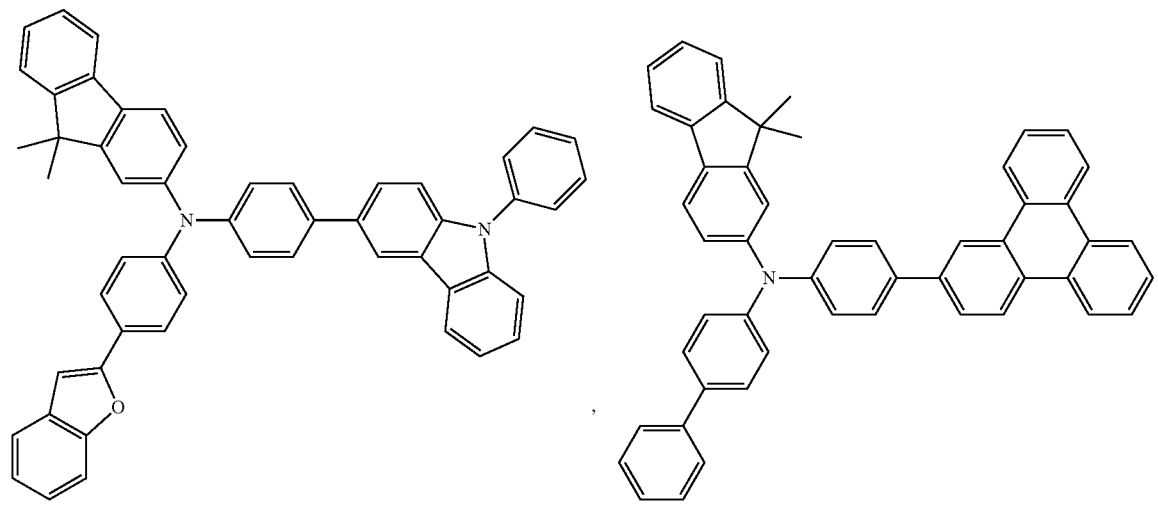

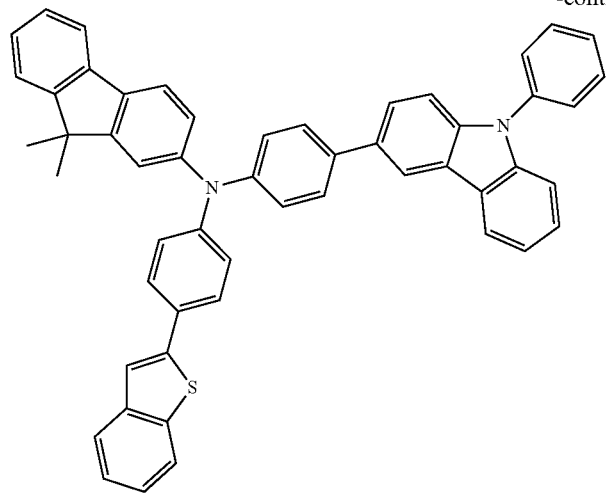
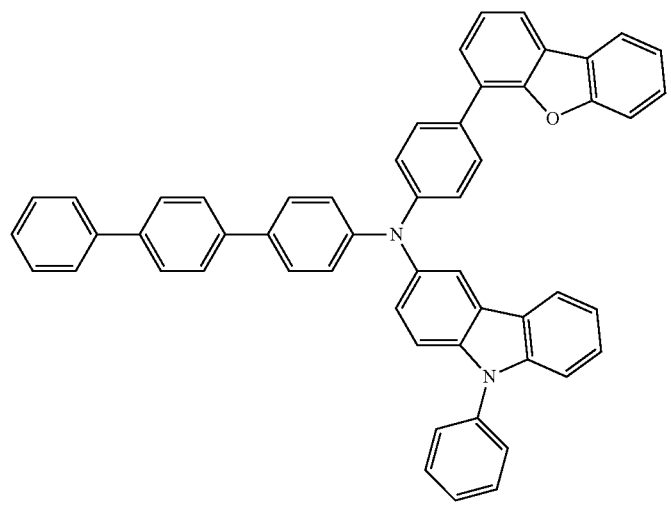
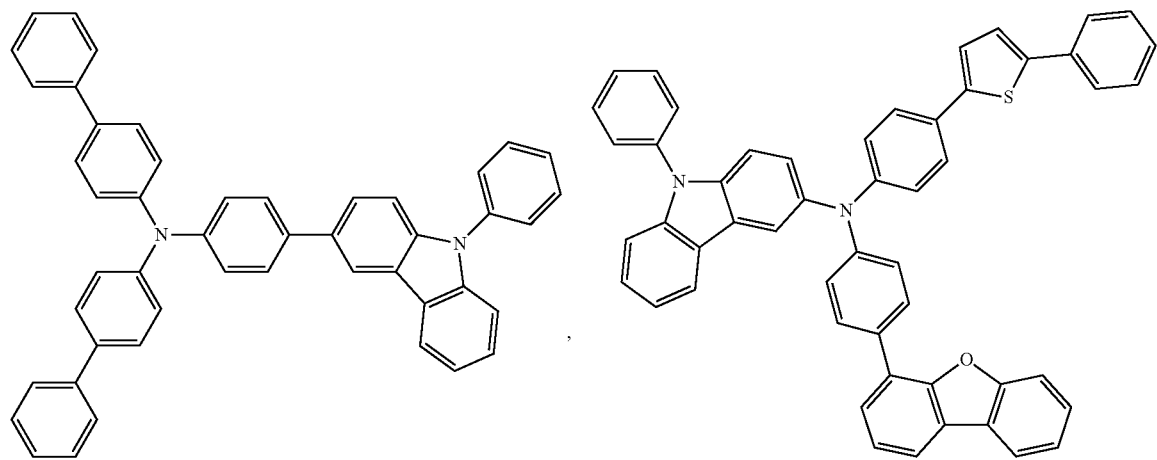

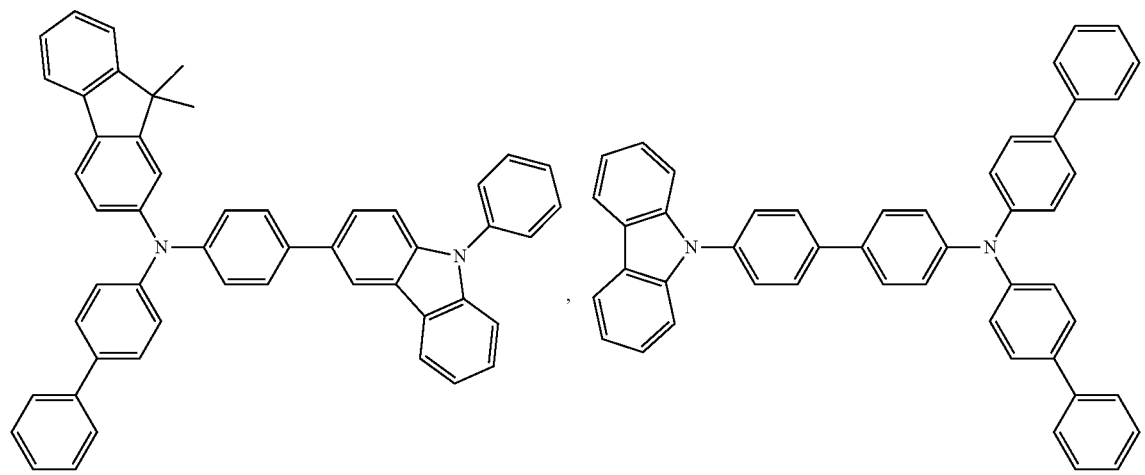
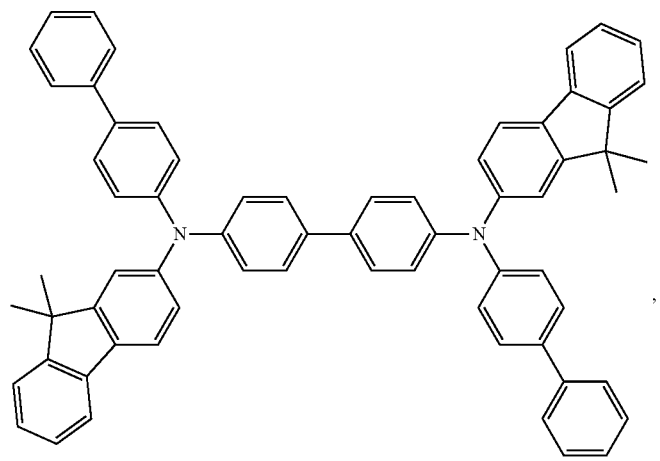
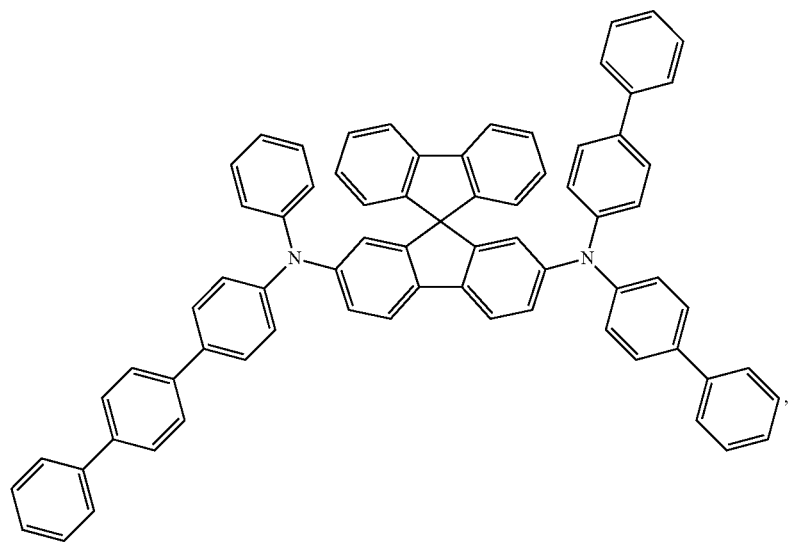

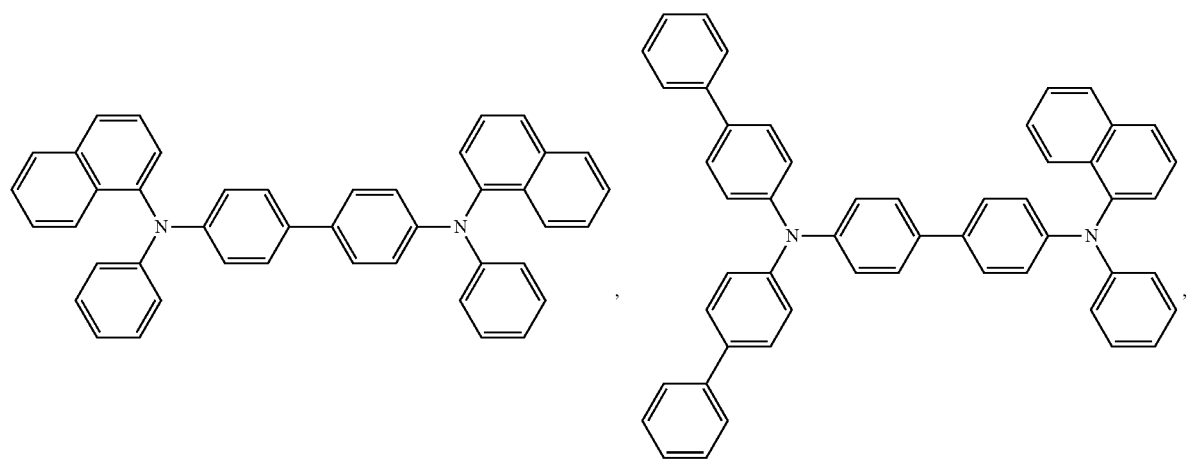
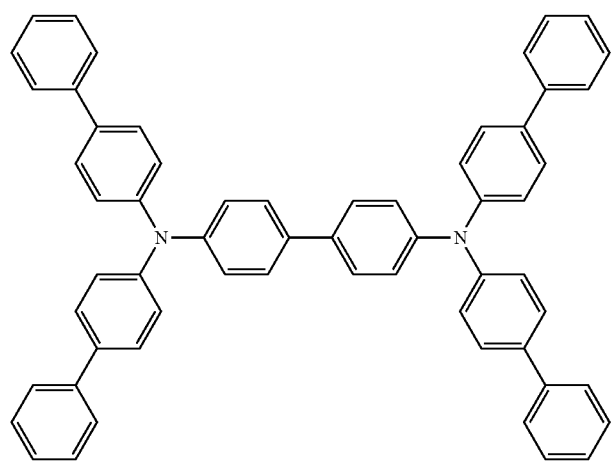
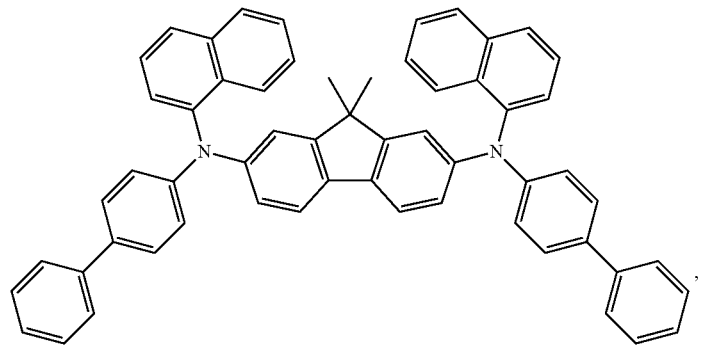

-continued
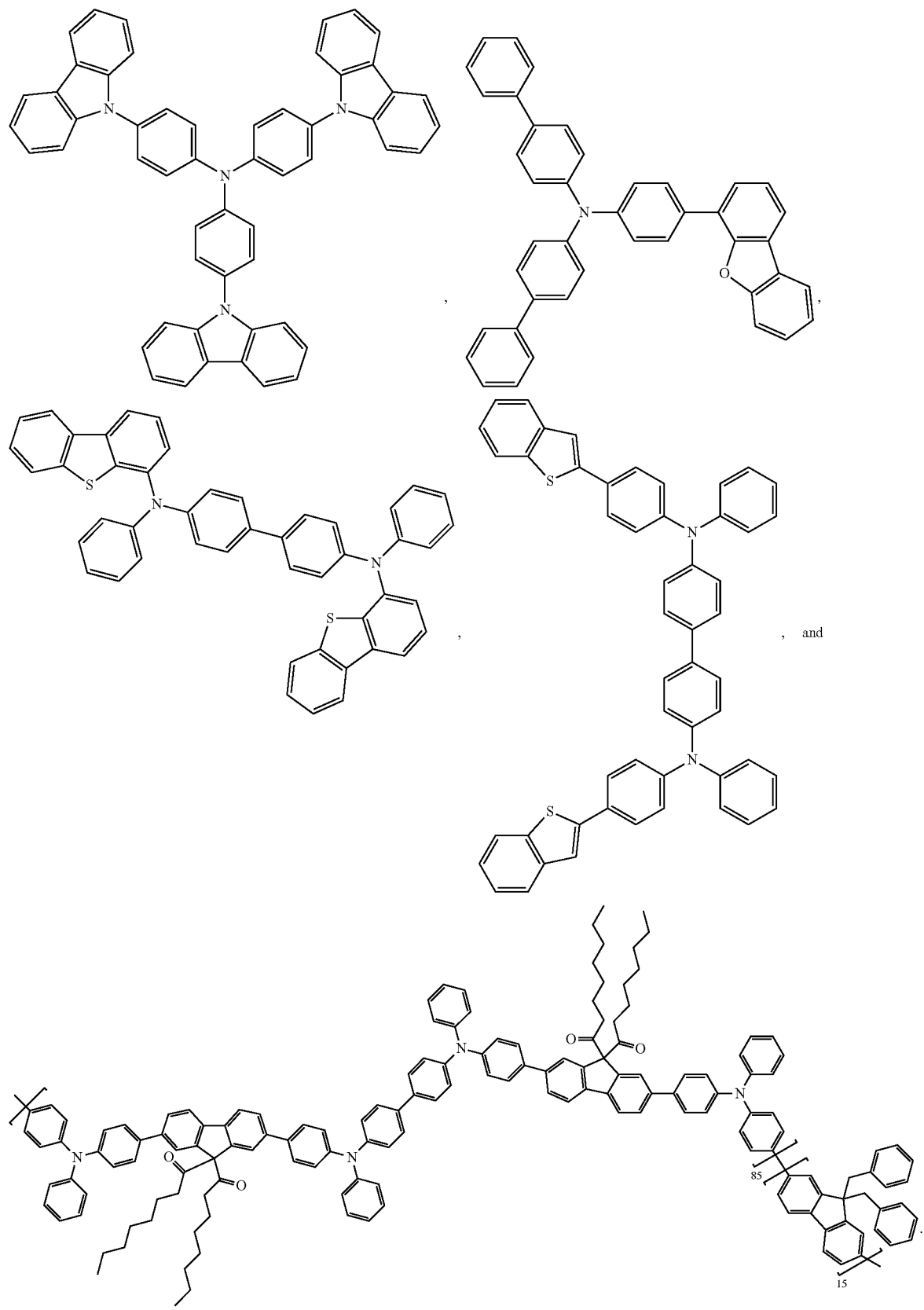

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

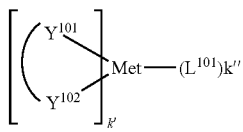

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k'' is the maximum number of ligands that may be attached to the metal.

In one aspect, the metal complexes are:

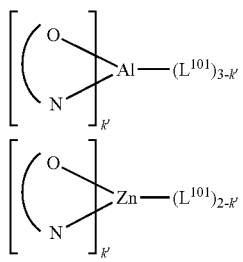

wherein (O—N) is a bidentate ligand, having metal coordinated to atoms O and N.

In another aspect, Met is selected from Ir and Pt. In a further aspect, $(Y^{103}-Y^{104})$ is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

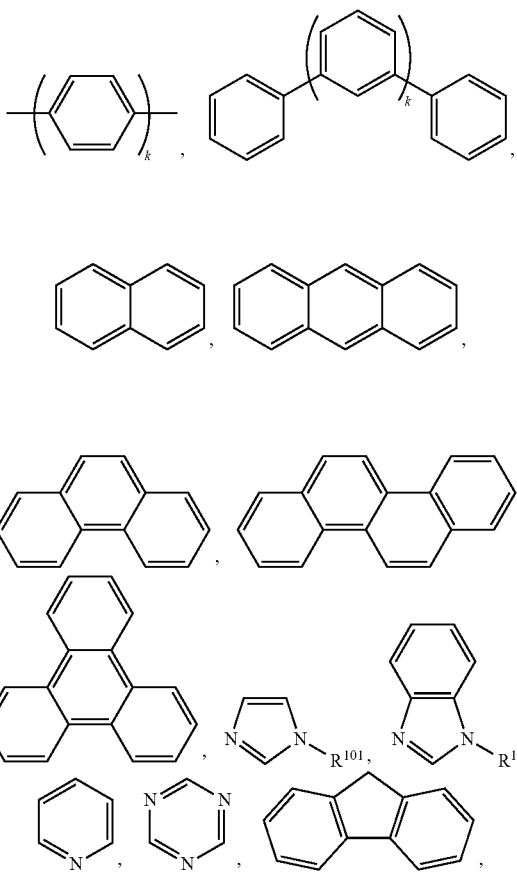

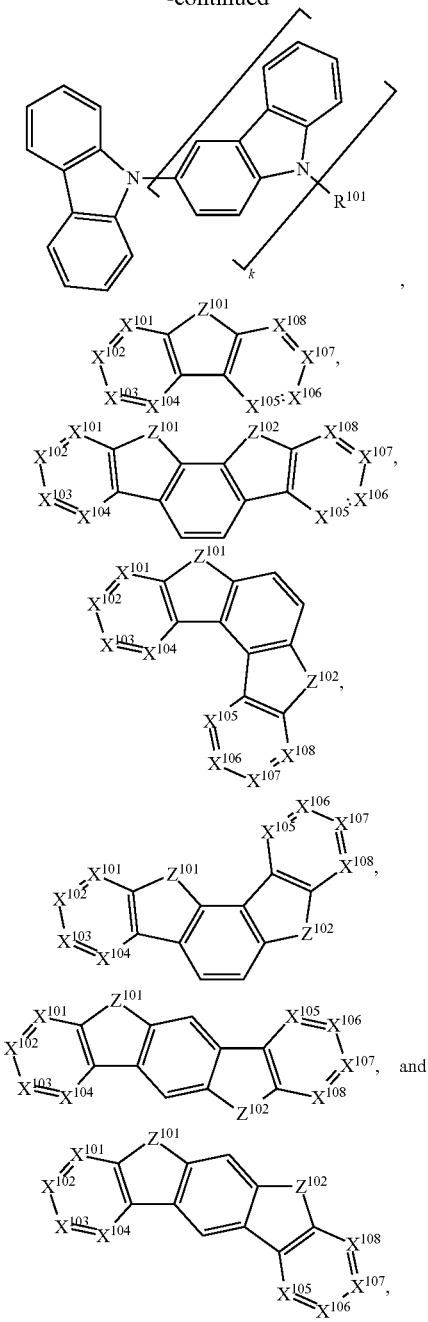

wherein R[101] is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

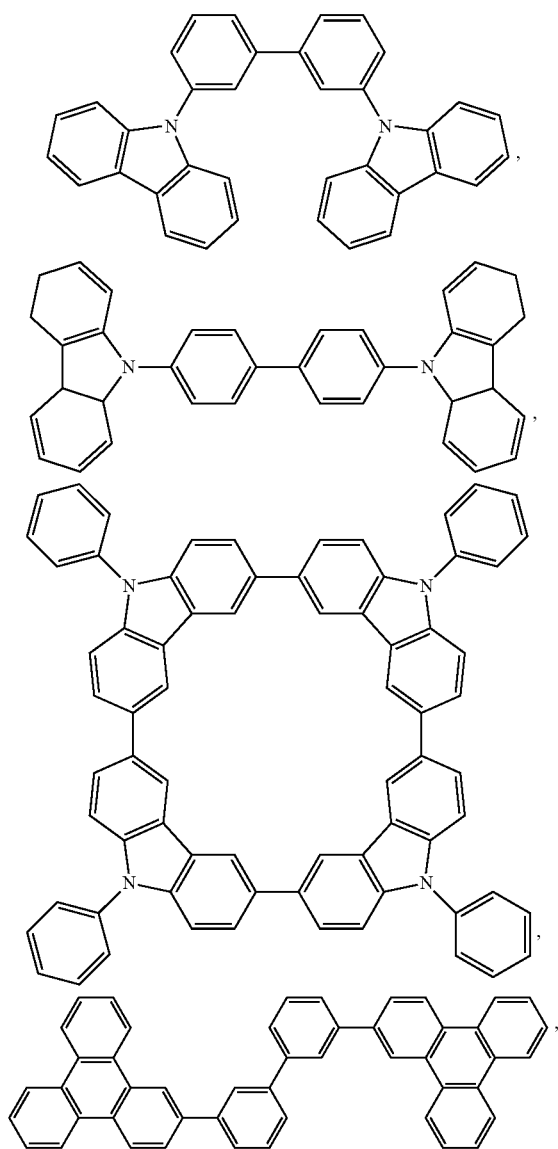

-continued
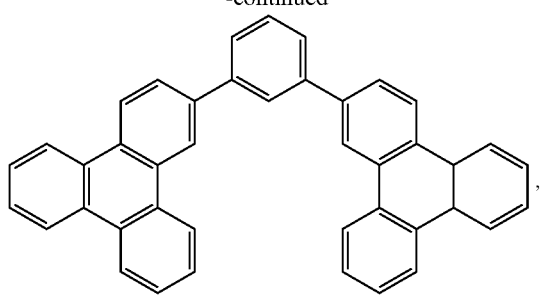
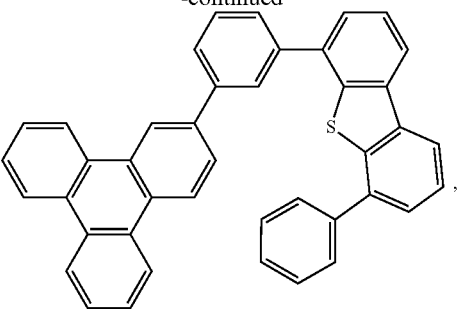

75
-continued
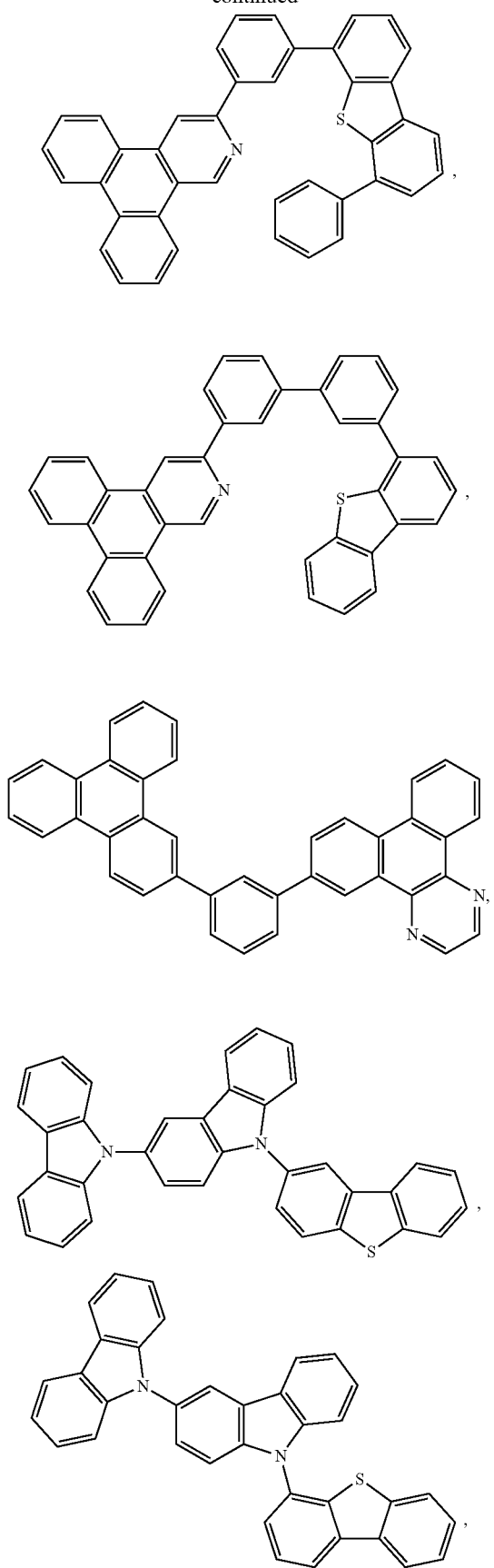
76
-continued
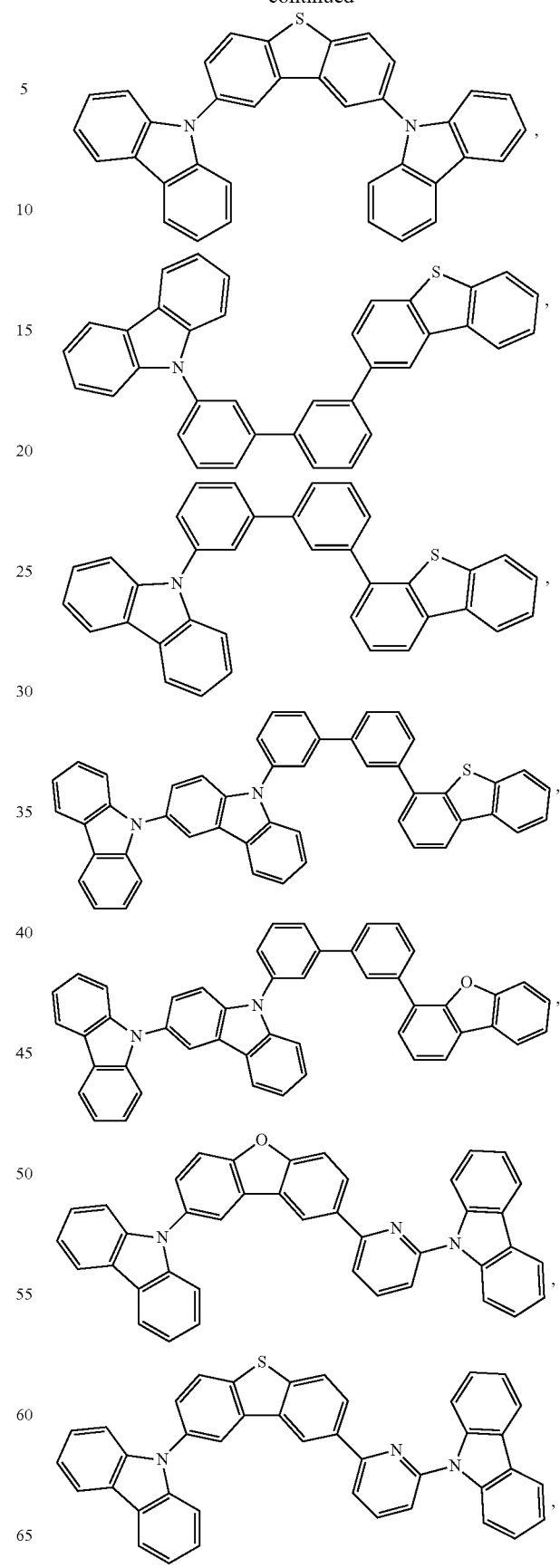

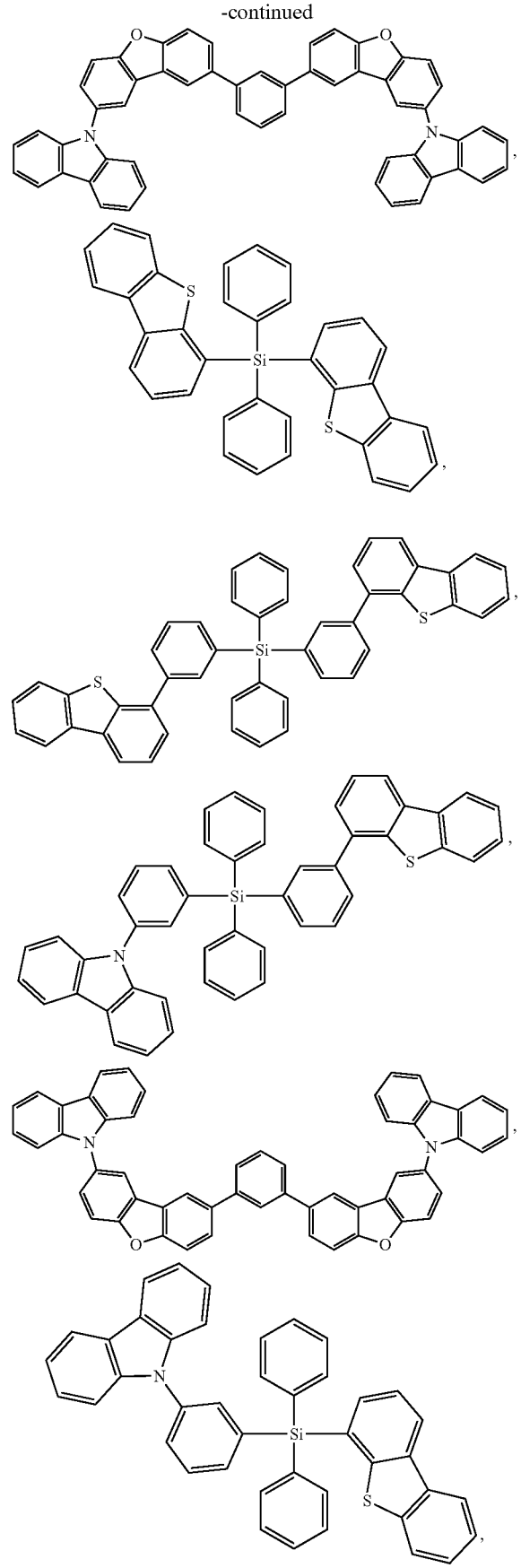
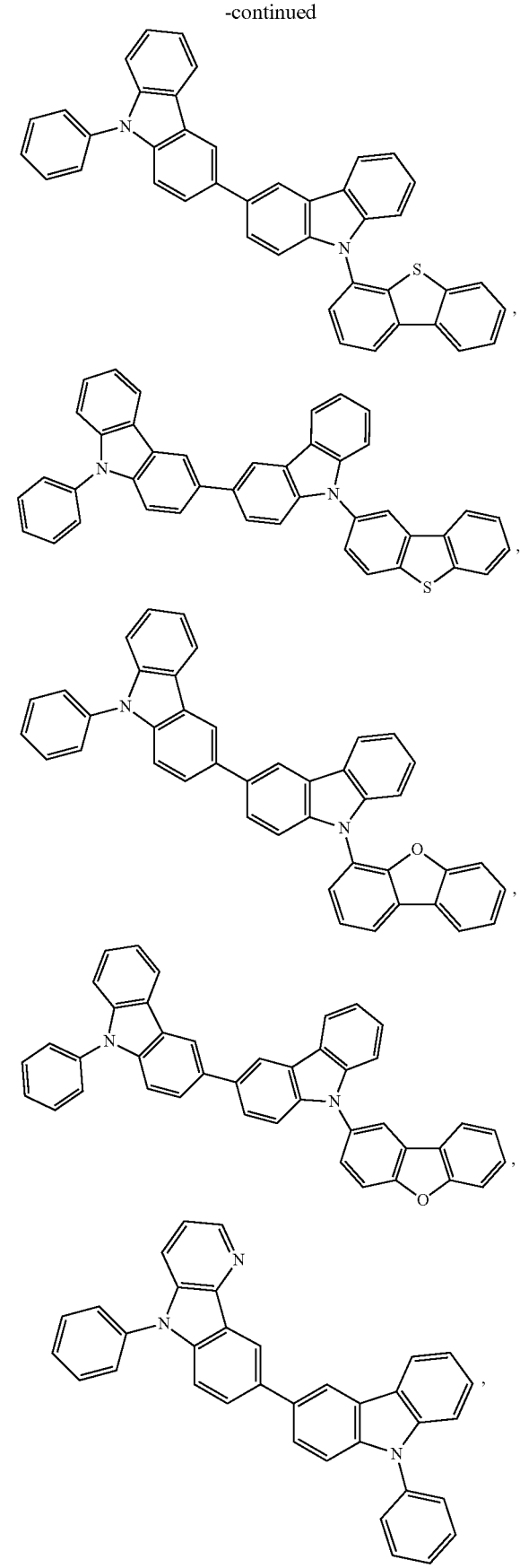

-continued
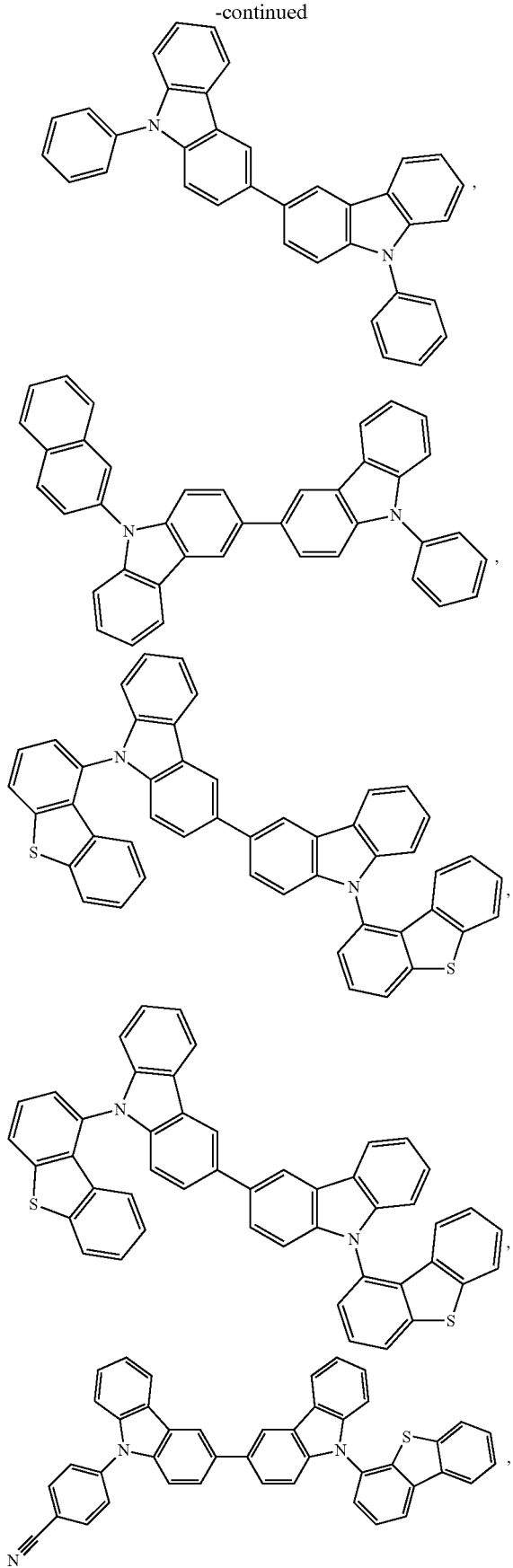
-continued
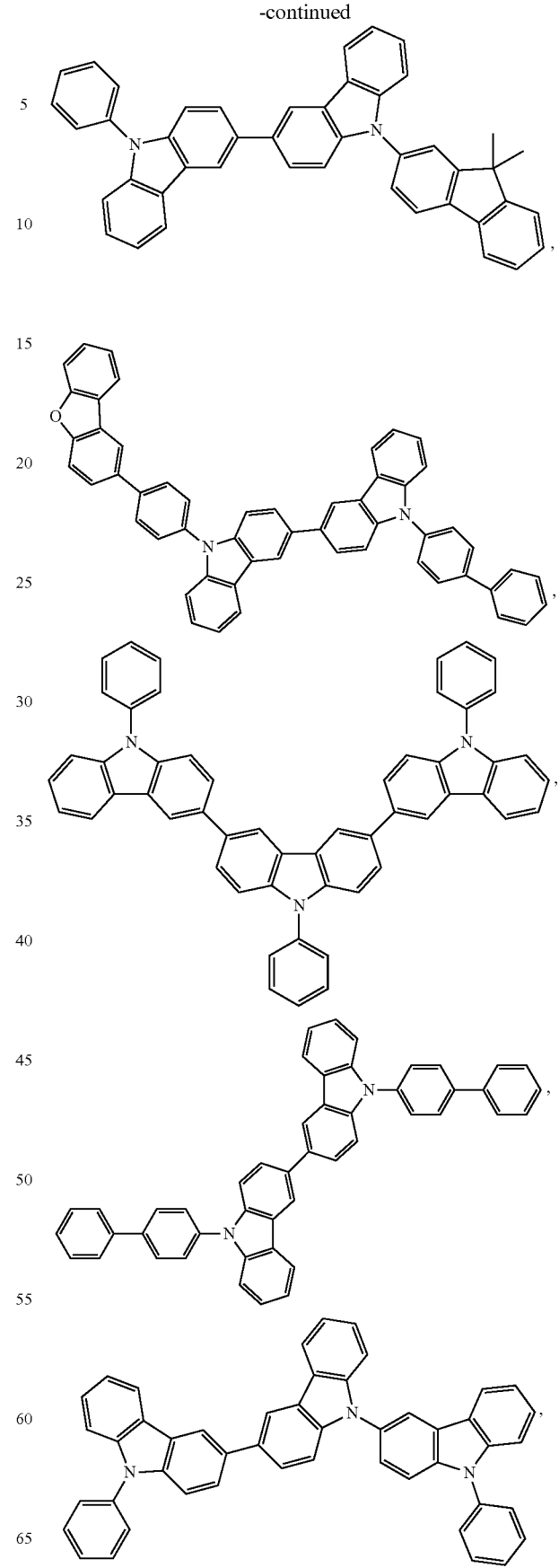

81
-continued
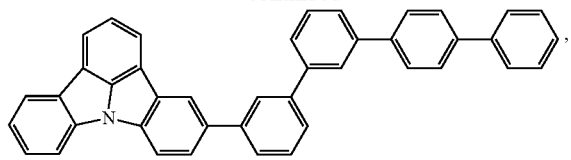
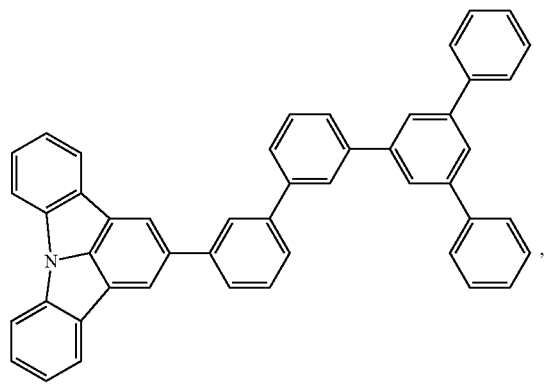
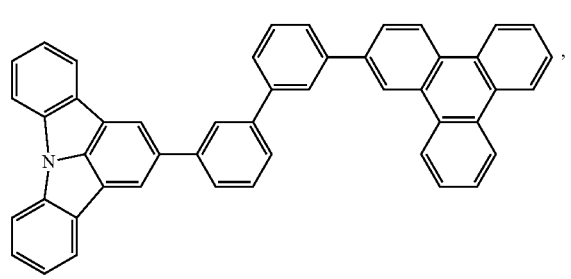
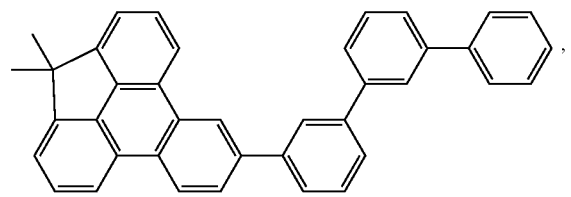
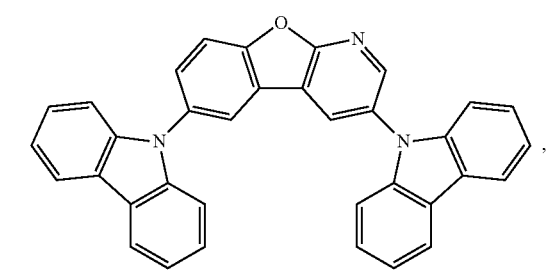
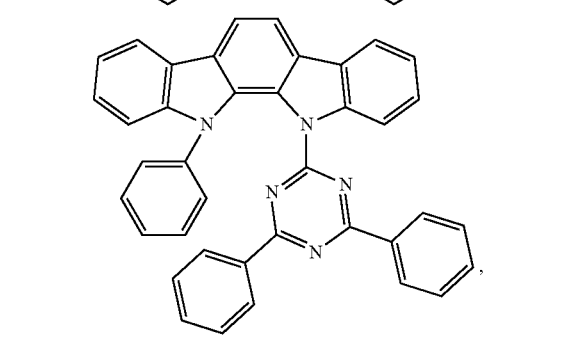
82
-continued
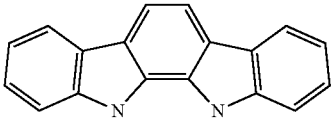
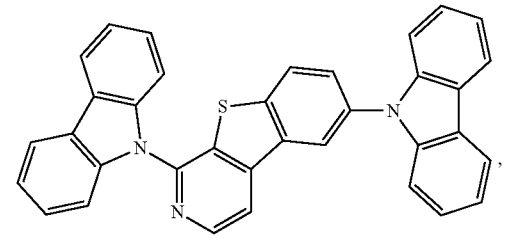
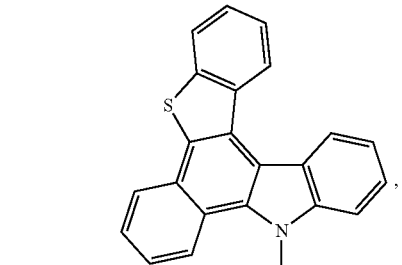
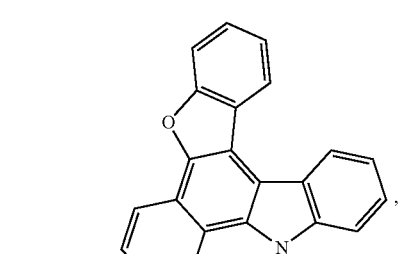
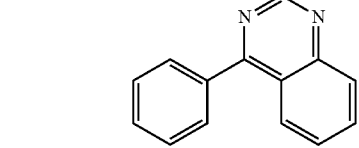

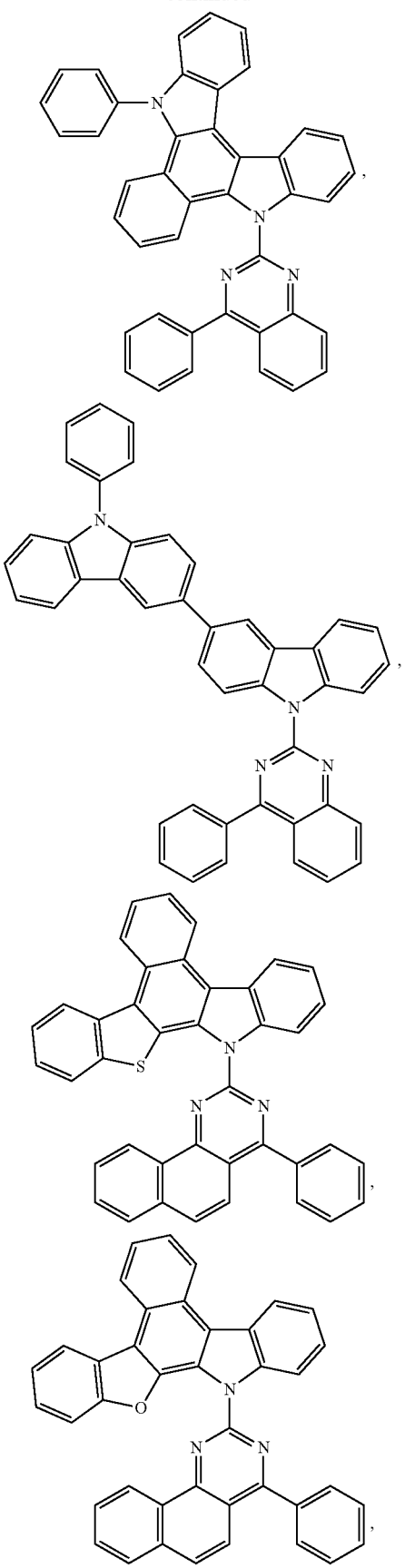
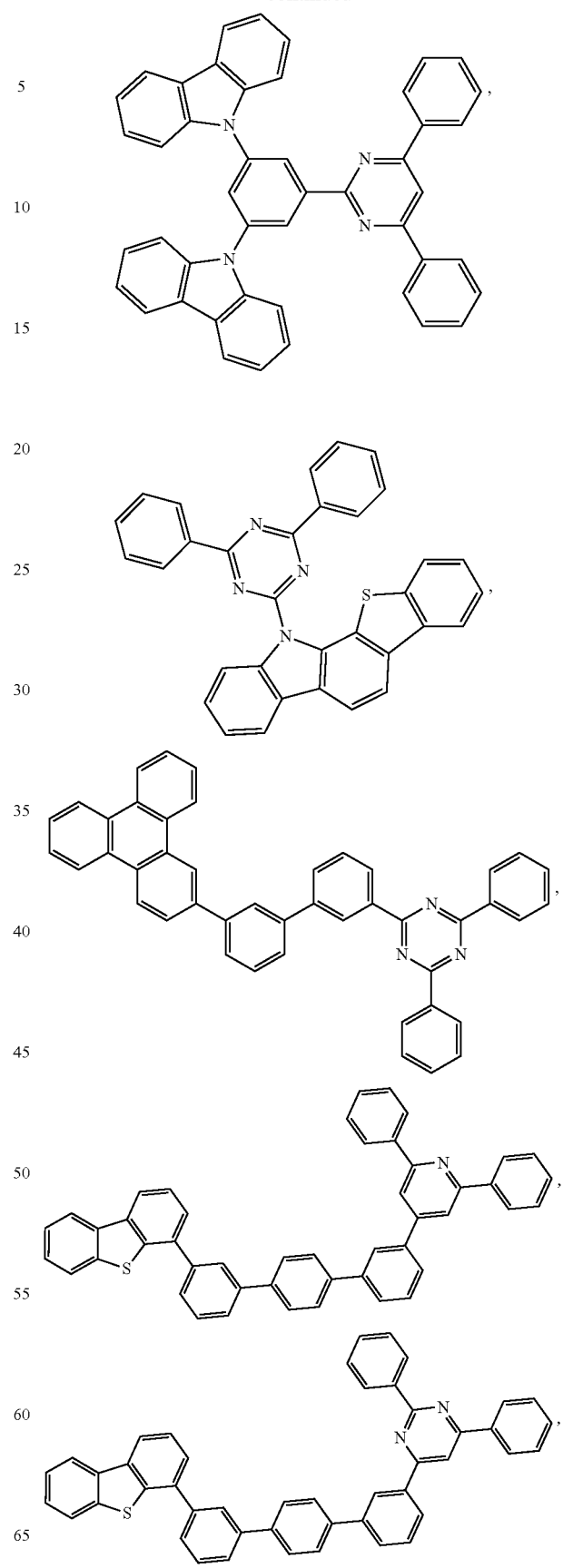

85
-continued

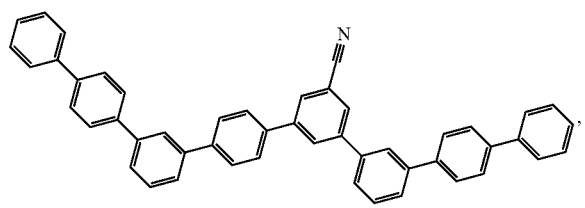,

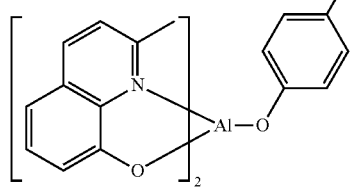,

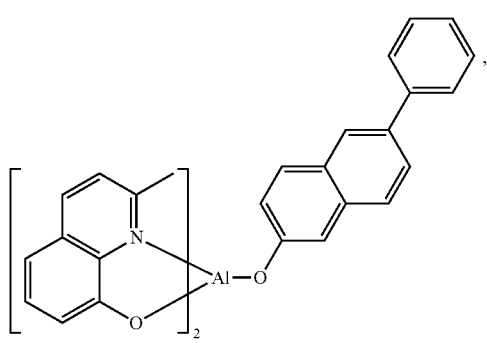,

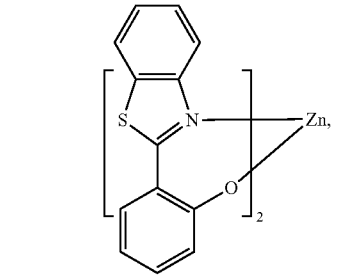,

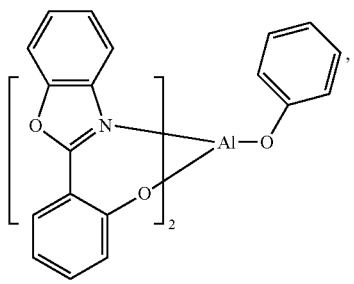,

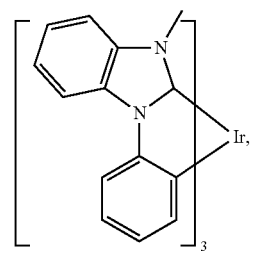

86
-continued

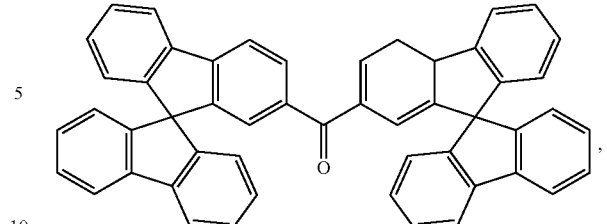,

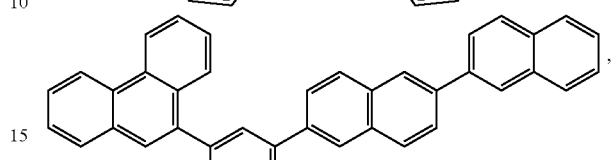,

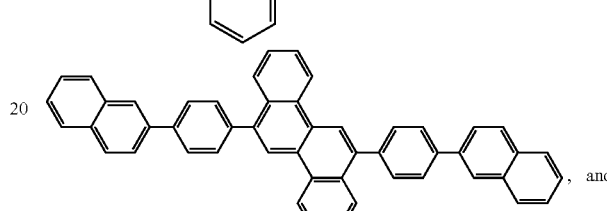, and

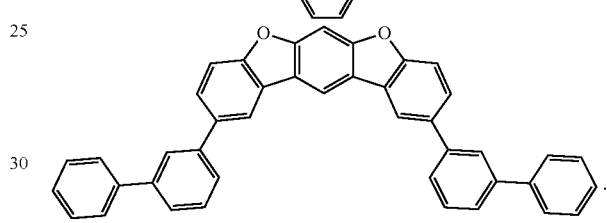.

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.
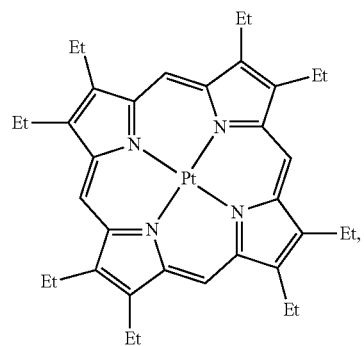
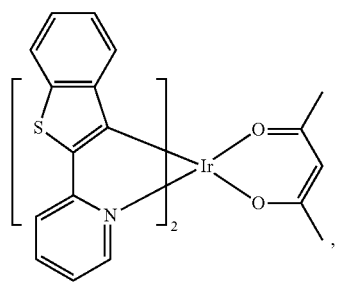
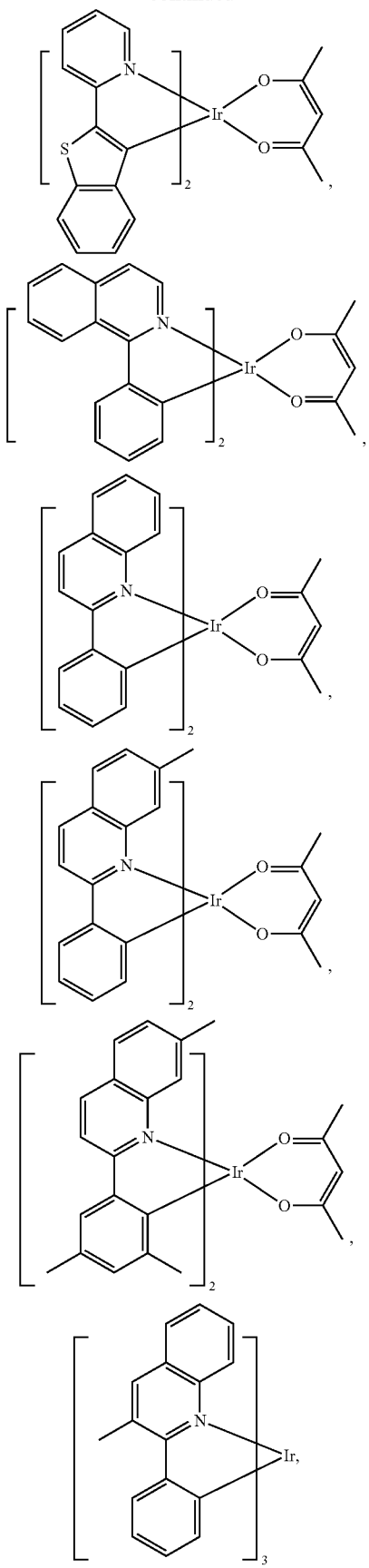

-continued
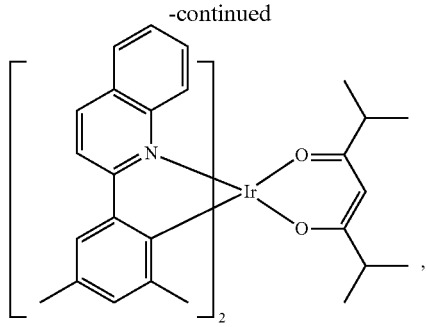
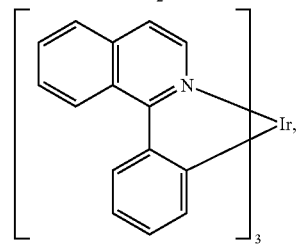
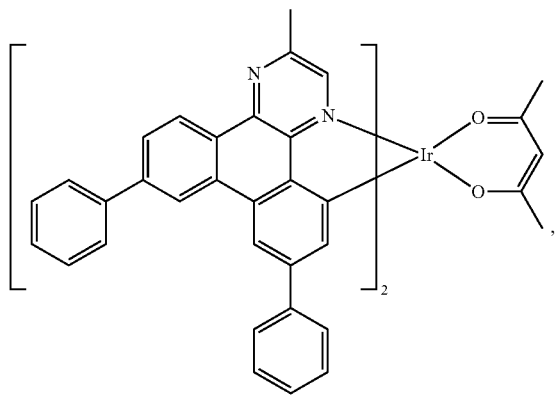
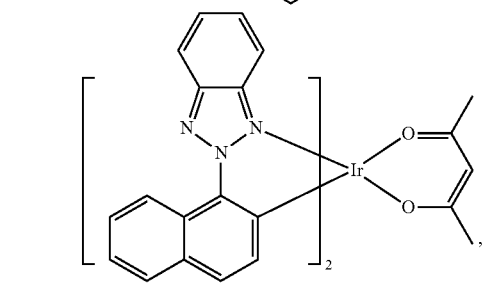
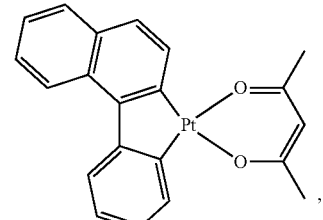
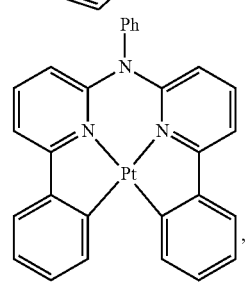
-continued
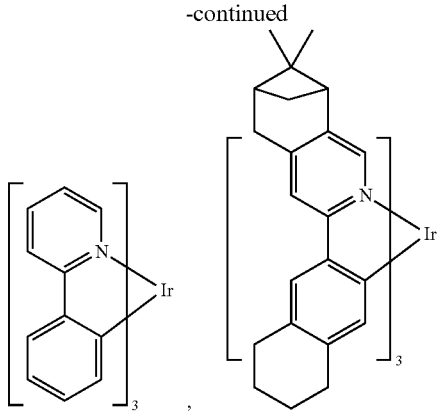
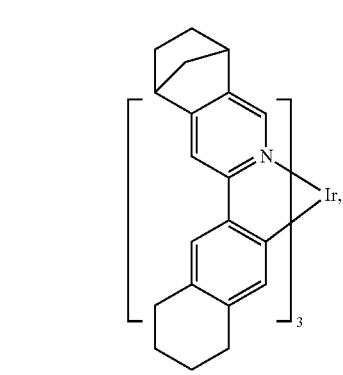
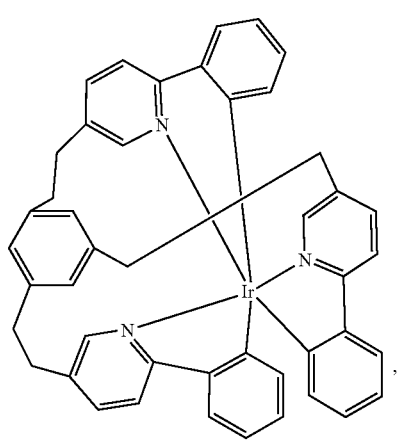
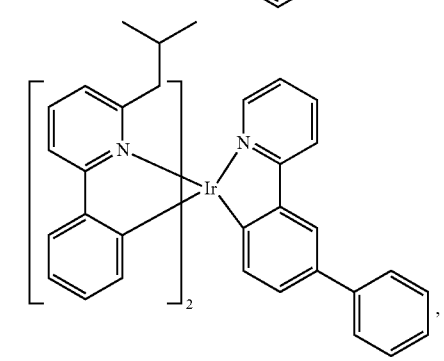

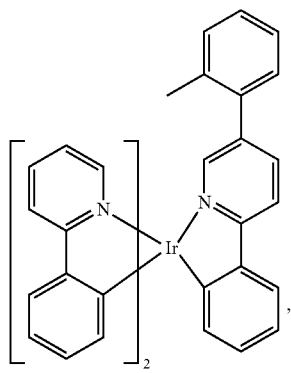
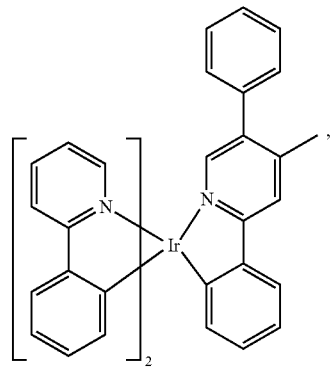
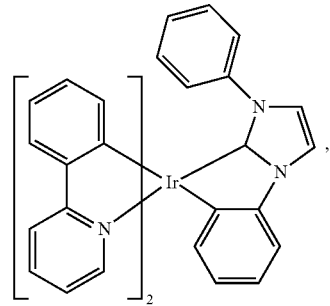
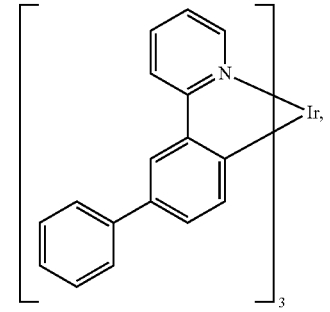
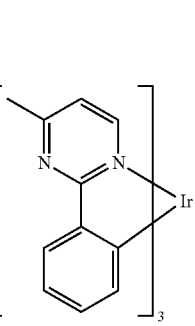
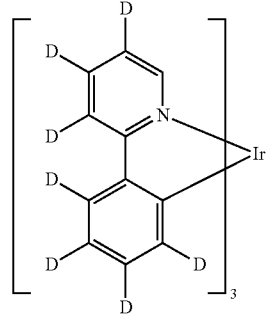
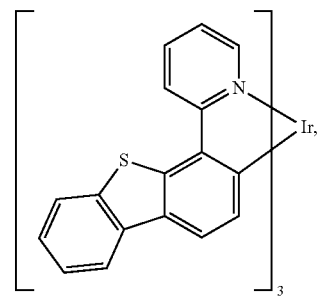
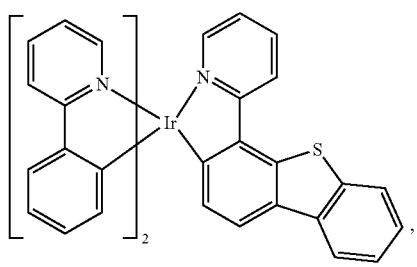
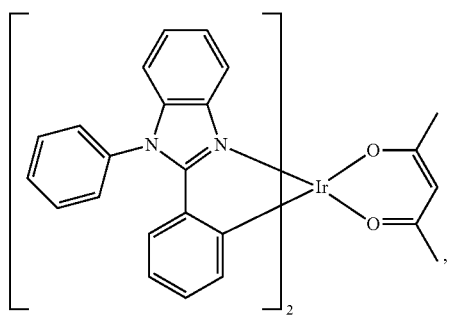
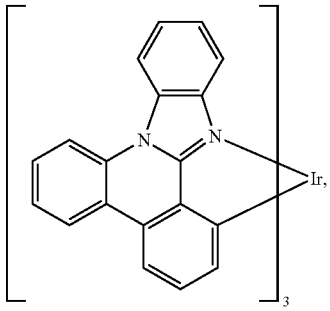
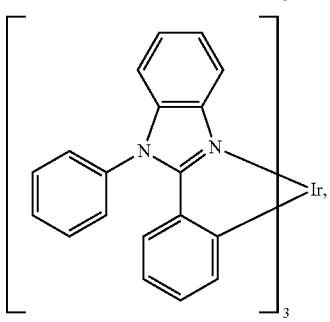

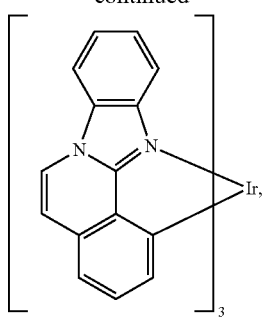
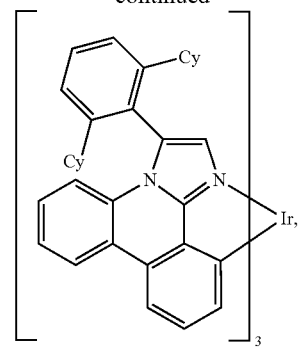
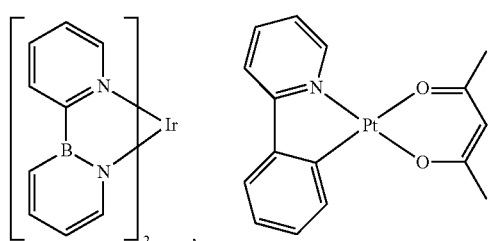
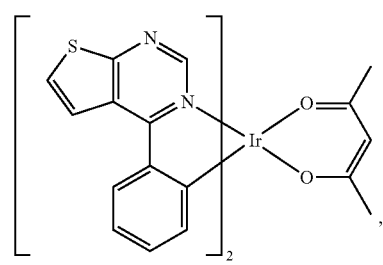
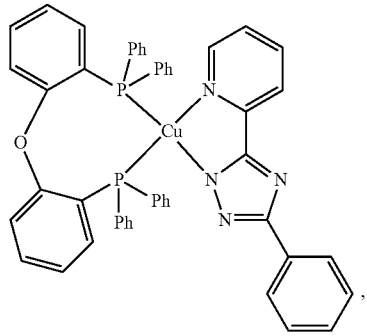
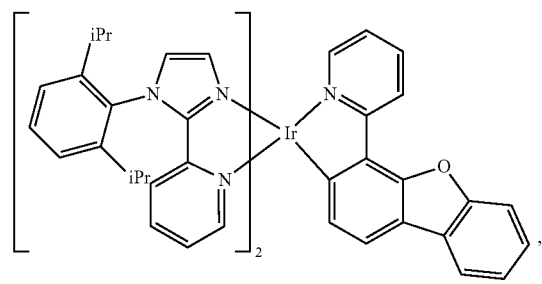
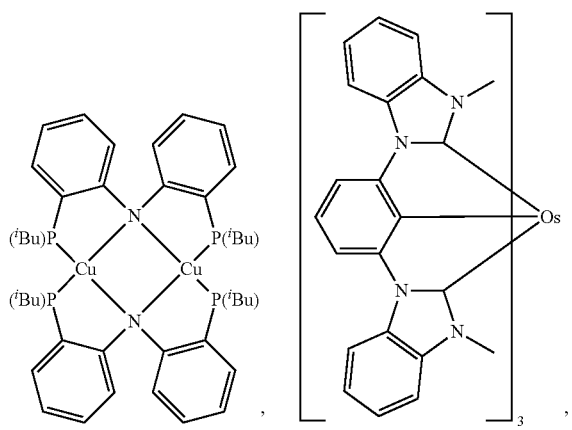
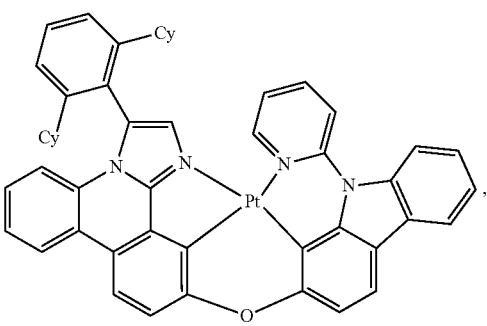
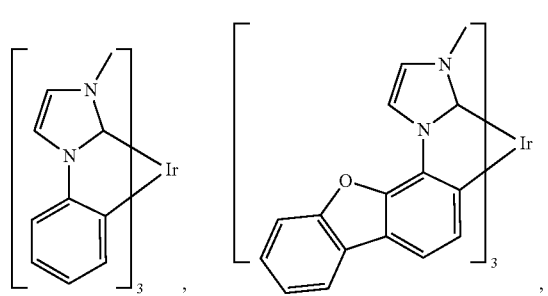
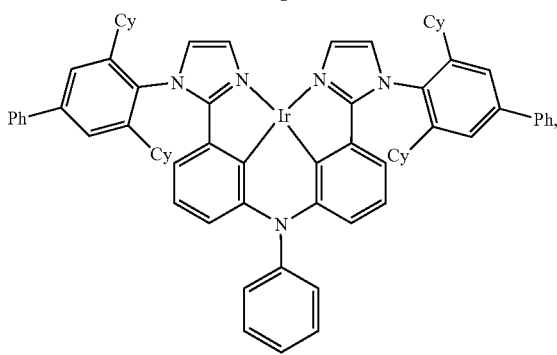

95
-continued
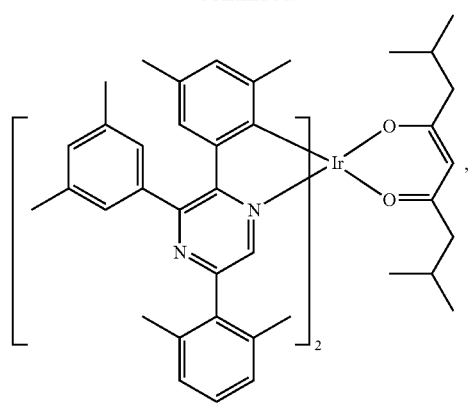
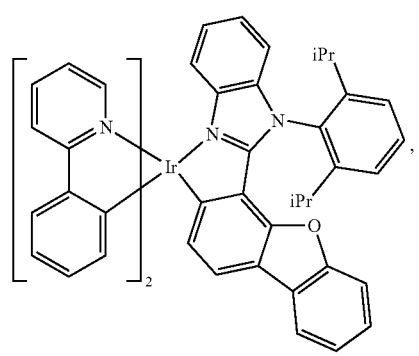
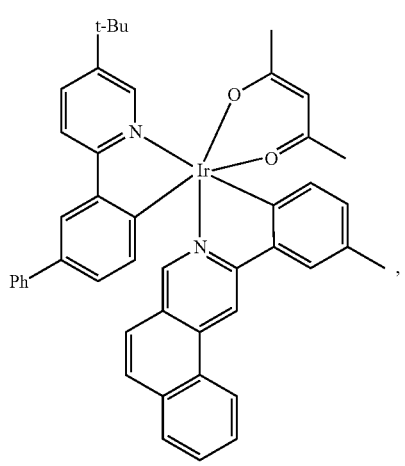
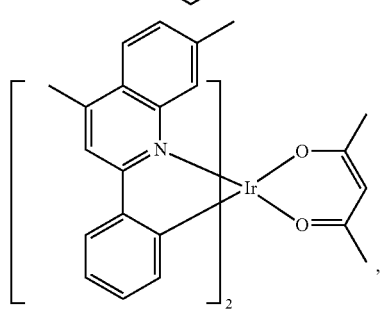
96
-continued
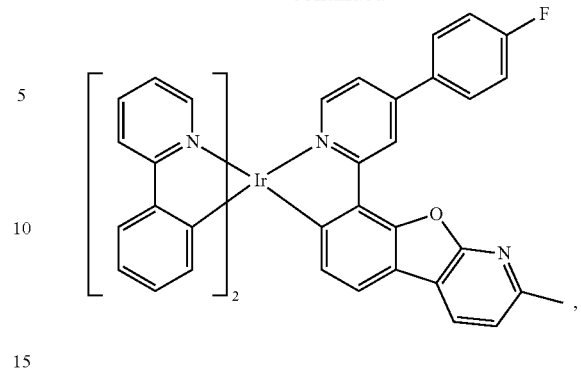
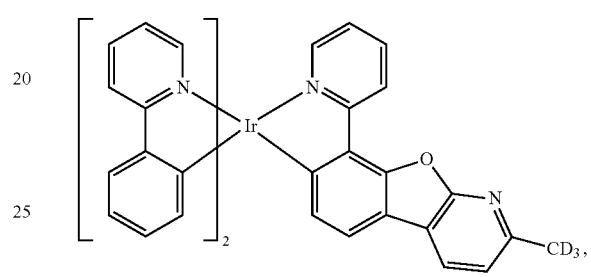
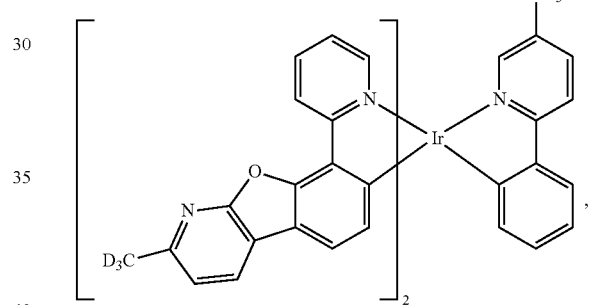
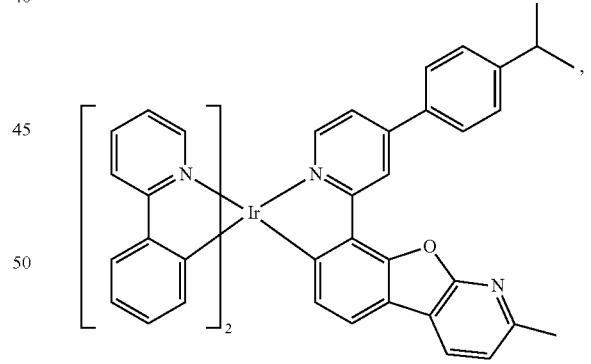
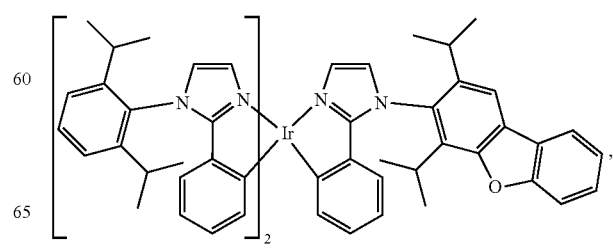

97
-continued
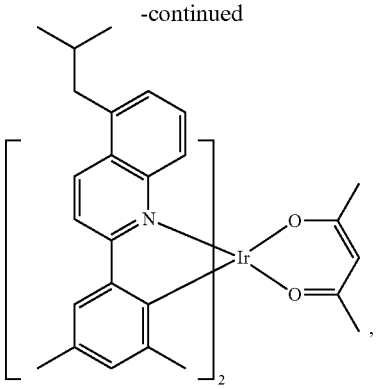
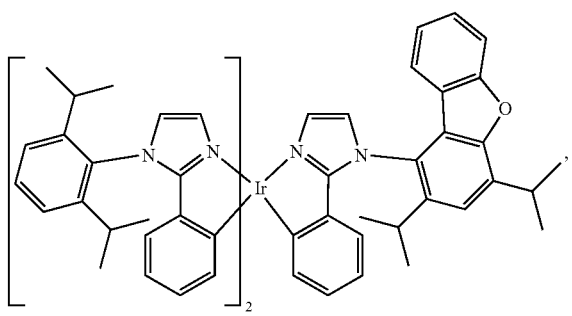
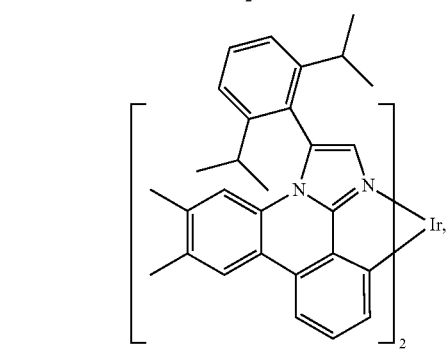
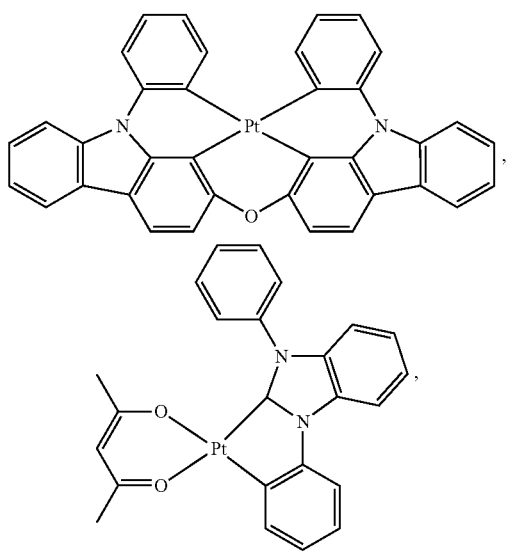
98
-continued
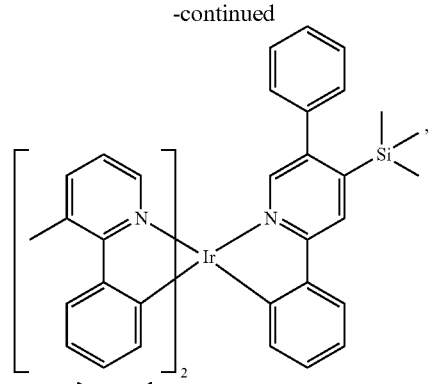
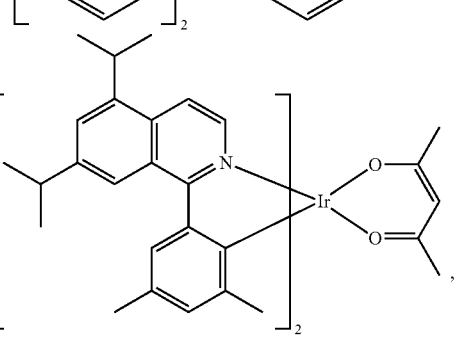
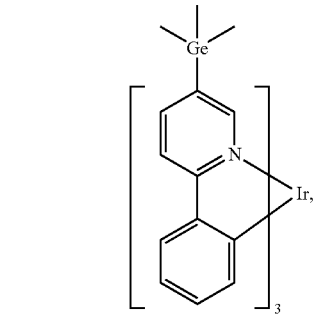
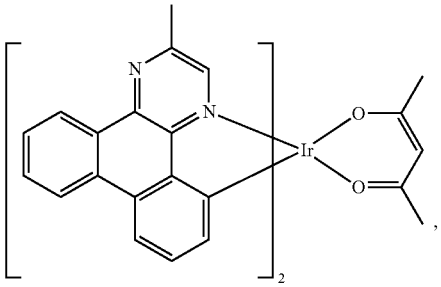
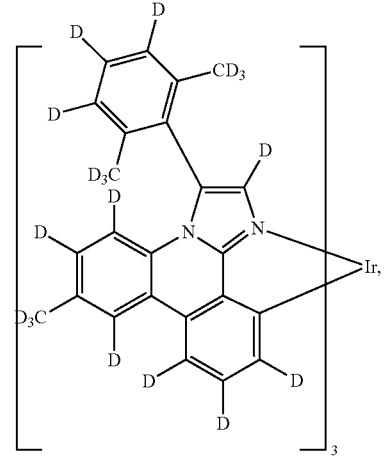

99
-continued
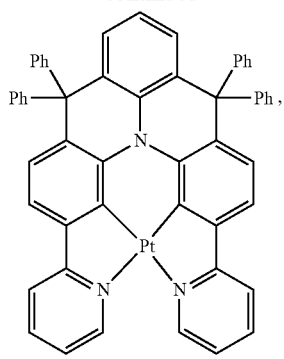
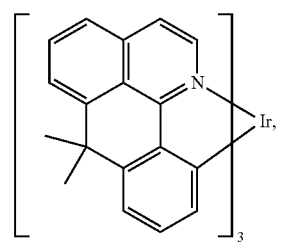
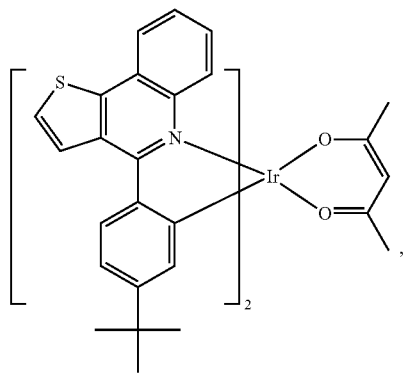
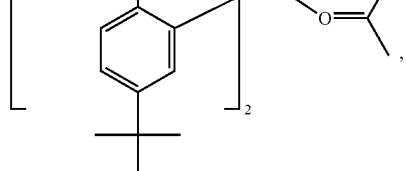
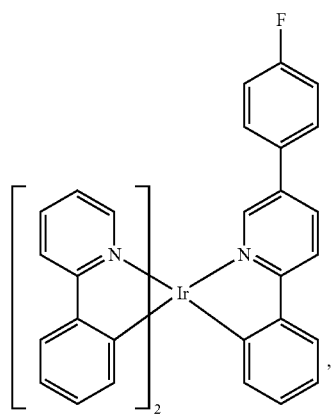
100
-continued
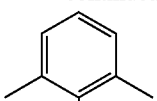
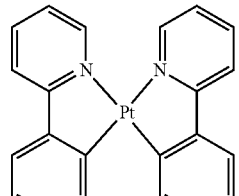
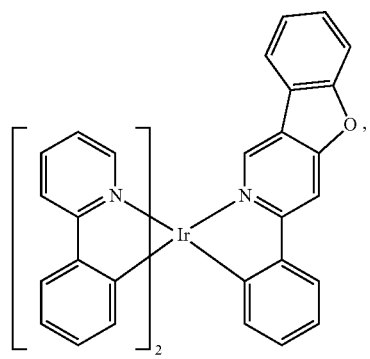
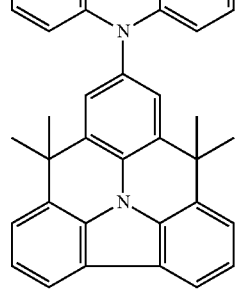
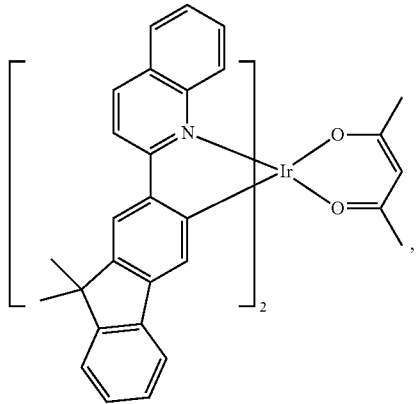

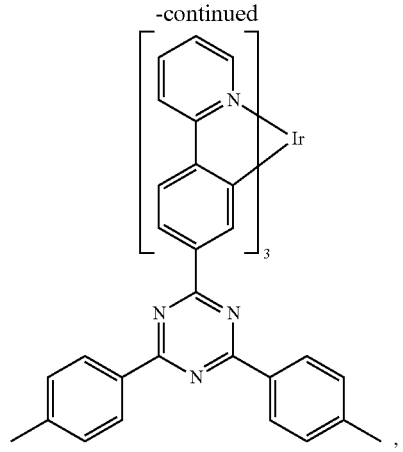
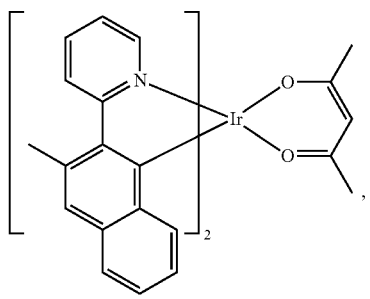
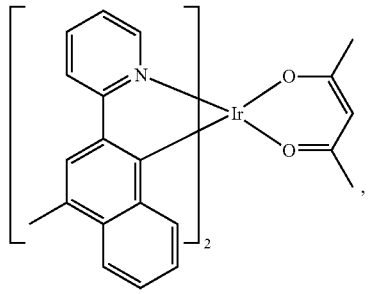
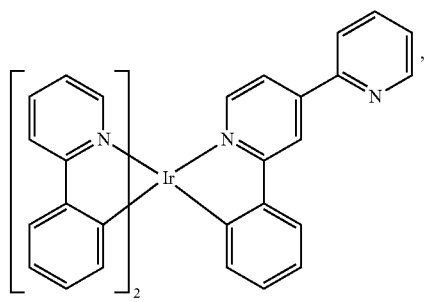
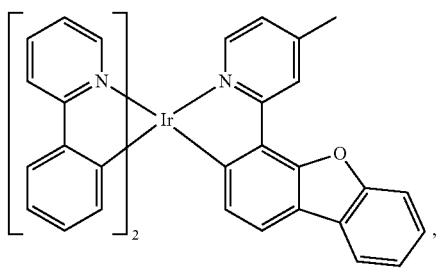
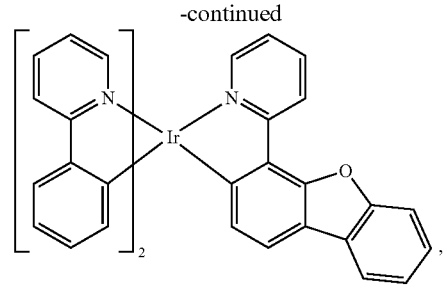
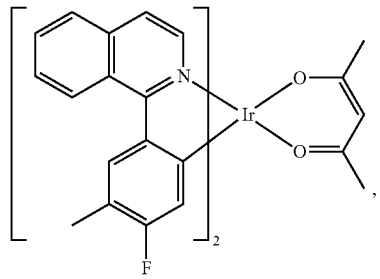
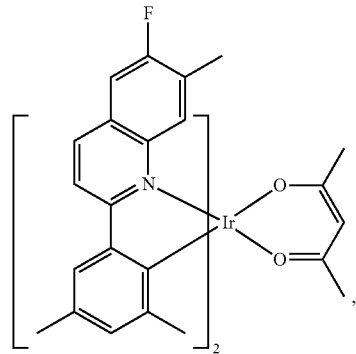
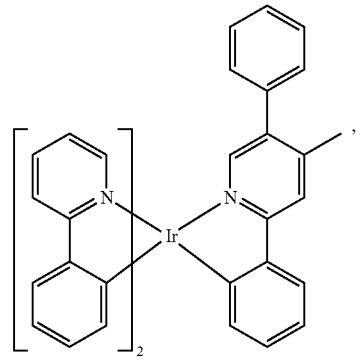
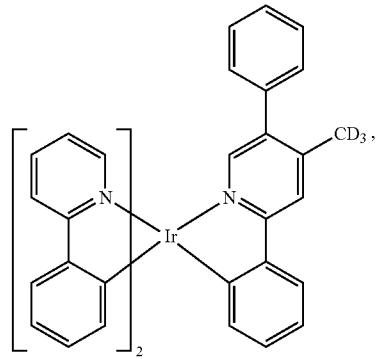

103                                  104
-continued                      -continued
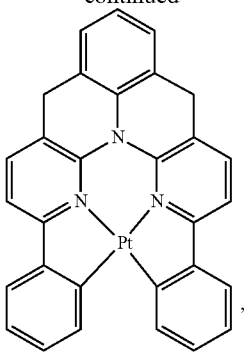
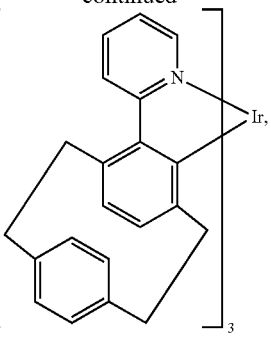
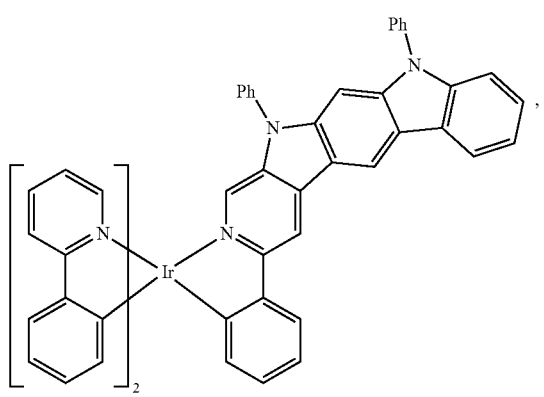
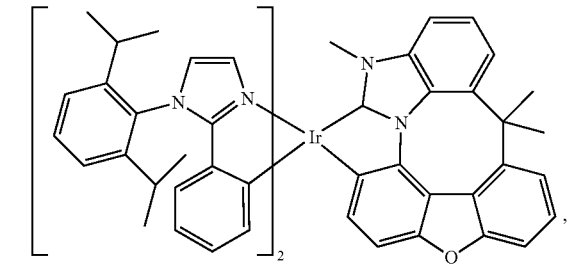
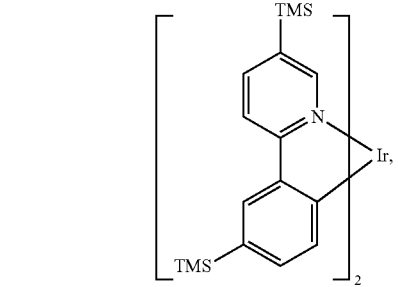
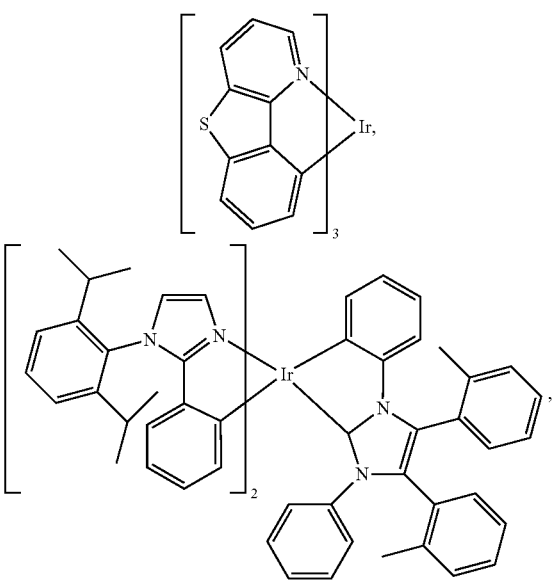

105
-continued
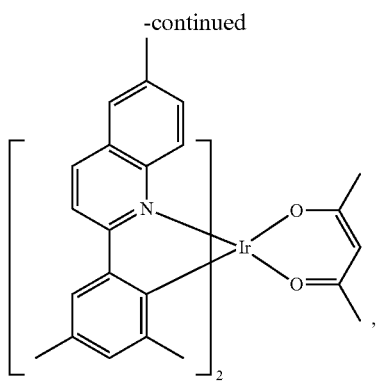
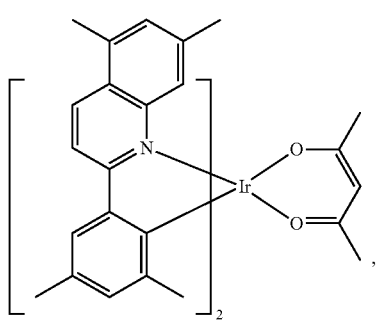
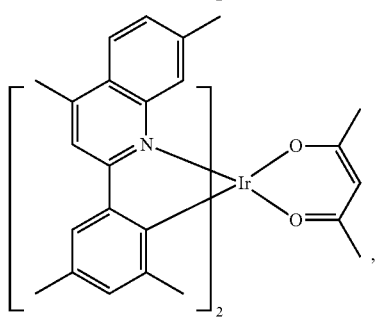
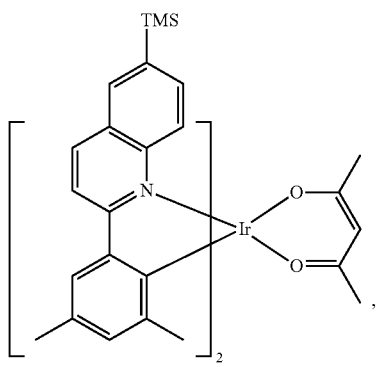
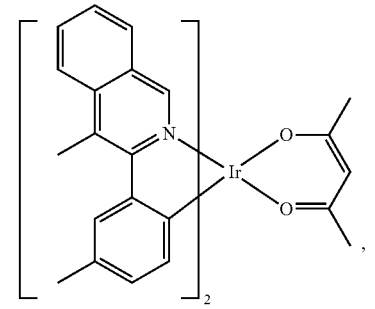
106
-continued
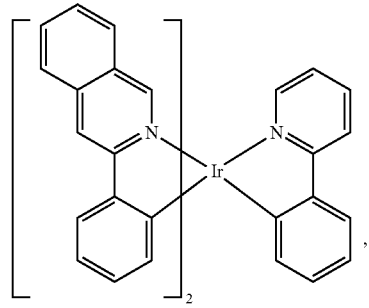
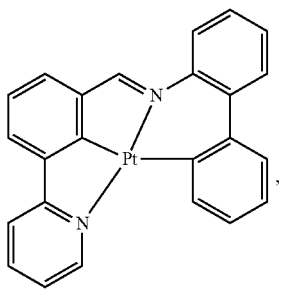
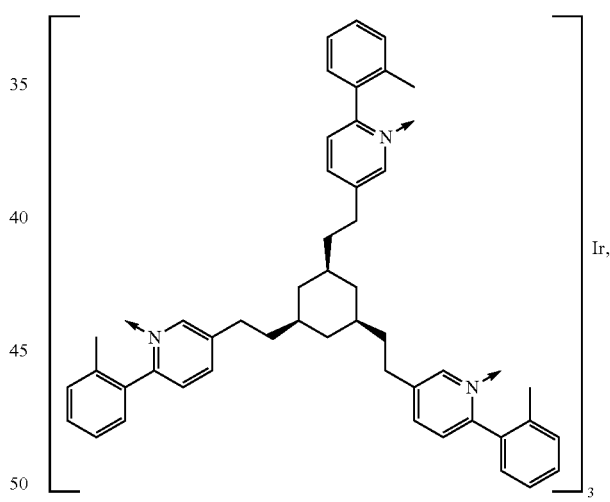
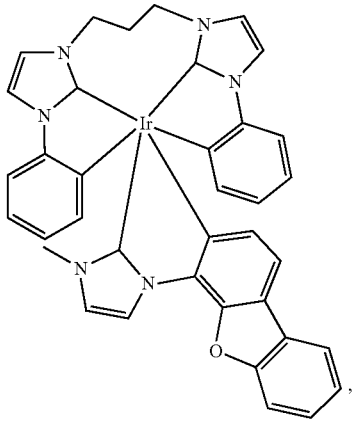

107
-continued
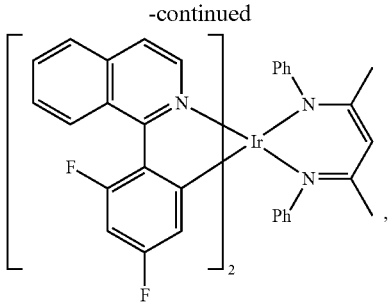
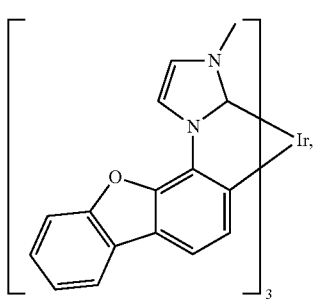
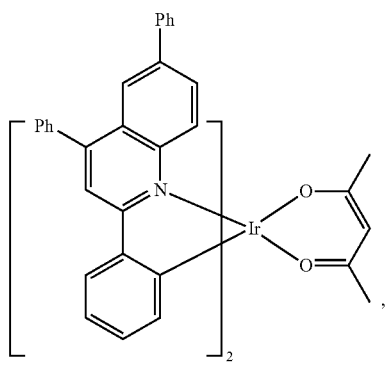
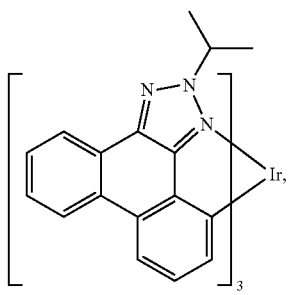
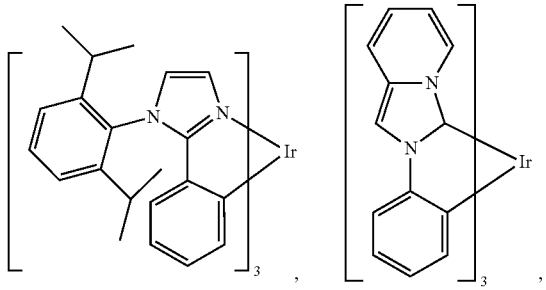
108
-continued
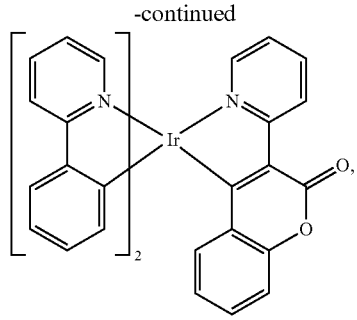
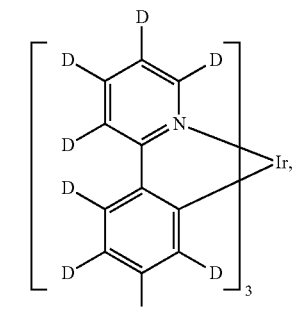
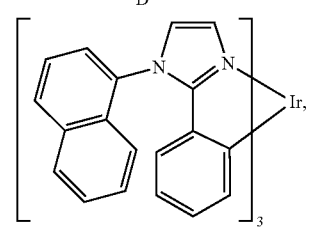
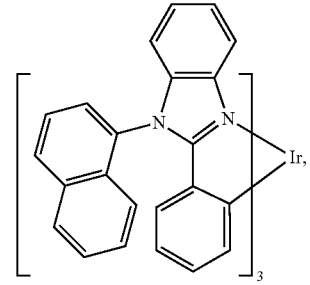
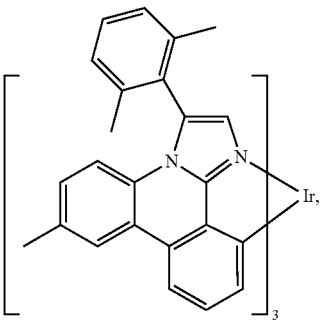
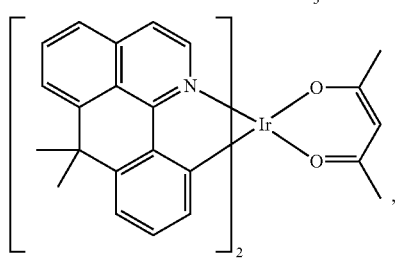

-continued

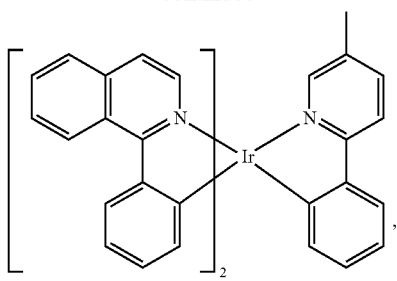

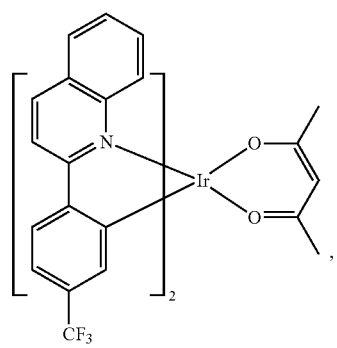

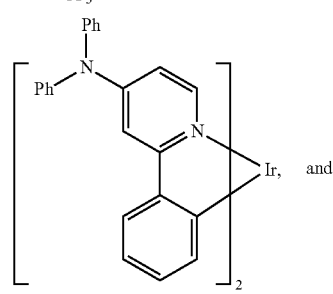

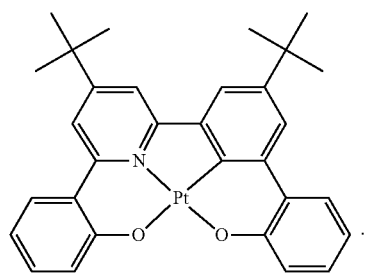

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

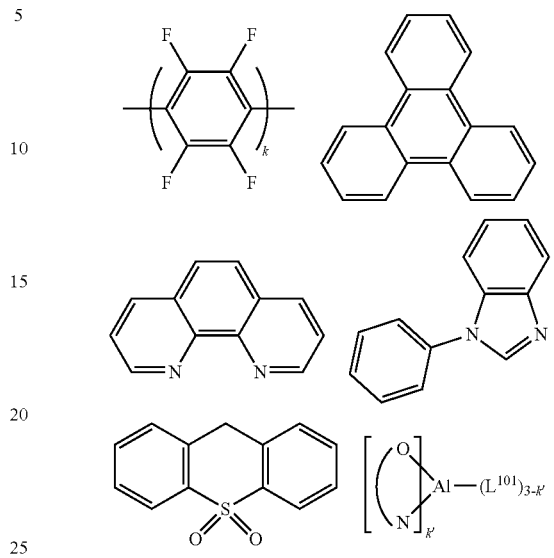

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

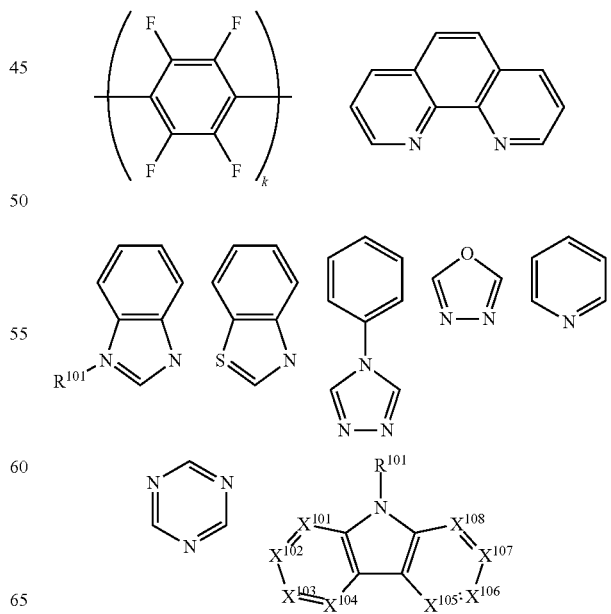

-continued

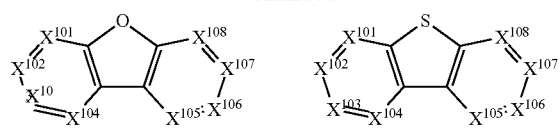

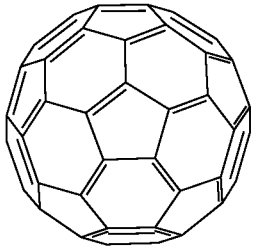

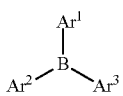

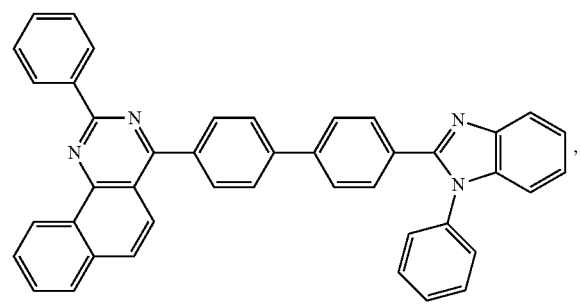

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

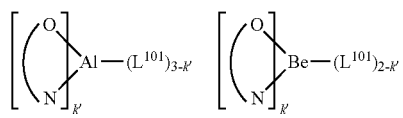

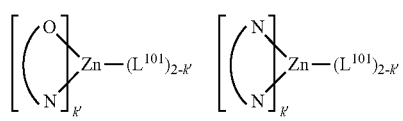

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

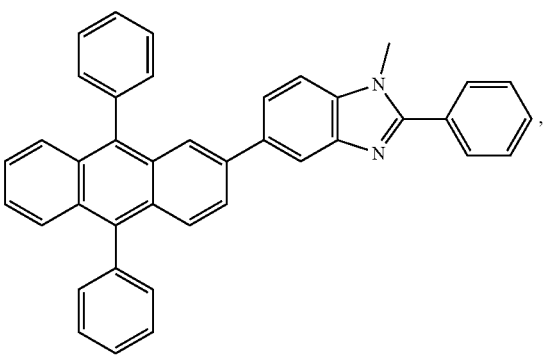

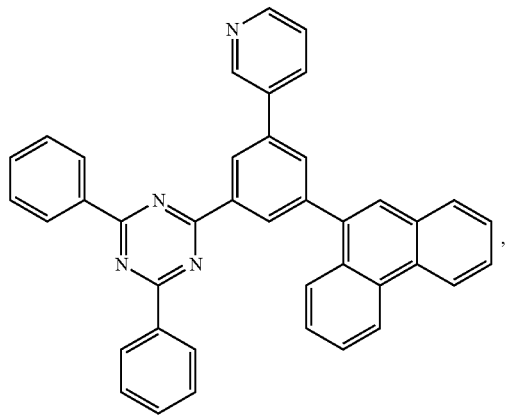

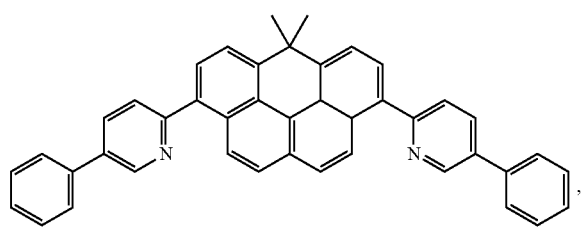

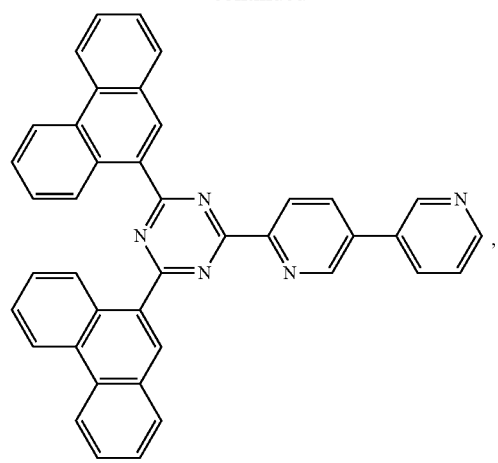
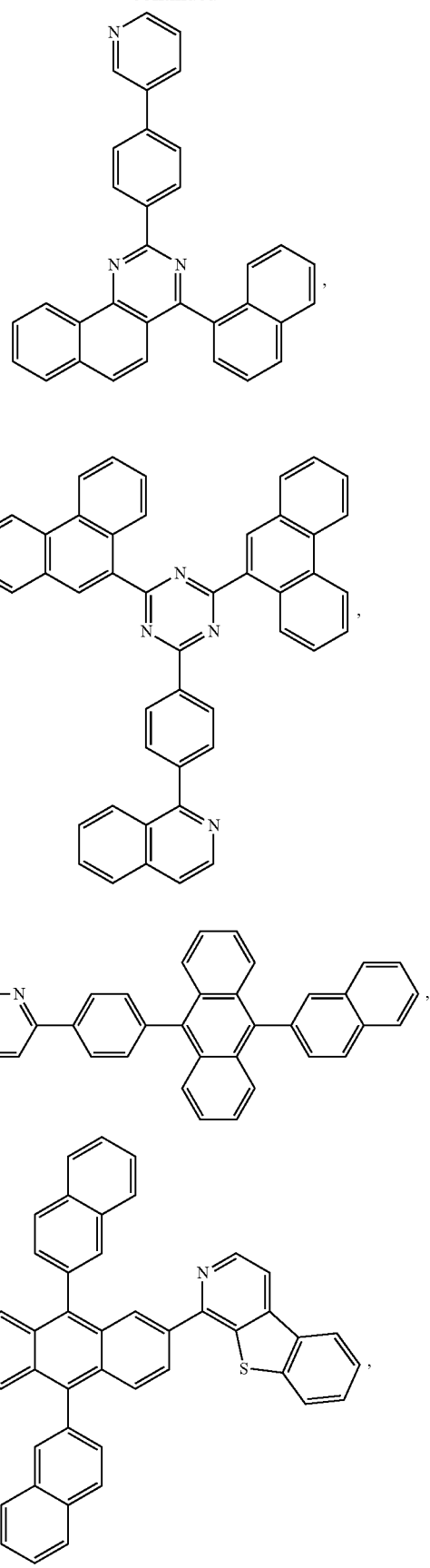

115
-continued
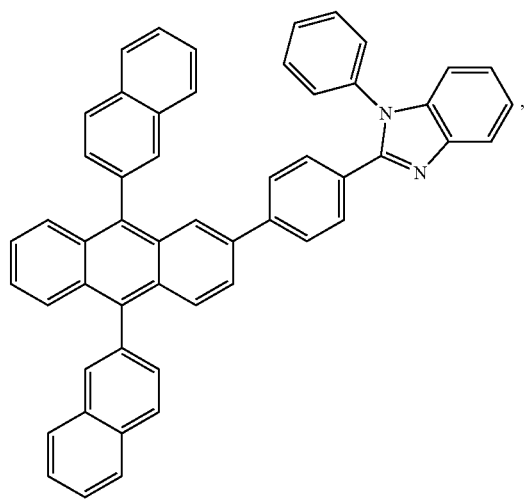
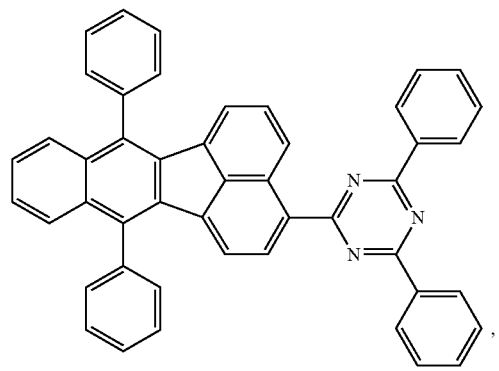
116
-continued
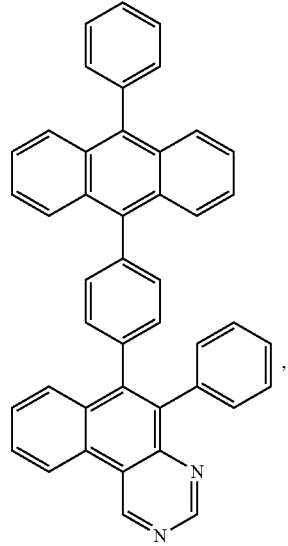
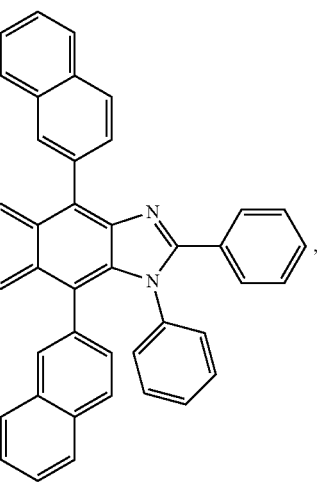
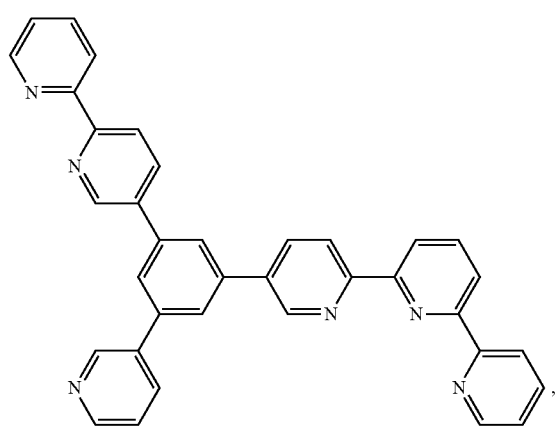
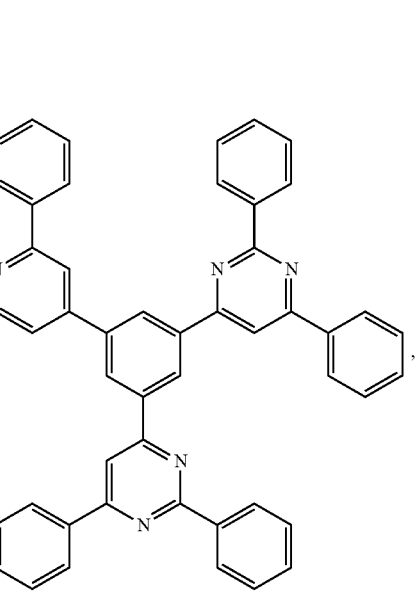

117
-continued
118
-continued
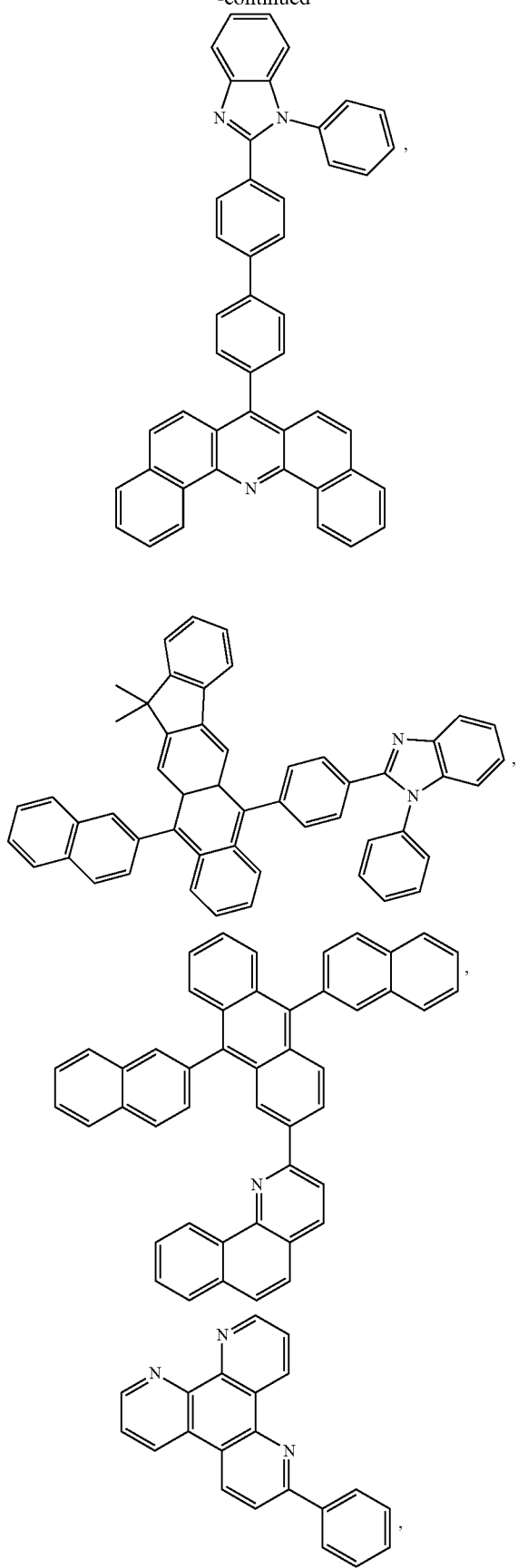
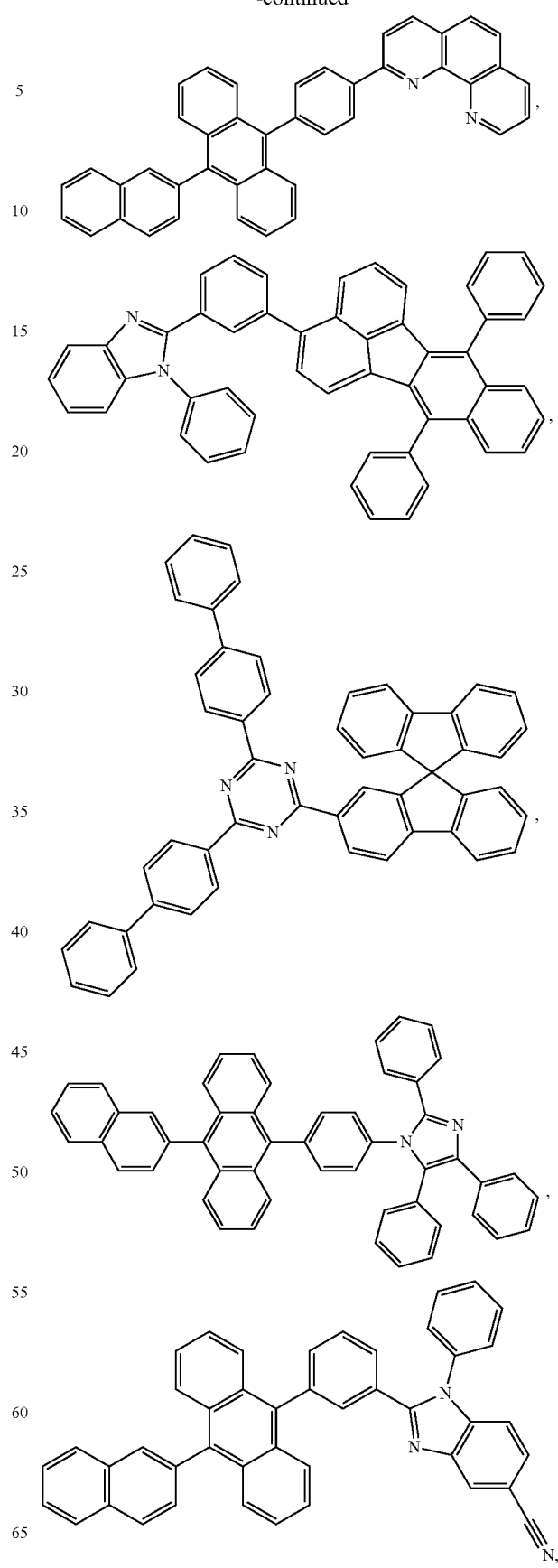

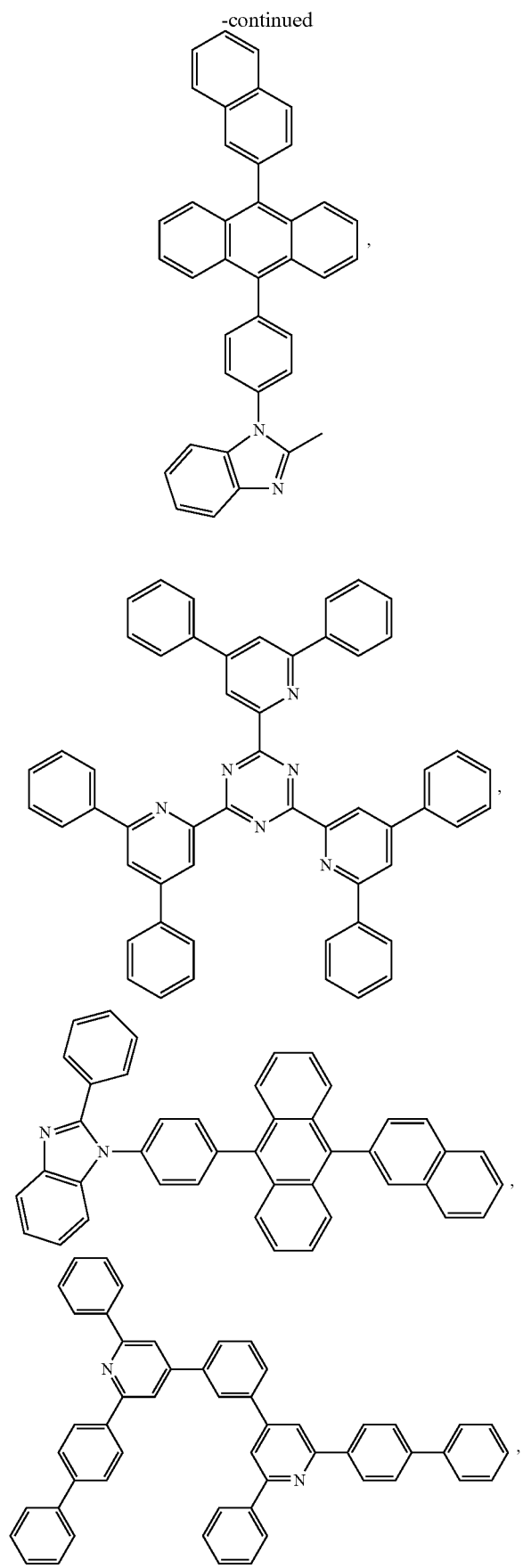

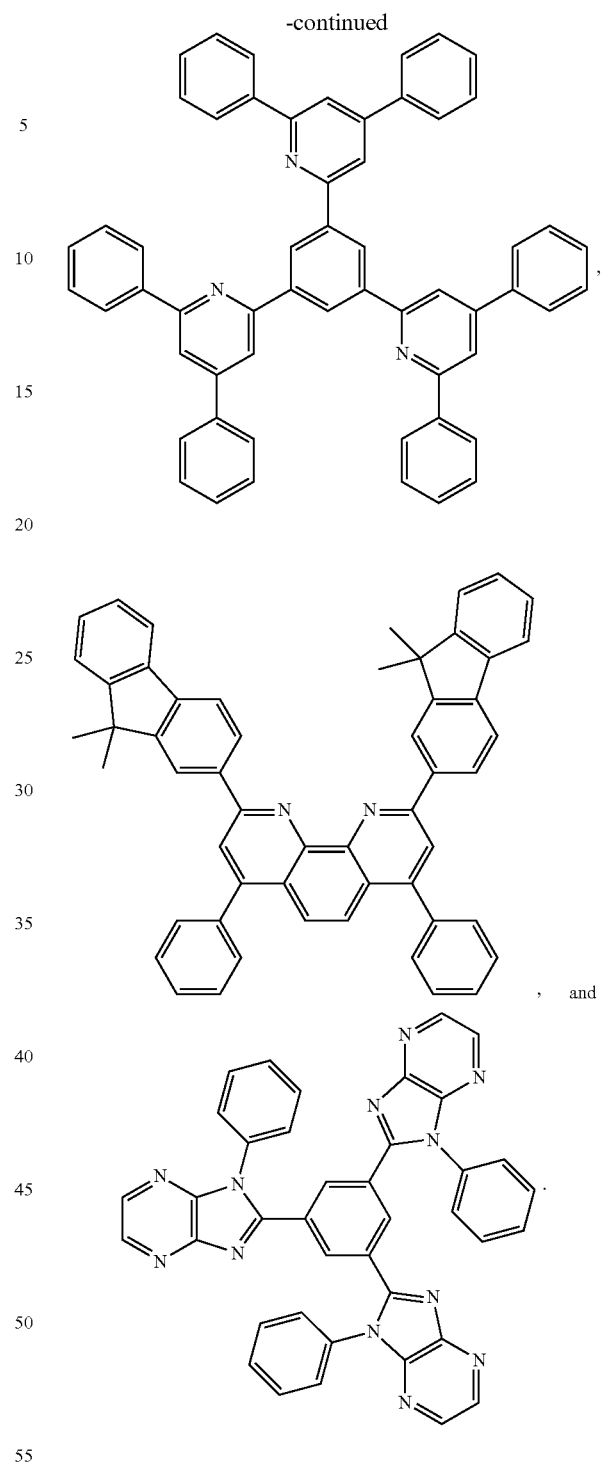

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

The schemes shown below are focused on (pyridyl)M (carbazole) and (carbene)M(carbazole) emitters, bridged by olefinic groups. The double bonded linkage was chosen here as a useful, however, any number of different linkages could be used, including aryl, ester, amide, triazole (click coupling) to achieve the coupling of the two dissimilar ligands. Further, while these examples involve two bridges to form the macrocycle, a single bridge may be sufficient to make the complexes thermally stable enough for efficient vacuum deposition.

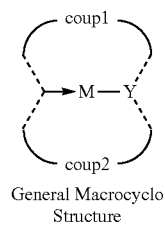

General Macrocyclo Structure

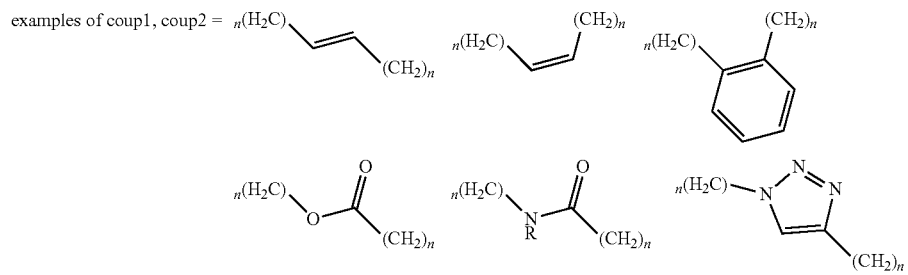

examples of coup1, coup2 =

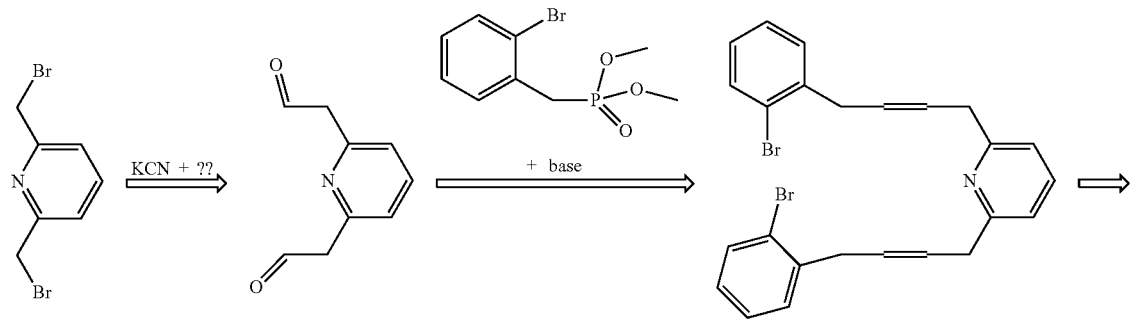

123 124
-continued
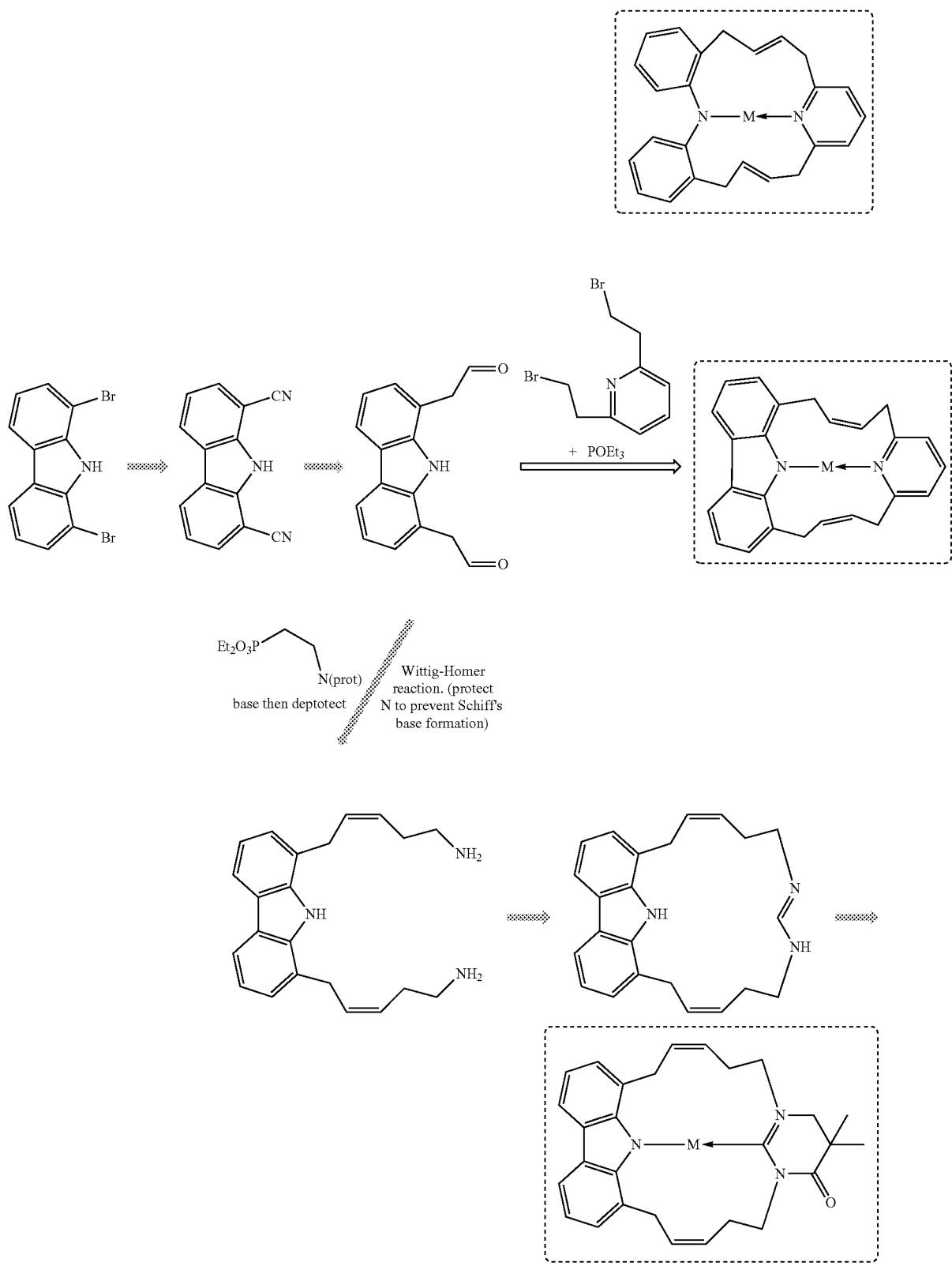
X = C, N, neutral ligand, e.g. carbene, pyridyl, etc.
Y = C, N, anionic ligand, e.g. amide, aryl, The Metal Template Route shown below has the benefit of not requiring a high dilution step to get good yields of the macrocycle. The metal ion brings to the two ligands together and a metathesis catalyst is used to close the linkage. Several different carbene and pyridyl ligands are shown. These reactions and others couple be used with a wide range of carbene and anionic ligands.

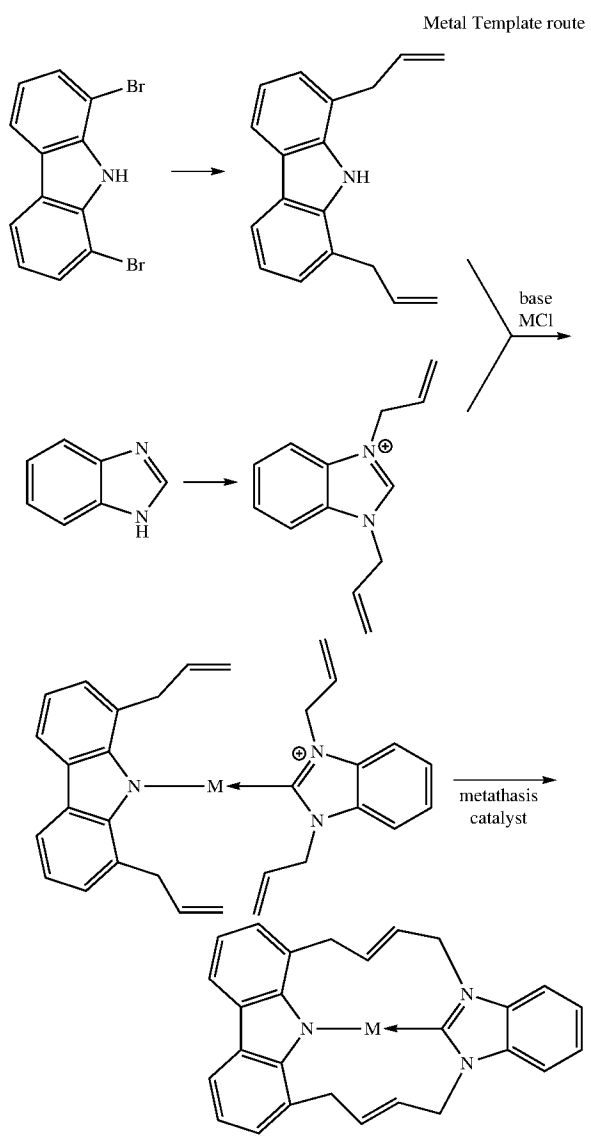

Metal Template route

Photophysical Properties

The luminescence spectra for compounds of Formula (I) is best described as thermally-activated-delayed fluorescence (TADF), which occurs when the higher lying singlet Si is thermally populated from the lowest triplet $T_1$. This thermal activation requires small energy separation between $S_1$ and $T_1$, and that explains an observed small shift or differences in the emission spectra at different temperatures. The radiative rate constants of compounds of Formula I are in the order of $10^5$ $s^{-1}$ which are comparable to those of efficient phosphorescent emitters with noble metals such as Ir(III) and Pt(II). The non-radiative rate constants increase as the emission is red-shifted most likely due to energy gap law.

The emission spectra for compounds of Formula I are blue-shifted upon cooling in fluid solvents like MeTHF and methylcyclohexane (MeCy) resulting from destabilization of the CT states in more rigid environment. The shift is greater in methylTHF, which is likely attributed to its greater polarity than methylcyclohexane. The effect is minimized in polystyrene films due to the more rigid solution environment. Due to the relative positions of the $^3CT$ and $^3Cz$ states, each compound behaves differently at lower temperature.

The radiative rate constants of the macrocyclic Cu(I) carbene-amide compounds of Formula I are as fast as those of phosphorescent emitters with heavy metal like Ir and Pt. The energy separation between the lowest excited singlet and triplet states needs to be small to obtain a short radiative TADF decay lifetime, which is important to maximize the photoluminescent quantum efficiency. Again, the emission spectra of many compounds at 77 K are barely shifted from those at RT which is also indicative of the small energy separation between the lowest triplet and singlet state. Therefore, it is of vital importance to measure $\Delta E(S_1-T_1)$ of these Cu compounds by temperature-dependent measurement. In fact, many of the macrocyclic carbene-Cu(I) amide compounds will have a $\Delta E(S_1-T_1)$ in a range from 10 meV to 150 meV, 20 meV to 120 meV, or 20 meV to 80 meV, which again, indicates that the compounds are TADF emitters.

The increase in lifetime at low temperature is attributed to successive depopulation of states at high energy that have radiative rate constants faster than the lowest lying state. At temperatures above 50 K, the emission is dominated by a higher-lying $S_1$ state, whose rate of thermal population increases with heating. At temperatures below 50 K, thermal activation between triplet substrates is observed. Under an assumption of a fast thermalization between states, the temperature dependent decay curve can be fit to the Boltzmann distribution equation (equation 1).

$$\tau = \frac{2 + e^{-\frac{\Delta E(III-I)}{k_B T}} + e^{-\frac{\Delta E(S_1-I)}{k_B T}}}{2\left(\frac{1}{\tau_{I,II}}\right) + \left(\frac{1}{\tau_{III}}\right)e^{-\frac{\Delta E(III-I)}{k_B T}} + \left(\frac{1}{\tau_{S_1}}\right)e^{-\frac{\Delta E(S_1-I)}{k_B T}}} \quad (1)$$

Here, $S_1$ represents the lowest singlet state, whereas I, II and III represent the triplet substates $^I T_1$, $^{II} T_1$ and $^{III} T_1$, and $k_B$ is the Boltzmann constant. Substates I and II are treated as being degenerate since the energy splitting between these two states are normally very small (<10 $cm^{-1}$) in copper complexes. Fits of the experimental lifetime data to equation 1 reveal the decay rate of each state and the energy separation between them. Fits are poor to a Boltzmann equation that does not include a second term to account for splitting of the triplet substates and plateau at T<50 K. The exchange energy is characterized by $\Delta E(S_1-^{III}T_1)$, which is determined to be 415 $cm^{-1}$ (51.5 meV). This energy separation is among the smallest values reported for Cu-based TADF emitters. The decay lifetime of the $S_1$ state ($\tau_{s_1}$=73.4 ns) is among the fastest values of $\tau_{s_1}$ for Cu complexes and consistent with the high $k_r$ as mentioned above.

The values obtained for $k_r(S_1-S_0)$, $\Delta E(S_1-^{III}T_1)$ and ZFS from the temperature dependence analysis of the compounds of Formula I are unique in comparison to data reported for luminescent four-coordinate Cu(I) complexes. The geometry of the complex maximizes R-overlap between the $2p_z$ orbitals on the ring T and the L coordinating member to the metal(I), and the highly polarizable 3d orbitals of the metal provide enough electron density to impart high oscillator strength to the $^1ICT$ transition. On the other hand, overlap between the HOMO and LUMO remains poor enough to minimize stabilization of the unpaired electrons in the $^3$ICT state, thereby minimizing the exchange energy.

$^3$Cz-based emission is indicated by the long-lived decay times and the vibronically-structured spectral lines as observed in frozen 2-MeTHF and MeCy at 77K. This is likely due to rigidochromic effects destabilizing the low-lying CT bands such that the lowest lying state at 77K is in fact largely $^3$Cz in nature.

The increase in the decay times observed in compounds of Formula I upon cooling is consistent with TADF. Temperature-dependent studies of PS films show the characteristic TADF curve, which can be fitted to equation (2) below.

$$\tau = \frac{3 + e^{\frac{\Delta E}{kT}}}{3\left(\frac{1}{\tau_1}\right) + \left(\frac{1}{\tau_2}\right)e^{-\frac{\Delta E}{kT}}} \quad (2)$$

An Arrhenius analysis allows us to extract the value of $\Delta E_{1CT-3CT}$, which is found to be exceedingly small in both compounds.

Photophysical and Electroluminescence Data of Compounds 12a, 13, and 14

Emission spectra at room temperature (RT) for many of the compounds of Formula I are broad and featureless, which can be indicative of the CT nature of the transitions. The trend in the energies of the emission maxima follows the magnitude of the Stokes shift between absorption and emission, and can be related to the extent of reorganization the complex undergoes when transitioning between the ground and excited states: with the silver compounds, having the longest carbene-amide distance and the smallest HOMO-LUMO overlap, exhibiting the largest Stokes shift between absorption and emission, and the most red-shifted emission $\lambda_{max}$. The corresponding gold compounds exhibit an intermediate carbene-amide distance follows the trend as well, and lastly the corresponding copper compounds exhibit the shortest carbene-amide separation, the smallest Stokes shift, and the highest energy of emission $\lambda_{max}$.

At room temperature, many compounds show remarkably high photoluminescence quantum yields ($\Phi_{PL}$) in MeCy. The excited state lifetime of the gold compounds having the heavier gold atom, and therefore, an expected stronger spin-orbit coupling exhibits a more efficient inter-system crossing (ISC). Interestingly, the silver compounds tend to exhibit the fastest radiative rate of all three compounds, with $k_r=2\times10^6$ s$^{-1}$ which to our knowledge makes the Ag(I) compounds the most efficient Ag(I)-based emitter in fluid medium to date.

Time-dependent DFT (TDDFT) calculations also reveal trends that largely match experiment, with the oscillator strengths (f) of the lowest-energy CT transitions (predominantly HOMO to LUMO in character) trending in the following order of increasing strength: $f_{Ag}<f_{Cu}<F_{Au}$. Furthermore, the calculated $S_1-T_1$ splitting, $\Delta E_{S1-T1}$ is reproduced in the trends observed in the increasing HOMO-LUMO separation from Cu<Au<Ag. The calculated bond lengths match the experimental ones observed in the crystal structures. The DFT data above highlight the importance of maintaining minimal HOMO/LUMO overlap as well as strong spin-orbit coupling by virtue of a heavy metal in order to obtain efficient TADF with sub-microsecond radiative lifetimes.

The emission spectra are red-shifted from polystyrene films to methylcyclohexane and to 2-methylTHF at room temperature due to the solvatochromic effect. The CT excited states are stabilized upon increasing the solvent polarity. Upon cooling to 77 K, the emission shows a strong mixture of CT and LE character in methylcyclohexane and methylTHF. The LE character is stronger in 2-methylTHF due to the stronger rigidochromic effect in the more polar solvent. It is worth noting that the LE character of the emission at 77 K in both methylcyclohexane and 2-methylTHF is more dominant in the gold compound than that of the copper compound, which is due to the heavy metal effect of Au on intersystem crossing between the singlet and triplet states. The more dominant LE character of the emission of the gold compound at 77 K is therefore attributed to enhanced ISC due to the heavier Au nucleus.

A series of temperature-dependent emission spectra of the ligand carbazoyl-compounds of Formula I, 5 wt % PMMA film exhibit a change with increasing temperature. A sharp emission line at 77K is indicative of carbazole based phosphorescence. Moreover, the relatively long lifetime at 77K is indicative of an organic triplet, as expected for a carbaozole based triplet. As the temperature is increased from 77K a broad emission line grows in, indicative of an MLCT transition, which includes an edge at higher energy than that of the carbazole based emission. At low temperature the excited state is trapped in the lower energy carbazole state because the thermal energy is too low to promote the molecule into the highly luminescent MLCT state. The marked decrease in lifetime on warming to room temperature is consistent with efficiency emission from an MLCT due to enhanced spin orbit coupling available to the metal compound. The mechanism of emission at room temperature is termed Thermally Assisted Phosphorescence (TAP).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound of Formula I

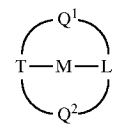

Formula I wherein

M is a metal selected from the group consisting of Cu, Ag, and Au;

T is a five-membered or six-membered heterocyclic ring, which is optionally substituted, wherein T includes a carbene carbon coordinated to M, or T is aromatic and includes a sp$^2$ nitrogen coordinated to M;

L is a group comprising an anionic coordinating member selected from the group consisting of C, N, O, S, and P, wherein the anionic coordinating member coordinates L to M; and Q$^1$ and Q$^2$ are each independently a linker, wherein the linker connects T to the anionic coordinating member of L to form a macrocyclic ligand coordinated to M; wherein the compound is neutral.

2. The compound of claim 1, wherein T is selected from the group consisting of:

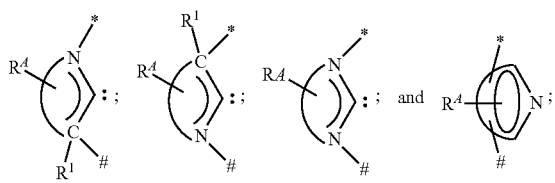

wherein
R$^A$ represents mono to the maximum allowable substitution, or no substitution and each R$^A$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, nitrile, isonitrile, sulfanyl, boryl, acyl, carboxylic acid, ether, ester, sulfinyl, sulfonyl, phosphino and combinations thereof;
each R$^1$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, nitrile, isonitrile, sulfanyl, boryl, acyl, carboxylic acid, ether, ester, sulfinyl, sulfonyl, phosphino and combinations thereof;
wherein any two adjacent R$^A$ are optionally joined or fused together to form a ring which is optionally substituted; adjacent R$^A$ and Ware optionally joined for fused together to form a ring which is optionally substituted; and
* represents a connection to Q$^1$ and # represents a connection to Q$^2$.

3. The compound of claim 1, wherein L is a group of formula L1 and the anionic coordinating member of L is C

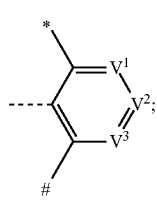

formula L1 wherein
* represents a connection to Q$^1$ and # represents a connection to Q$^2$, and the dotted line represents coordination to M;
V$^1$, V$^2$, and V$^3$ are independently selected from the group consisting of CR$^B$ and N, wherein at least one of V$^1$, V$^2$, or V$^3$ is CR$^B$; and
each R$^B$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, nitrile, isonitrile, sulfanyl, and combinations thereof; wherein, any two adjacent R$^B$ are optionally joined or fused to form a ring, which is optionally substituted; or
L is a group of formula L2 and the anionic coordinating member of L is N

formula L2 wherein
* represents a connection to Q$^1$ and # represents a connection to Q$^2$, and the dotted line represents coordination to M;
T$^1$ and T$^2$ are each independently a group comprising a sp$^2$ C or a sp$^3$ C, wherein T$^1$ and T$^2$ are optionally joined or fused to form a ring, which is optionally substituted;
R$^B$ represents mono to the maximum allowable substitution, or no substitution, and each R$^B$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, nitrile, isonitrile, sulfanyl, and combinations thereof, wherein any two adjacent R$^B$ are optionally joined or fused to form a ring, which is optionally substituted.

4. The compound of claim 3, wherein R$^A$ and R$^B$ are each independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

5. The compound of claim 1, wherein Q$^1$ and Q$^2$ each independently comprise a backbone of five to ten member atoms, and Q$^1$ and Q$^2$ each independently optionally comprises a five-membered or six-membered carbocyclic or heterocyclic ring.

6. The compound of claim 3, wherein the formula L2 is

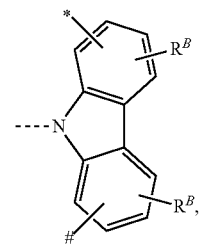

or an aza-analog thereof.

7. The compound of claim 1, wherein the compound has an emission lifetime of 0.01 µs to 5 µs.

8. The compound of claim 1 wherein the compound has an energy separation (ΔE) of the lowest excited singlet state and triplet states from 10 meV to 150 meV.

9. The compound of claim 1 wherein the compound has an emission wavelength of 450 nm to 650 nm.

10. The compound of claim 1, wherein M is Ag(I).

11. The compound of claim 5, wherein the formula L2 is selected from the group consisting of

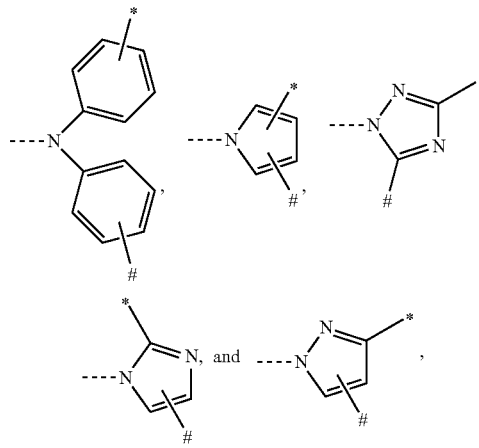

or an aza-analog thereof.

12. The compound of claim 1, wherein the compound is a compound of Formula IA, Formula IB or Formula IC:

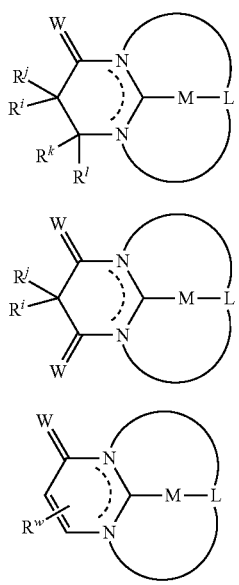

wherein
each M is a metal independently selected from the group consisting of Cu, Ag, and Au;
each L is group comprising an anionic coordinating member independently selected from the group consisting of C, N, O, S, and P;
each W is independently selected from the group consisting of O, S, $CR'''R''$, $SiR'''R''$, and $GeR'''R''$;
$R^w$ represents mono to the maximum allowable substitution, or no substitution;
each $R^i$, $R^j$, $R^k$, $R^l$, $R^m$, $R^n$, and $R^w$ is independently hydrogen or a substituent selected from the group consisting of, deuterium, halogen, alkyl, cycloalkyl, heteroalkyl, arylalkyl, amino, silyl, aryl, heteroaryl, and combinations thereof;

any two $R^i$, $R^j$, $R^k$, and $R^l$ are optionally joined for fused together to form a ring which is optionally substituted;
any two adjacent $R^m$ and $R^n$ are optionally joined for fused together to form a ring which is optionally substituted; and
any two adjacent $R^w$ are optionally joined for fused together to form a ring which is optionally substituted.

13. The compound of claim 1, wherein the compound is selected from the group consisting of:

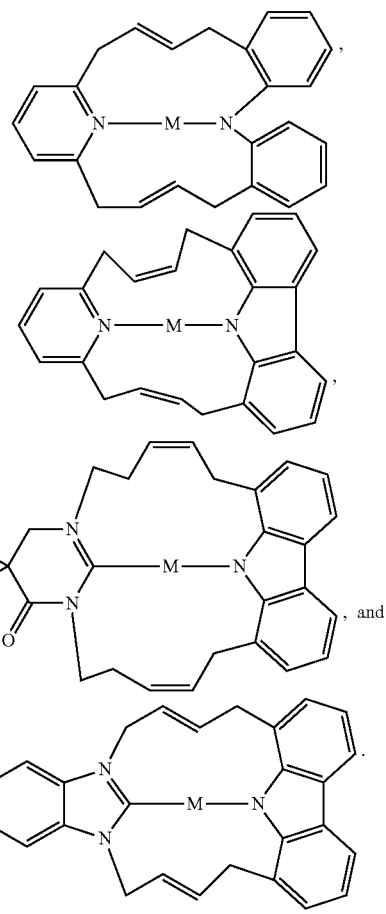

14. An organic electroluminescent device (OLED) comprising: an anode, a cathode, and an organic layer disposed between the anode and the cathode comprising a compound of Formula I,

wherein
M is a metal selected from the group consisting of Cu, Ag, and Au;
T is a five-membered or six-membered heterocyclic ring, which is optionally substituted, wherein T includes a carbene carbon coordinated to M, or T is aromatic and includes a $sp^2$ nitrogen coordinated to M;

L is a group comprising an anionic coordinating member selected from the group consisting of C, N, O, S, and P, wherein the anionic coordinating member coordinates L to M; and $Q^1$ and $Q^2$ are each independently a linker, wherein the linker connects T to the anionic coordinating member of L to form a macrocyclic ligand coordinated to M; wherein the compound is neutral.

15. The OLED of claim 14, wherein the device emits a luminescent radiation at room temperature when a voltage is applied across the organic light emitting device, and the luminescent radiation comprises a first radiation component that arises from a delayed fluorescent process or triplet exciton harvesting process.

16. The OLED of claim 14, wherein the organic layer further comprises a host, wherein the host comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

17. A consumer product comprising an organic light-emitting device (OLED), the OLED comprising an anode, a cathode, and an organic layer disposed between the anode and the cathode comprising a compound of Formula I,

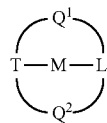

Formula I wherein

M is a metal selected from the group consisting of Cu, Ag, and Au;

T is a five-membered or six-membered heterocyclic ring, which is optionally substituted, wherein T includes a carbene carbon coordinated to M, or T is aromatic and includes a $sp^2$ nitrogen coordinated to M;

L is a group comprising an anionic coordinating member selected from the group consisting of C, N, O, S, and P, wherein the anionic coordinating member coordinates L to M; and $Q^1$ and $Q^2$ are each independently a linker, wherein the linker connects T to the anionic coordinating member of L to form a macrocyclic ligand coordinated to M;

wherein the compound is neutral.

18. The consumer product of claim 17, wherein the consumer product is selected from the group consisting of a flat panel display, a computer monitor, a medical monitors television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a microdisplay, a 3-D display, a virtual reality or augmented reality display, a vehicle, a large area wall, a theater or stadium screen, a light therapy device, and a sign.

19. A formulation comprising a compound according to claim 1.

\* \* \* \* \*